United States Patent
Li et al.

(10) Patent No.: US 12,258,367 B2
(45) Date of Patent: Mar. 25, 2025

(54) GLUCOSIDE DERIVATIVE THAT ACTS AS SGLT1 INHIBITOR AND APPLICATION THEREOF

(71) Applicant: MEDSHINE DISCOVERY INC., Jiangsu (CN)

(72) Inventors: Yi Li, Shanghai (CN); Tao Yu, Shanghai (CN); Qinghua Mao, Shanghai (CN); Chengde Wu, Shanghai (CN); Shuhui Chen, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 787 days.

(21) Appl. No.: 17/599,308

(22) PCT Filed: Mar. 30, 2020

(86) PCT No.: PCT/CN2020/082007
§ 371 (c)(1),
(2) Date: Sep. 28, 2021

(87) PCT Pub. No.: WO2020/200153
PCT Pub. Date: Oct. 8, 2020

(65) Prior Publication Data
US 2022/0153772 A1    May 19, 2022

(30) Foreign Application Priority Data

| Mar. 29, 2019 | (CN) | 201910251853.5 |
| Nov. 13, 2019 | (CN) | 201911104949.5 |
| Feb. 20, 2020 | (CN) | 202010105251.1 |

(51) Int. Cl.
*C07H 15/26* (2006.01)
*A61P 3/04* (2006.01)
*A61P 3/10* (2006.01)

(52) U.S. Cl.
CPC ............... *C07H 15/26* (2013.01); *A61P 3/04* (2018.01); *A61P 3/10* (2018.01)

(58) Field of Classification Search
CPC ...... C07H 15/14; C07H 15/26; C07H 405/12; A61P 3/04; A61P 3/10
USPC .......................................................... 514/24
See application file for complete search history.

(56) References Cited

FOREIGN PATENT DOCUMENTS

WO    WO 2014/081660 A1    5/2014

OTHER PUBLICATIONS

Sharma et al, Cellular Physiology and Biochemistry, 2017, 42, 1358-1365.*

* cited by examiner

*Primary Examiner* — Ganapathy Krishnan
(74) *Attorney, Agent, or Firm* — Mintz Levin Cohn Ferris Glovsky and Popeo, P.C.

(57) ABSTRACT

A glucoside derivative that acts as an SGLT1 inhibitor and an application thereof in the preparation of a drug for SGLT1 related diseases. Specifically disclosed is a compound represented by formula (II), a tautomer thereof or a pharmaceutically acceptable composition thereof.

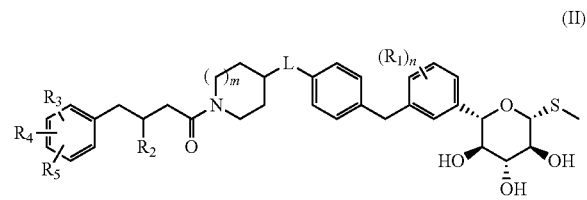

17 Claims, 5 Drawing Sheets

GLUCOSIDE DERIVATIVE THAT ACTS AS SGLT1 INHIBITOR AND APPLICATION THEREOF

REFERENCE TO RELATED APPLICATIONS

The present application is a United States National Phase under 35 U.S.C. § 371 of International Application No. PCT/CN2020/082007, filed Mar. 30, 2020, which claims the priority of:
CN201910251853.5, filed on Mar. 29, 2019;
CN201911104949.5, filed on Nov. 13, 2019; and
CN202010105251.1, filed on Feb. 20, 2020.
All of the foregoing applications are incorporated by reference in their entirety for all purposes.

FIELD OF THE INVENTION

The present disclosure relates to a class of glucoside derivatives as SGLT1 inhibitors, and use thereof in the manufacture of a medicament for a disease associated with SGLT1. In particular, the present disclosure relates to compounds represented by formula (II) and formula (I), or tautomers or pharmaceutically acceptable compositions thereof.

BACKGROUND OF THE INVENTION

Obesity, diabetes and related metabolic disorders caused by them have become major risk factors that threaten human health.

Sodium-glucose cotransporters (SGLTs) are a family of glucose transporters found in small intestinal mucosa and renal proximal tubules. The members of the family mainly include SGLT1 and SGLT2, whose function is to mediate transmembrane transport of glucose in the intestinal tract and the kidney. Specifically, SGLT1 is mainly distributed in intestinal mucosal cells of the small intestine, and is also expressed in a small amount in the myocardium and the kidney. The function of SGLT1 is mainly to regulate intestinal absorption process of glucose. SGLT2 is expressed at a high level in the kidney, and is mainly responsible for the regulation of the process of glucose reuptake by the kidney, that is, the glucose in the urine can actively attach to renal tubular epithelial cells when the glucose is filtered by renal glomerulus and be transported into cells by SGLT2 protein to be reused. The glucose transport process mediated by SGLTs does not intervene in sugar metabolism, thereby avoiding the occurrence of adverse reaction of hypoglycemia and reducing the risk of cardiovascular diseases. Therefore, SGLTs have gradually become one of ideal targets for the treatment of diabetes. In view of this, some SGLT inhibitors, especially highly selective SGLT2 inhibitors, have been developed one after another. By inhibiting the activity of SGLT2, they specifically inhibit the reabsorption of glucose by the kidney, thereby increasing the excretion of glucose in urine, and normalizing the blood glucose of diabetic patients. Since 2012, multiple SGLT2 inhibitors have been approved for marketing, becoming effective drugs for the treatment of diabetes.

In addition to the inhibition of SGLT2, studies in recent years have found that appropriate inhibition of SGLT1 can prevent the intestinal glucose uptake without causing obvious diarrhea or other gastrointestinal reactions. Moreover, the inhibition of SGLT1 can reduce the intestinal absorption of glucose into the blood, and in turn increase the concentration of glucose in the distal intestine, leading to increased levels of GLP-1 and PYY after meal, thereby exerting a better hypoglycemic effect and reducing the risk of urinary tract infection and kidney function damage. In addition, by controlling the intestinal absorption of glucose, the total energy intake in food can also be reduced, and by combining the effect of GLP-1 to reduce weight, the goal of double weight reduction can be achieved. Therefore, the development of SGLT1 inhibitors has become a new direction for the treatment of diabetes and obesity in recent years.

In summary, SGLT1 inhibitors have a good development prospect as a new type of drugs for the treatment of diabetes and obesity. But so far, the study on SGLT1 inhibitors is still in a clinical stage, and no drug has been approved for marketing. Currently, the SGLT1 inhibitor LX2761 developed by Lexicon which only acts on gastrointestinal tract is undergoing a clinical phase I study for the treatment of diabetes (WO2014081660).

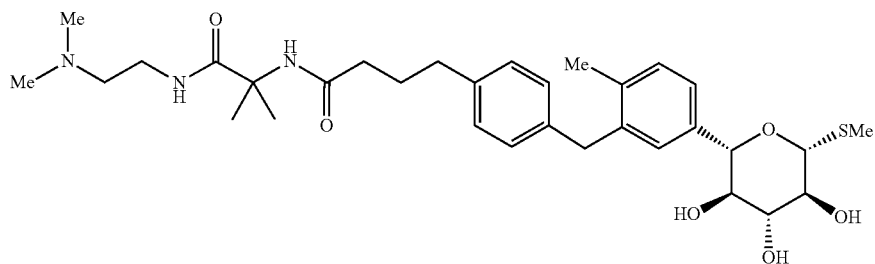

LX2761

SUMMARY OF THE INVENTION

The present disclosure provides a compound represented by formula (II), or an isomer or a pharmaceutically acceptable salt thereof,

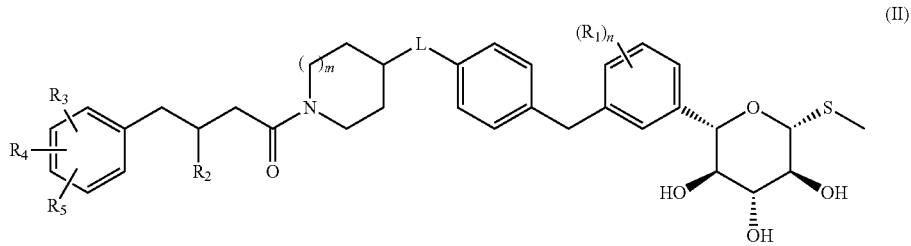

(II)

wherein
$R_1$ is selected from H, F, Cl, Br, I, OH, $NH_2$, CN, $C_{1-6}$ alkyl and $C_{1-6}$ alkoxy, wherein the $C_{1-6}$ alkyl and $C_{1-6}$ alkoxy are optionally substituted with 1, 2, or 3 $R_a$;
$R_2$ is selected from F, Cl, Br, I, OH, $NH_2$ and $C_{1-3}$ alkylamino;
$R_3$, $R_4$ and $R_5$ are each independently selected from H, F, Cl, Br, I, OH, $NH_2$, CN, and $C_{1-3}$ alkyl optionally substituted with 1, 2, or 3 $R_b$;
L is selected from single bond, —O—, —S—, —C($R_c$)$_2$—, and —N($R_d$)—;
m is selected from 0, 1, and 2;
n is selected from 1, 2, and 3;
$R_a$, $R_b$ and $R_c$ are each independently selected from F, Cl, Br, I, OH, $NH_2$, and $CH_3$;
$R_d$ is selected from H and $CH_3$.

In some embodiments of the present disclosure, the above-mentioned $R_1$ is selected from H, F, Cl, Br, I, OH, $NH_2$, CN, $CH_3$, $CH_2CH_3$, and ![structure]

wherein the $CH_3$, $CH_2CH_3$, and

![structure]

are optionally substituted with 1, 2, or 3 $R_a$, and other variables are as defined in the present disclosure.

In some embodiments of the present disclosure, the above-mentioned $R_1$ is selected from H, F, Cl, Br, I, OH, $NH_2$, CN, $CH_3$, $CH_2F$, $CHF_2$, $CF_3$, $CH_2CH_3$, and ![structure]

and other variables are as defined in the present disclosure.

In some embodiments of the present disclosure, the above-mentioned $R_2$ is selected from F, Cl, Br, I, OH, $NH_2$, $NH(CH_3)$, and $N(CH_3)_2$, and other variables are as defined in the present disclosure.

In some embodiments of the present disclosure, the above-mentioned $R_3$, $R_4$ and $R_5$ are each independently selected from H, F, Cl, Br, I, OH, $NH_2$, CN, and $CH_3$ optionally substituted with 1, 2, or 3 $R_b$, and other variables are as defined in the present disclosure.

In some embodiments of the present disclosure, the above-mentioned $R_3$, $R_4$ and $R_5$ are each independently selected from H, F, Cl, Br, I, OH, $NH_2$, CN, $CH_3$, $CH_2F$, $CHF_2$ and $CF_3$, and other variables are as defined in the present disclosure.

In some embodiments of the present disclosure, the above-mentioned L is selected from single bond, —O—, and —S—, and other variables are as defined in the present disclosure.

In some embodiments of the present disclosure, the above-mentioned moiety

![structure]

is selected from

![structures]

and other variables are as defined in the present disclosure.

In some embodiments of the present disclosure, the above-mentioned moiety

![structure]

is selected from

![structures]

and other variables are as defined in the present disclosure.

The present disclosure provides a compound represented by formula (I), or an isomer or a pharmaceutically acceptable salt thereof,

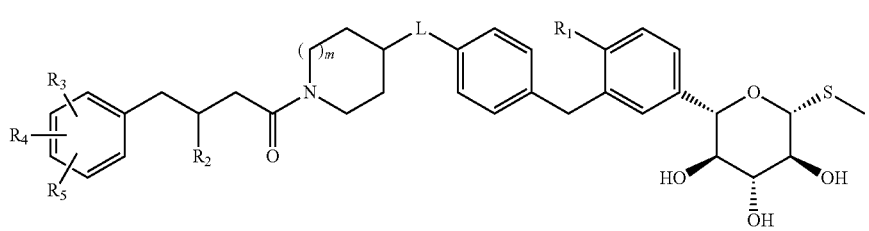

wherein
- $R_1$ is selected from H, F, Cl, Br, I, OH, $NH_2$, CN, $C_{1-6}$ alkyl and $C_{1-6}$ alkoxy, wherein the $C_{1-6}$ alkyl or $C_{1-6}$ alkoxy is optionally substituted with 1, 2, or 3 $R_a$;
- $R_2$ is selected from F, Cl, Br, I, OH, and $NH_2$;
- $R_3$, $R_4$ and $R_5$ are each independently selected from H, F, Cl, Br, I, OH, $NH_2$, CN, and $C_{1-3}$ alkyl optionally substituted with 1, 2, or 3 $R_b$;
- L is selected from single bond, —O—, —S—, —C($R_c$)$_2$—, and —N($R_d$)—;
- m is selected from 0, 1, and 2;
- $R_a$, $R_b$ and $R_c$ are each independently selected from F, Cl, Br, I, OH, $NH_2$ and $CH_3$;
- $R_d$ is selected from H and $CH_3$.

In some embodiments of the present disclosure, the above-mentioned $R_1$ is selected from H, F, Cl, Br, I, OH, $NH_2$, CN, $CH_3$, $CH_2CH_3$, and

wherein the $CH_3$, $CH_2CH_3$, and

are optionally substituted with 1, 2, or 3 $R_a$, and other variables are as defined in the present disclosure.

In some embodiments of the present disclosure, the above-mentioned $R_1$ is selected from H, F, Cl, Br, I, OH, $NH_2$, CN, $CH_3$, $CH_2F$, $CHF_2$, $CF_3$, $CH_2CH_3$, and

and other variables are as defined in the present disclosure.

In some embodiments of the present disclosure, the above-mentioned $R_3$, $R_4$ and $R_5$ are each independently selected from H, F, Cl, Br, I, OH, $NH_2$, CN, and $CH_3$ optionally substituted with 1, 2, or 3 $R_b$, and other variables are as defined in the present disclosure.

In some embodiments of the present disclosure, the above-mentioned $R_3$, $R_4$ and $R_5$ are each independently selected from H, F, Cl, Br, I, OH, $NH_2$, CN, $CH_3$, $CH_2F$, $CHF_2$ and $CF_3$, and other variables are as defined in the present disclosure.

In some embodiments of the present disclosure, the above-mentioned L is selected from single bond, —O—, and —S—, and other variables are as defined in the present disclosure.

In some embodiments of the present disclosure, the above-mentioned moiety

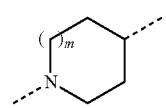

is selected from

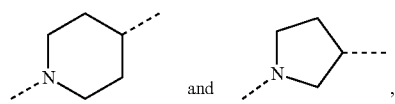

and other variables are as defined in the present disclosure.

In some embodiments of the present disclosure, the above-mentioned moiety

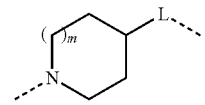

is selected from

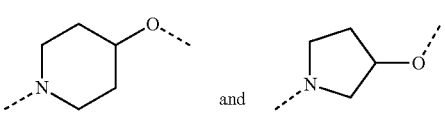

and other variables are as defined in the present disclosure.

The present disclosure also includes some embodiments that are obtained by combining any of the above-mentioned variables.

In some embodiments of the present disclosure, the above-mentioned compound, or an isomer or a pharmaceutically acceptable salt thereof is disclosed, wherein the compound is selected from

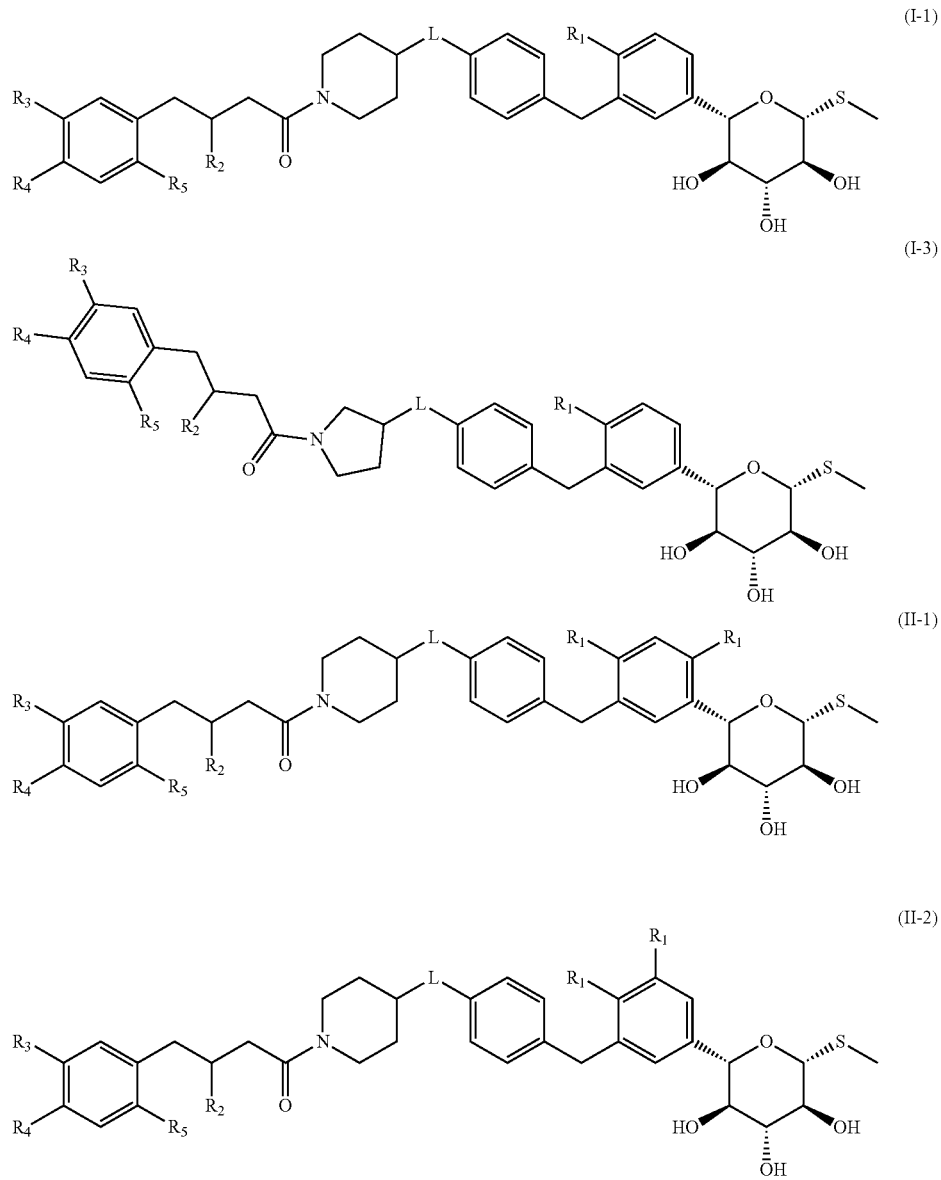
wherein
R₁, R₂, R₃, R₄, R₅ and L are as defined in the present disclosure.
In some embodiments of the present disclosure, the above-mentioned compound, or an isomer or a pharmaceutically acceptable salt thereof is disclosed, wherein the compound is selected from
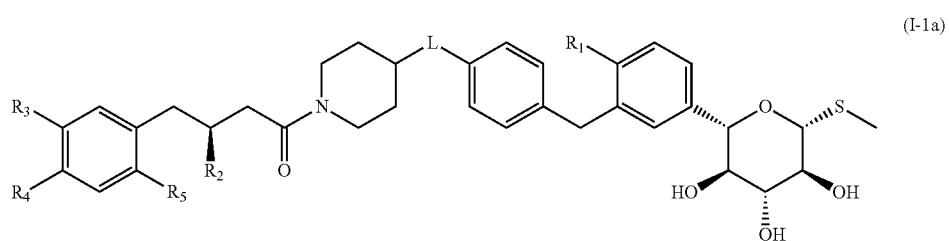

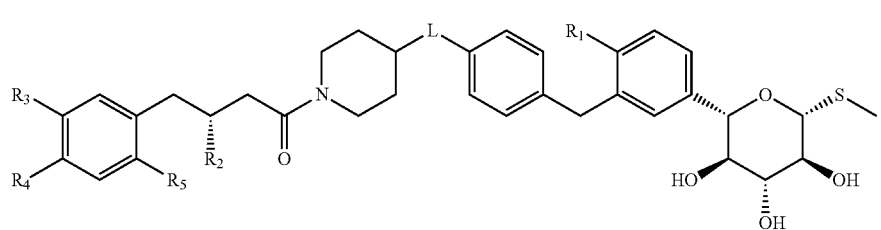
(I-1b)
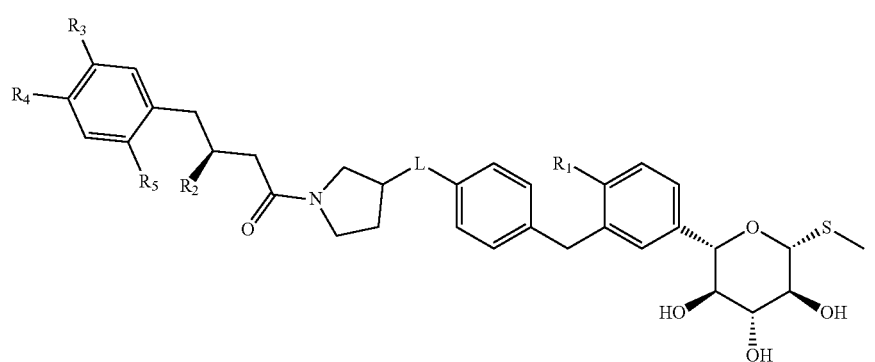
(I-3a)
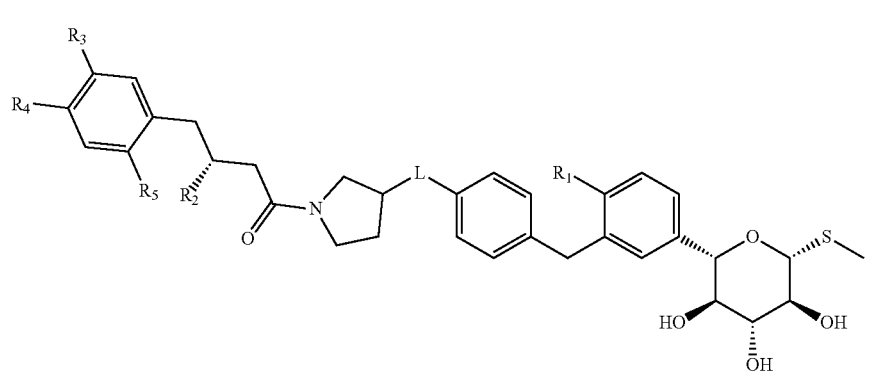
(I-3b)
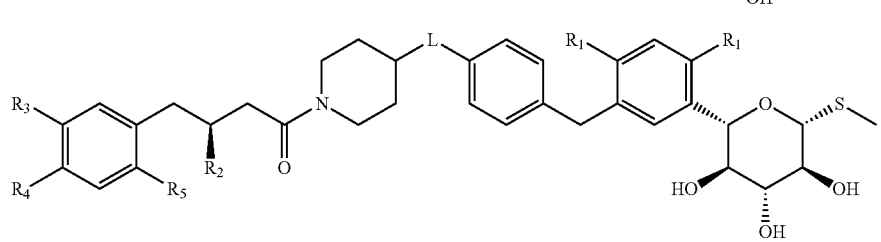
(II-1a)
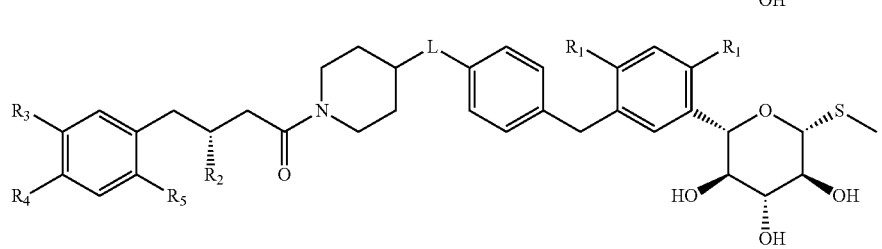
(II-1b)
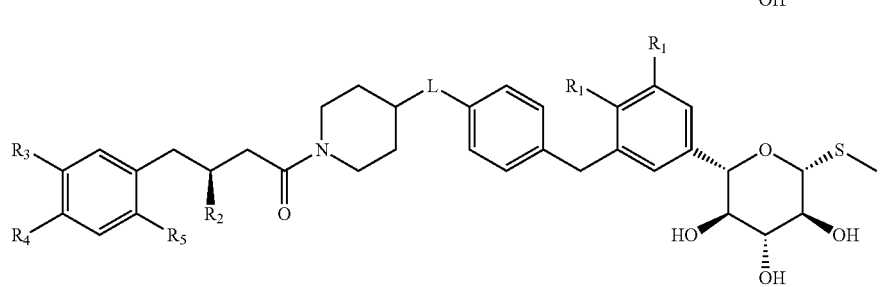
(II-2a)

-continued
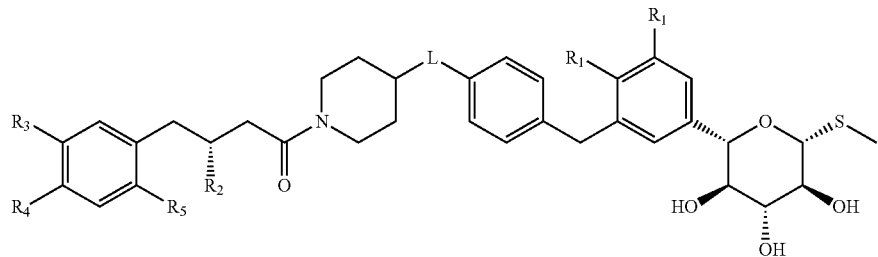
(II-2b)
wherein
R$_2$ is selected from F, Cl, Br, I, OH, NH$_2$, NH(CH$_3$), and N(CH$_3$)$_2$;
R$_1$, R$_3$, R$_4$, R$_5$ and L are as defined in the present disclosure.
In some embodiments of the present disclosure, the above-mentioned compound, or an isomer or a pharmaceutically acceptable salt thereof is disclosed, wherein the compound is selected from
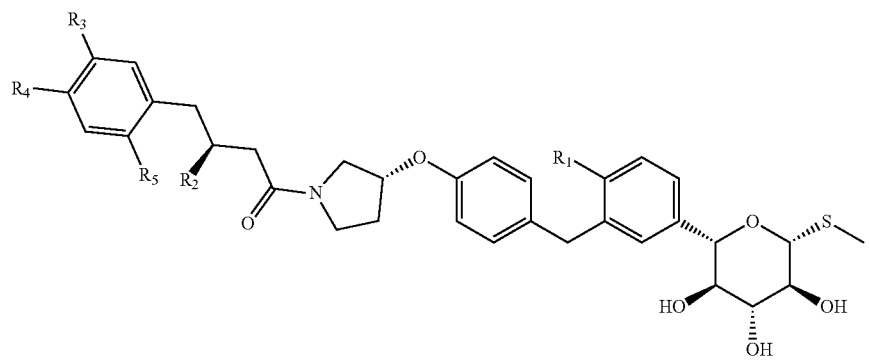
(I-3a-1)
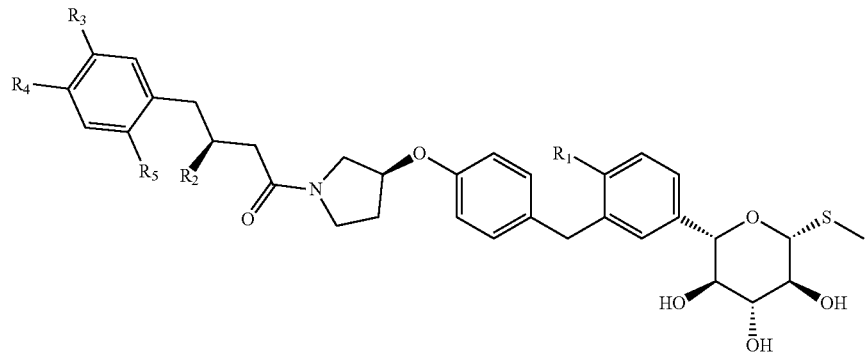
(I-3a-2)
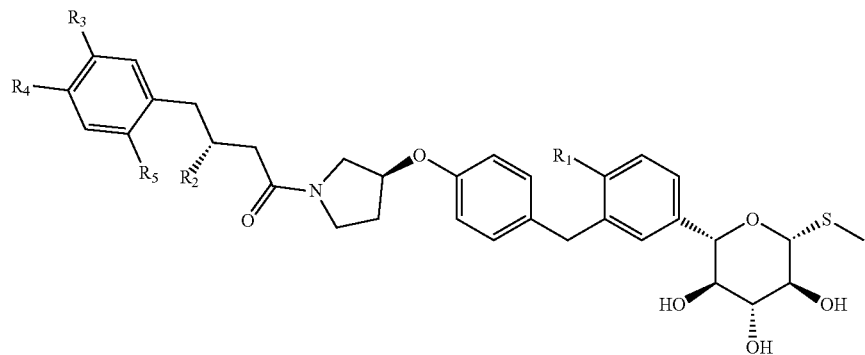
(I-3b-1)

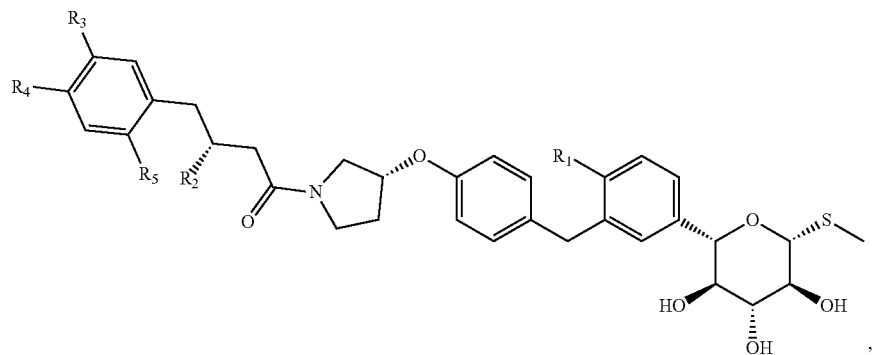
wherein,
R$_1$, R$_2$, R$_3$, R$_4$, and R$_5$ are as defined in the present disclosure.
The present disclosure also provides a compound represented by the following formula, or an isomer or a pharmaceutically acceptable salt thereof,
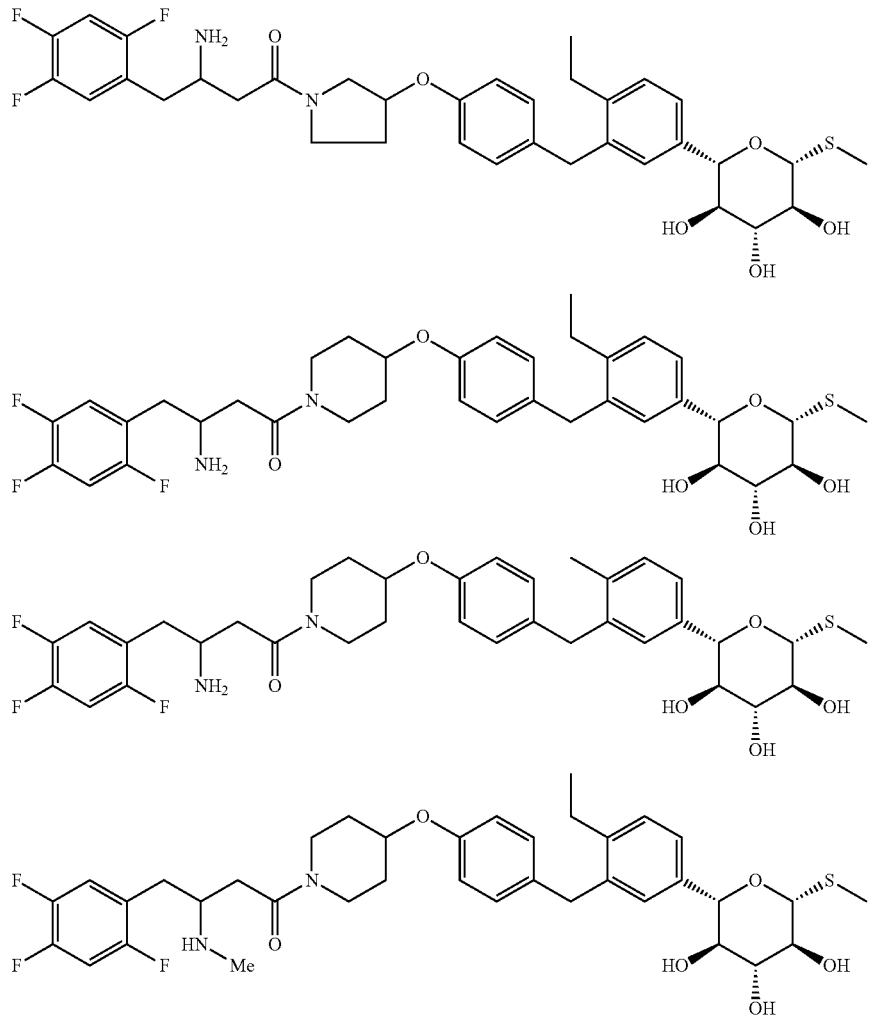

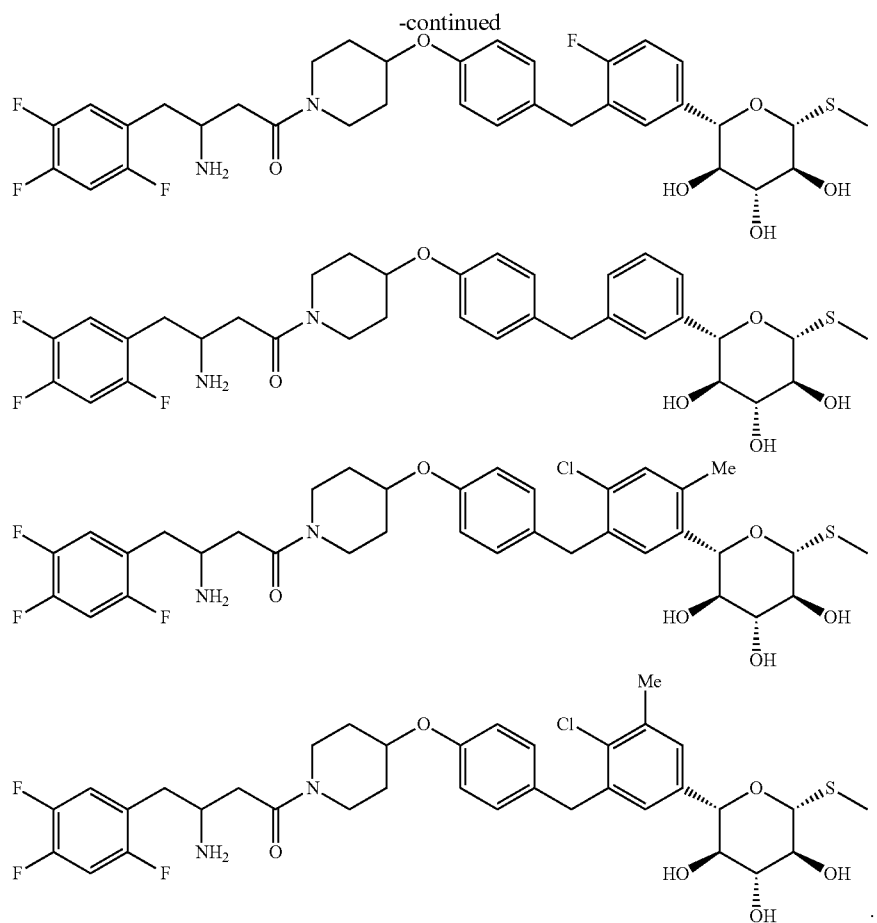
In some embodiments of the present disclosure, the above-mentioned compound, or an isomer or a pharmaceutically acceptable salt thereof is disclosed, wherein the compound is selected from
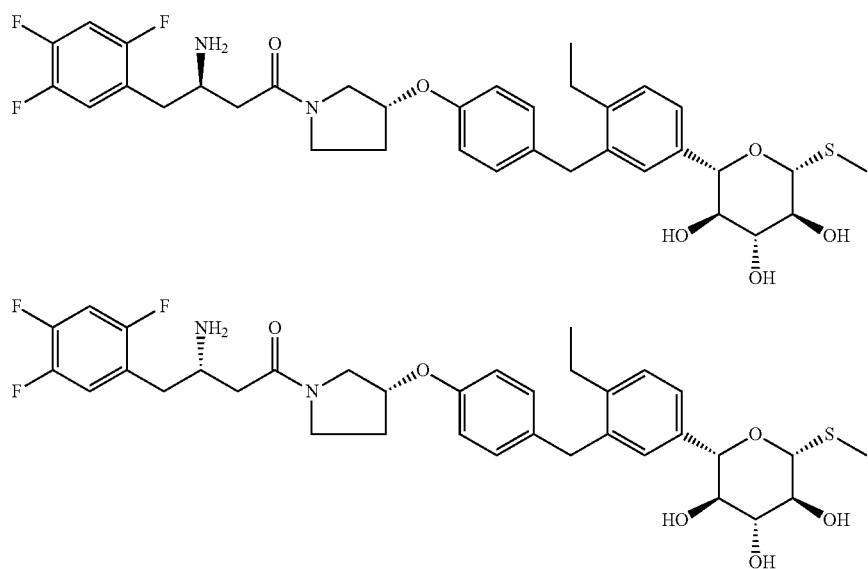

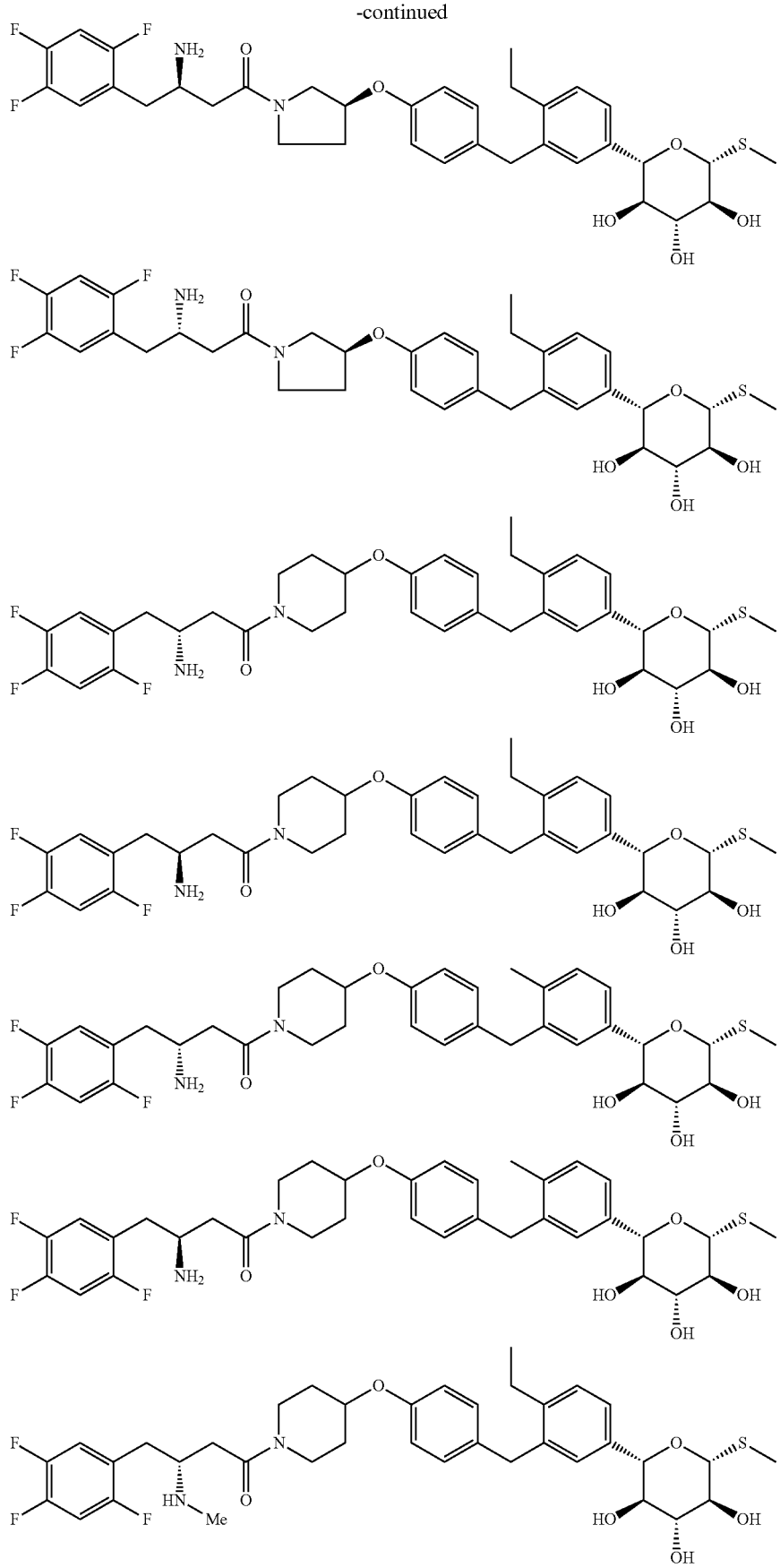

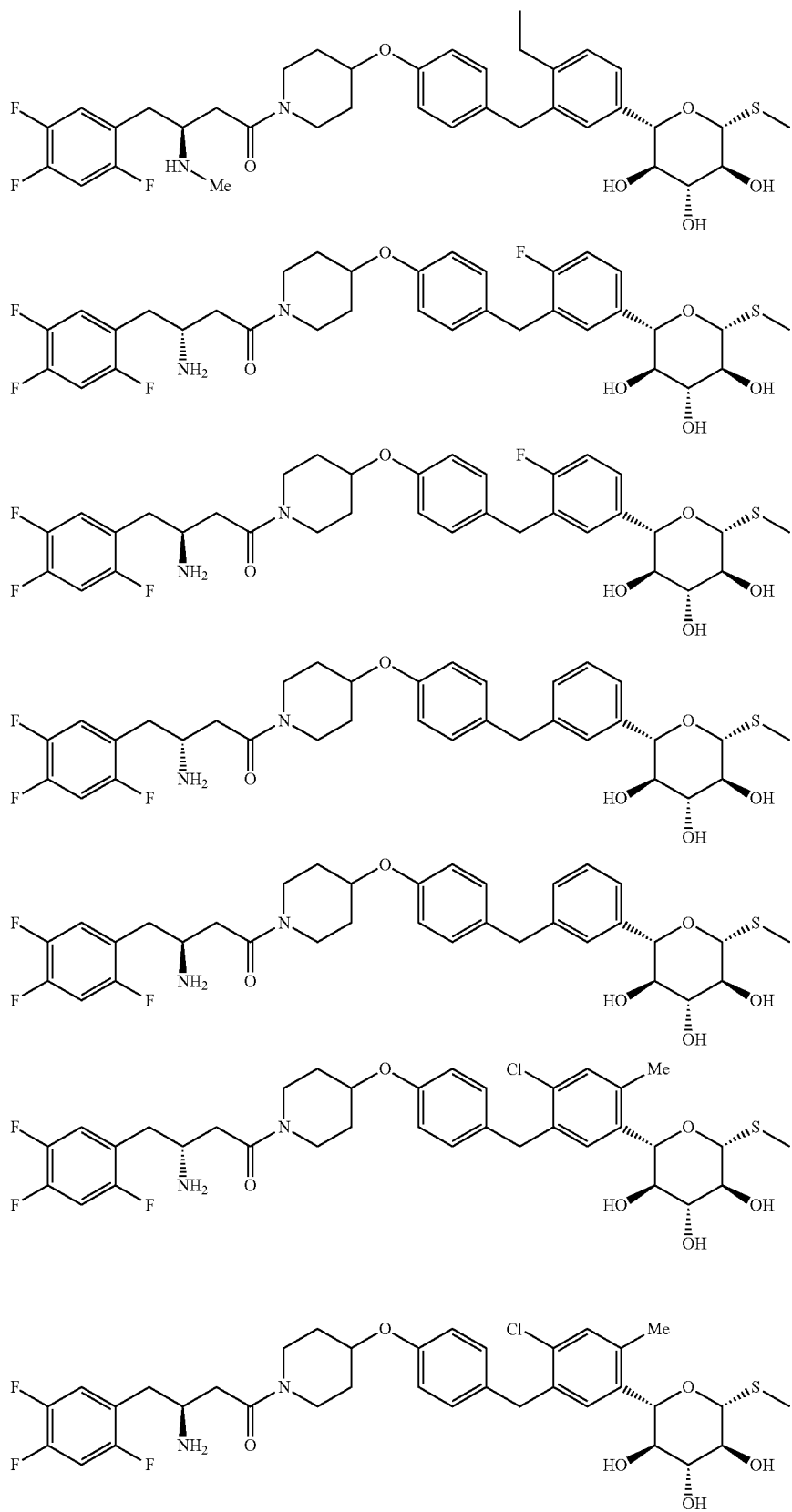

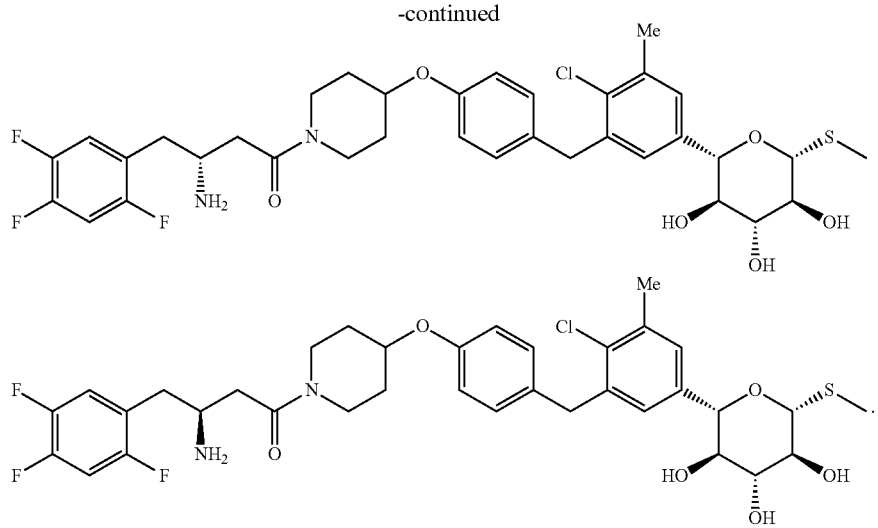

The present disclosure also provides a pharmaceutical composition comprising a therapeutically effective amount of the above-mentioned compound, or an isomer or a pharmaceutically acceptable salt thereof as an active ingredient, and a pharmaceutically acceptable carrier.

In some embodiments of the present disclosure, disclosed herein is the use of the above-mentioned compound, or an isomer or a pharmaceutically acceptable salt thereof, or the above-mentioned composition in the manufacture of a medicament for the treatment of a disease associated with SGLT1.

In some embodiments of the present disclosure, disclosed is the above-mentioned use, which is characterized in that the medicament for the treatment of a disease associated with SGLT1 is a drug for diabetes and obesity.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

In addition to the salt form, the compound provided herein also exists in prodrug form. The prodrug of the compound described herein is the compound that readily undergoes chemical change under physiological condition to be converted into the compound disclosed herein. Additionally, the prodrug can be converted to the compound disclosed herein by a chemical or biochemical method in vivo environment.

Certain compounds disclosed herein can exist in an unsolvated form or a solvated form, including a hydrated form. Generally, the solvated form is equivalent to the unsolvated form, and both are encompassed within the scope disclosed herein.

Unless otherwise specified, the term "isomer" is intended to include geometric isomer, cis- and trans-isomer, stereoisomer, enantiomer, optical isomer, diastereomer, and tautomer.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer in which two or more chiral centers of are contained in a molecule and is in a non-mirrored relationship between molecules.

Unless otherwise specified, "(D)" or "(+)" means dextroisomer, "(L)" or "(−)" means levoisomer, and "(DL)" or "(±)" means racemate.

Unless otherwise specified, a wedged solid bond ( ⭑ ) and a wedged dashed bond ( ⭑ ) indicate the absolute configuration of a stereocenter; a straight solid bond ( ⭑ ) and a straight dashed bond ( ⭑ ) indicate the relative configuration of a stereocenter; a wavy line ( ⭑ ) indicates a wedged solid bond ( ⭑ ) or a wedged dashed bond ( ⭑ ); or a wavy line ( ⭑ ) indicates a straight solid bond ( ⭑ ) and a straight dashed bond ( ⭑ ).

The compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2,4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" refers to the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of a certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereomer are generally isolated through chromatography which uses a chiral stationary phase and optionally combines with a chemical derivative method (for example, carbamate generated from amine).

The compounds disclosed herein may contain an unnatural proportion of atomic isotopes at one or more of the atoms that make up the compounds. For example, a compound may be labeled with a radioisotope such as tritium ($^3H$), iodine-125 ($^{125}I$) or C-14 ($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom (s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When the number of a substituent is 0, it means that the substituent does not exist. For example, -A-(R)$_0$ means that the structure is actually -A.

When a substituent is vacant, it means that the substituent does not exist. For example, when X in A-X is vacant, it means that the structure is actually A.

When one of the variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X in A-X is vacant, the structure of A-X is actually A. When an enumerative substituent does not indicate through which atom it is linked to the substituted group, such substituent can be bonded through any of its atoms. For example, a pyridyl group as a substituent may be linked to the substituted group through any one of carbon atoms on the pyridine ring.

When an enumerative linking group does not indicate its linking direction, its linking direction is arbitrary. For example, when the linking group L in

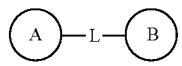

is -M-W—, the -M-W— can be linked to the ring A and the ring B in the same direction as the reading order from left to right to constitute

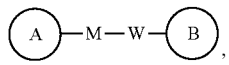

or can be linked to the ring A and the ring B in the reverse direction as the reading order from left to right to constitute

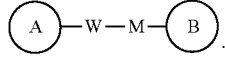

A combination of the linking groups, substituents and/or variants thereof is allowed only when such combination can result in a stable compound.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atom(s) is connected to the chemical bond, the number of H atom(s) at this site will correspondingly decrease as the number of the connected chemical bond increases, and the group will become a group of corresponding valence. The chemical bond between the site and other groups can be represented by a straight solid bond (∕), a straight dashed bond (∕), or a wavy line

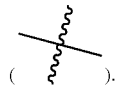

For example, the straight solid bond in —OCH$_3$ indicates that the group is connected to other groups through the oxygen atom in the group; the straight dashed bond in

indicates that the group is connected to other groups through two ends of the nitrogen atom in the group; the wavy line in

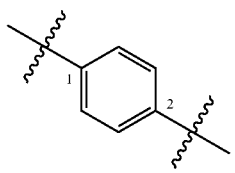 [SMILES: *c1ccc(*)cc1]

indicates that the group is connected to other groups through the 1- and 2-carbon atoms in the phenyl group;

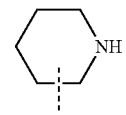

indicates that any connectable site on the piperidinyl group can be connected to other groups through one chemical bond, including at least four connection ways

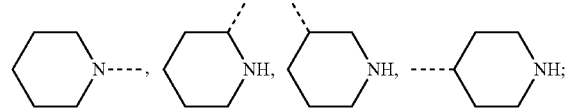

and
even if a H atom is drawn on —N—,

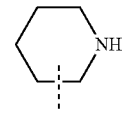

still includes the connection way of

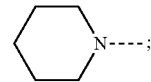

it's just that when one chemical bond is connected, the H at this site will be reduced by one, and the group will become the corresponding monovalent piperidinyl group.

Unless otherwise specified, the term "$C_{1-6}$ alkyl" is used to indicate a linear or branched saturated hydrocarbon group consisting of 1 to 6 carbon atoms. The $C_{1-6}$ alkyl group includes $C_{1-5}$, $C_{1-4}$, $C_{1-3}$, $C_{1-2}$, $C_{2-6}$, $C_{2-4}$, $C_6$, and $C_5$ alkyl groups, and the like. It may be monovalent (e.g., methyl), divalent (e.g., methylene) or multivalent (e.g., methenyl). Examples of $C_{1-6}$ alkyl groups include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "$C_{1-3}$ alkyl" is used to indicate a linear or branched saturated hydrocarbon group consisting of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methenyl). Examples of $C_{1-3}$ alkyl groups include, but are not limited to, methyl (Me), ethyl (Et), propyl (including n-propyl and isopropyl), and the like.

Unless otherwise specified, the term "$C_{1-6}$ alkoxy" means alkyl groups containing 1 to 6 carbon atoms and attached to the remainder of a molecule by an oxygen atom. The $C_{1-6}$ alkoxy group includes $C_{1-4}$, $C_{1-3}$, $C_{1-2}$, $C_{2-6}$, $C_{2-4}$, $C_6$, $C_5$, $C_4$, and $C_3$ alkoxy groups, and the like. Examples of $C_{1-6}$ alkoxy groups include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopropoxy and neopentoxy), hexyloxy, and the like.

Unless otherwise specified, the term "$C_{1-3}$ alkoxy" means alkyl groups containing 1 to 3 carbon atoms and attached to the remainder of a molecule by an oxygen atom. The $C_{1-3}$ alkoxy group includes $C_{1-2}$, $C_{2-3}$, $C_3$, and $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, the term "$C_{1-3}$ alkylamino" means alkyl groups containing 1 to 3 carbon atoms and attached to the remainder of a molecule by an amino group. The $C_{1-3}$ alkylamino group includes $C_{1-2}$, $C_3$ and $C_2$ alkylamino groups and the like. Examples of $C_{1-3}$ alkylamino groups include, but are not limited to —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, and the like.

Unless otherwise specified, $C_{n-n+m}$ or $C_n$-$C_{n+m}$ includes any one of n to n+m carbons. For example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$. $C_{n-n+m}$ or $C_n$-$C_{n+m}$ also includes any range of n to n+m. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, and the like. Similarly, the n-membered to n+m-membered ring means that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. The n-membered to n+m-membered ring also means that the number of atoms on the ring includes any range from n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The alternative embodiment includes, but is not limited to the embodiment disclosed herein.

The structures of the compounds of the present disclosure can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

All the solvents used in the present disclosure are commercially available. The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butoxycarbonyl, which is an amino protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; LiHMDS represents lithium hexamethyldisilazide; Xantphos represents 4,5-bis(diphenylphosphino)-9,9-dimethylxanthene; LiAlH$_4$ represents lithium aluminum hydride; Pd$_2$(dba)$_3$ represents tris(dibenzylideneacetone)dipalladium; Pd(dppf)Cl$_2$ represents [1,1'-bis(diphenylphosphino)ferrocene]dichloropalladium; Pd(PPh$_3$)$_4$ represents tetrakis(triphenylphosphine)palladium; IPA represents isopropyl alcohol; and DEA represents diethylamine.

Compounds are named according to general naming principles in the art or by ChemDraw® software, and commercially available compounds are named with their vendor directory names.

Technical Effects

The compound of the present disclosure has significant Human-SGLT1 and Human-SGLT2 inhibitory activities in vitro. Moreover, the compound of the present disclosure has low oral exposure and bioavailability, and functions in gastrointestinal tract, showing desirable pharmacokinetic properties as a selective SGLT1 inhibitor; the compound of the present disclosure can significantly reduce the level of blood glucose AUC of an animal within 2 hours in an animal oral glucose tolerance assay; the compound of the present disclosure can significantly reduce blood glucose and glycosylated hemoglobin of an animal after 6 hours of fasting and effectively control the increase of animal weight in an assay of diabetic animal induced by STZ combined with high-sugar and high-fat diet; and the compound of the present disclosure can significantly reduce animal weight in a dose-dependent manner, and reduce the blood glucose of an animal after 6 hours of fasting and 1 hour after meal in an assay of obese animal induced by high-sugar and high-fat diet.

Figure 1:
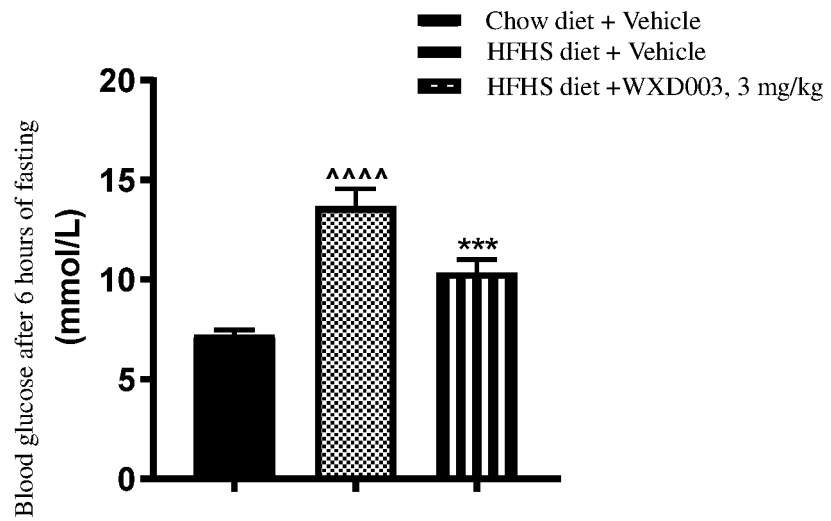
FIG. 1 shows the blood glucose level of animals after 4 weeks of administration.

Note: ^^^^ means $p<0.0001$ relative to vehicle group with chow diet, * means $p<0.05$ relative to vehicle group with high-sugar and high-fat diet,  means $p<0.01$ relative to vehicle group with high-sugar and high-fat diet, * means $p<0.001$ relative to vehicle group with high-sugar and high-fat diet, and **** means $p<0.0001$ relative to vehicle group with high-sugar and high-fat diet.

DETAILED DESCRIPTION OF THE INVENTION

The present disclosure is described in detail below by means of examples. However, it is not intended that these examples have any disadvantageous limitations to the present disclosure. The present disclosure has been described in detail herein, and the embodiments are also disclosed herein. It will be apparent to those skilled in the art that various changes and modifications may be made to the embodiments disclosed herein without departing from the spirit and scope disclosed herein.

Reference Example 1: Fragment A-1

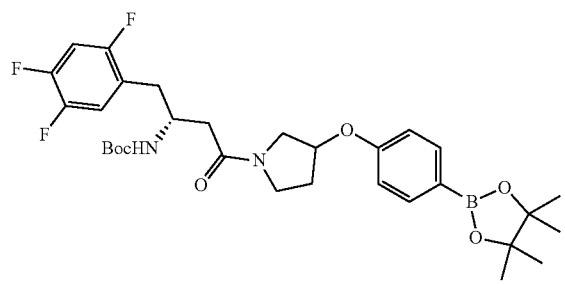 [SMILES: CC(C)(C)OC(=O)N[C@@H](CC(=O)N1CCC(Oc2ccc(B3OC(C)(C)C(C)(C)O3)cc2)C1)Cc1cc(F)c(F)cc1F]

Route of Synthesis

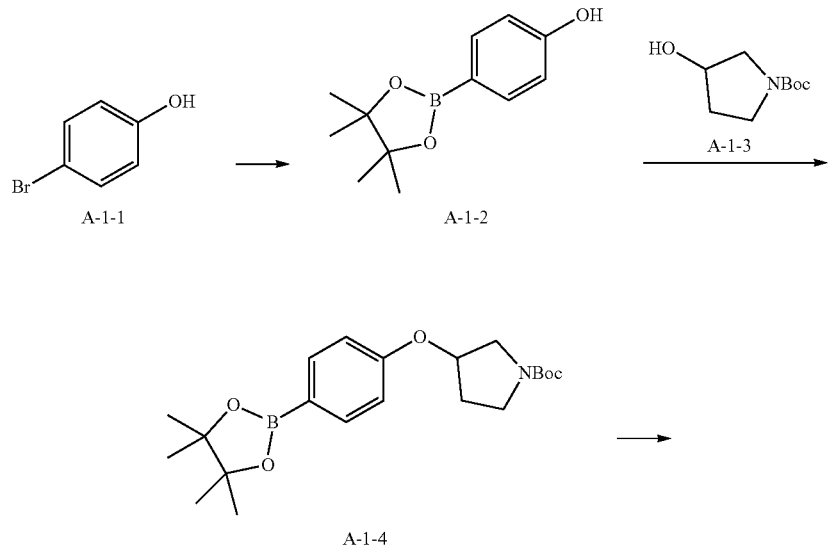

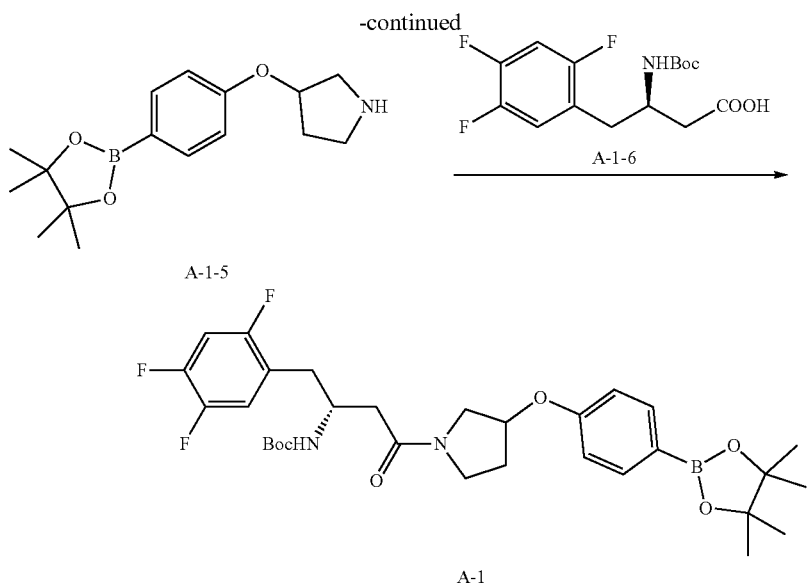

Step 1: Synthesis of the Compound A-1-2

To a reaction flask were added successively compound A-1-1 (10 g, 57.80 mmol, 1 eq), bis(pinacolato)diboron (16.15 g, 63.58 mmol, 1.1 eq), Pd(dppf)Cl$_2$ (4.23 g, 5.78 mmol, 0.1 eq), KOAc (17.02 g, 173.40 mmol, 3 eq), and dioxane (120 mL), and the atmosphere was replaced with nitrogen. The mixture was reacted at 100° C. for 2 h. After the reaction was completed, the reaction solution was diluted with 50 mL of water, and extracted with ethyl acetate (50 mL*3). The combined organic phase was washed with 50 mL of saturated brine, dried over anhydrous sodium sulfate, and filtered, and the organic phase was rotary-evaporated to dryness under reduced pressure to give a crude product. The crude product was purified by column chromatography (PE:EA=50:1) to give A-1-2. $^1$H NMR (400 MHz, CDCl$_3$) δ ppm 7.72 (d, J=8.4 Hz, 2H), 6.83 (d, J=8.4 Hz, 2H), 5.40 (s, 1H), 1.34 (s, 12H).

Step 2: Synthesis of the Compound A-1-4

To a reaction flask were added triphenylphosphine (7151 mg, 27.3 mmol, 1.2 eq), DIAD (5513 mg, 27.3 mmol, 1.2 eq), and THF (40 mL). A-1-3 (5104.7 mg, 27.3 mmol, 1.2 eq) and A-1-2 (5 g, 22.7 mmol, 1 eq) dissolved in THF (40 mL) were then added, and the mixture was reacted at 25° C. for 16 hours. After the reaction was completed, the reaction solution was diluted with 100 mL of water, and extracted with ethyl acetate (100 mL*3). The combined organic phase was dried over anhydrous sodium sulfate, and filtered, and the organic phase was rotary-evaporated to dryness to give a crude product. The crude product was purified by column chromatography (PE:EA=19:1-9:1) to give A-1-4. $^1$H NMR (400 MHz, CDCl$_3$) δ ppm 7.72-7.75 (m, 2H), 6.84-6.90 (m, 2H), 4.94 (s, 1H), 3.43-3.69 (m, 4H), 2.07-2.23 (m, 2H), 1.47 (s, 9H), 1.34 (s, 12H).

Step 3: Synthesis of the Compound A-1-5

To a reaction flask were added A-1-4 (1.28 g, 3.29 mmol, 1 eq), EtOAc (10 mL), and hydrogen chloride/EtOAc (4 M, 9.04 mL, 11 eq), and the mixture was stirred at 25° C. for 3 hours. After the reaction was completed, the reaction solution was rotary-evaporated to dryness to give a crude product A-1-5. The crude product A-1-5 was directly used in the next reaction.

Step 4: Synthesis of the Compound A-1

To a reaction flask were added A-1-5 (1.37 g, 4.74 mmol, 1 eq), A-1-6 (1.58 g, 4.74 mmol, 1 eq), HATU (1.80 g, 4.74 mmol, 1 eq), THF (15 mL), and DIEA (612.29 mg, 4.74 mmol, 825.18 μL, 1 eq), and the mixture was stirred at 25° C. for 2.5 hours. After the reaction was completed, the reaction solution was diluted with 20 mL of water, and extracted with ethyl acetate (20 mL*3). The combined organic phase was dried over anhydrous sodium sulfate, and filtered. The filtrate was rotary-evaporated to dryness to give a crude product. The crude product was purified by column chromatography (PE:EA=3:2) to give A-1. $^1$H NMR (400 MHz, CDCl$_3$) δ ppm 7.70-7.81 (m, 2H), 7.01-7.13 (m, 1H), 6.81-6.93 (m, 3H), 5.69-5.93 (m, 1H), 4.93-5.06 (m, 1H), 3.48-3.89 (m, 4H), 2.83-3.02 (m, 2H), 2.45-2.61 (m, 2H), 2.21-2.36 (m, 1H), 2.06-2.21 (m, 1H), 1.29-1.41 (m, 21H).

Referring to the synthesis method of steps 2 to 4 in Reference example 1, fragment A-2 was synthesized.

Reference Example 2: Fragment A-2

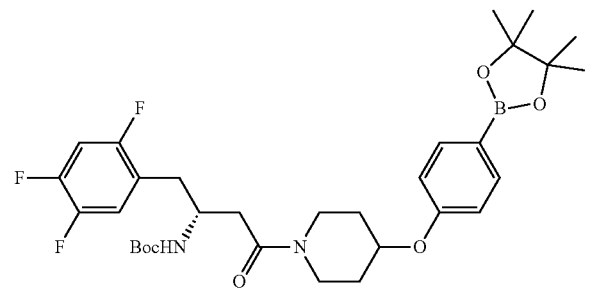 [SMILES: CC(C)(C)OC(=O)N[C@@H](CC(=O)N1CCC(Oc2ccc(B3OC(C)(C)C(C)(C)O3)cc2)CC1)Cc1cc(F)c(F)cc1F]

Route of Synthesis
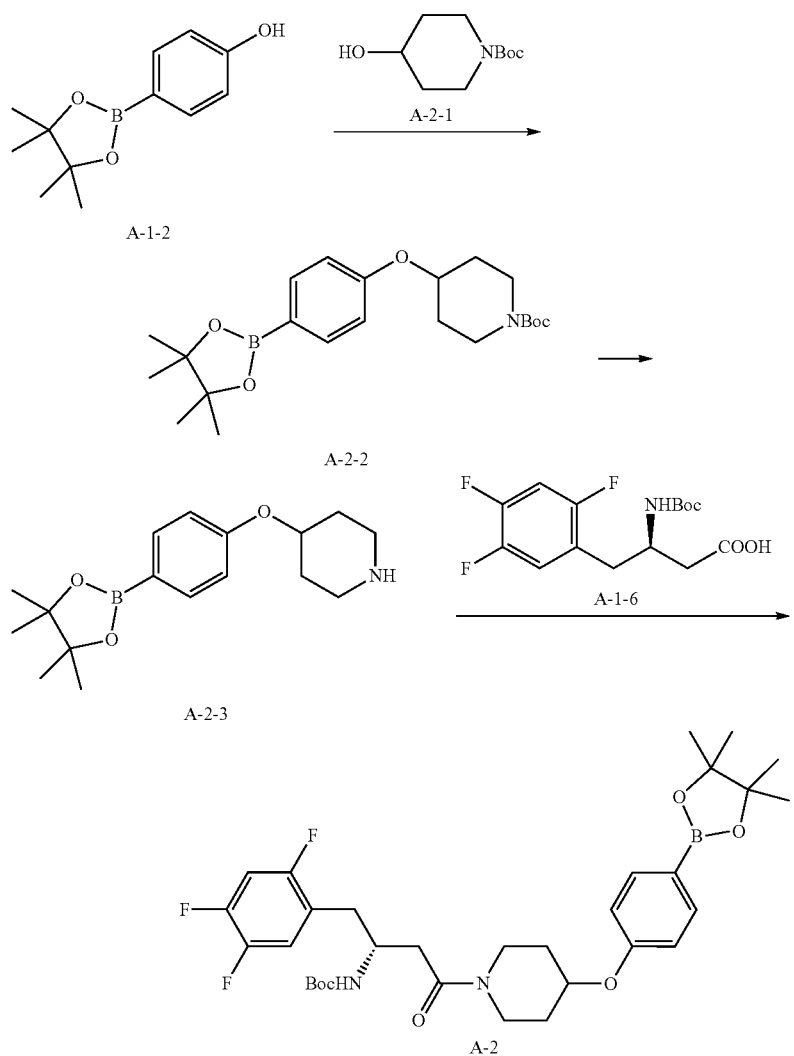
Compound A-2:
$^1$H NMR (400 MHz, CDCl$_3$) δ ppm 1.33 (s, 12H), 1.37 (d, J=1.76 Hz, 9H), 1.77-1.95 (m, 4H), 2.50-2.65 (m, 2H), 2.86-3.01 (m, 2H), 3.31-3.44 (m, 1H), 3.56-3.84 (m, 3H), 4.06-4.16 (m, 1H), 4.56-4.70 (m, 1H), 5.66 (br d, J=7.53 Hz, 1H), 6.86-6.93 (m, 3H), 7.04-7.12 (m, 1H), 7.76 (d, J=8.28 Hz, 2H).
Reference Example 3: Fragment A-3
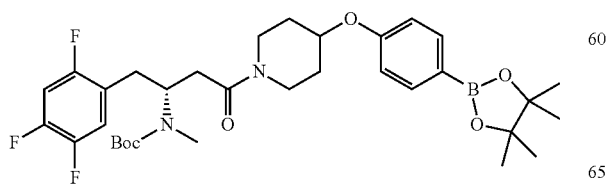

Route of Synthesis

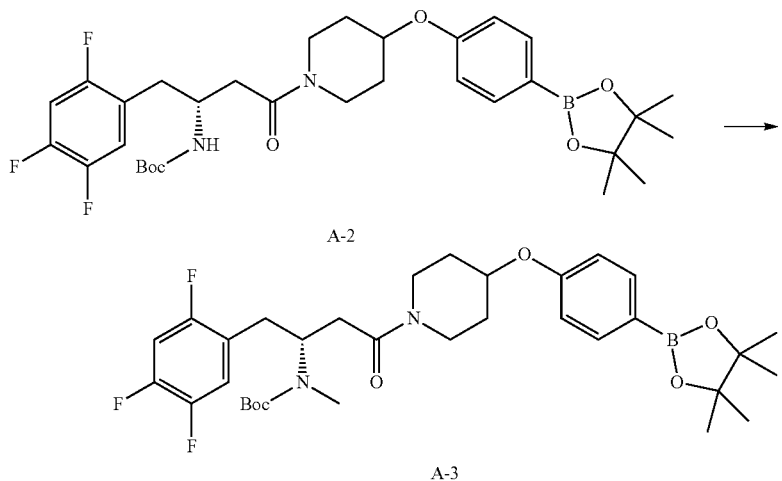

Step 1: Synthesis of the Compound A-3

To a reaction flask were added the compound A-2 (0.20 g, 323.37 μmol, 1 eq) and anhydrous N,N-dimethylformamide (3 mL). Sodium hydride (30 mg, 750.00 μmol, 60% purity, 2.32 eq) was added at 0° C. The mixture was stirred at 0° C. for 0.5 hours, and methyl iodide (0.15 g, 1.06 mmol, 65.79 μL, 3.27 eq) was then added. The reaction system was stirred at 20° C. for 2 hours. The reaction solution was concentrated to give a crude product. Water (10 mL) was added to the crude product, and the mixture was extracted three times with ethyl acetate (10 mL each time). The organic phases were combined, washed with saturated brine (10 mL), dried over anhydrous sodium sulfate, and filtered. The filtrate was concentrated to give the compound A-3. The crude product A-3 was directly used in the next reaction.

Reference Example 4: Fragment B-1

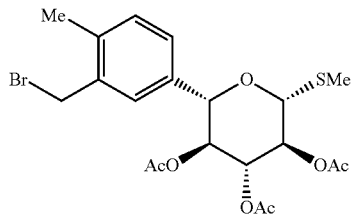 [SMILES: CS[C@H]1O[C@@H](c2ccc(C)c(CBr)c2)[C@H](OC(C)=O)[C@@H](OC(C)=O)[C@@H]1OC(C)=O]

Route of Synthesis

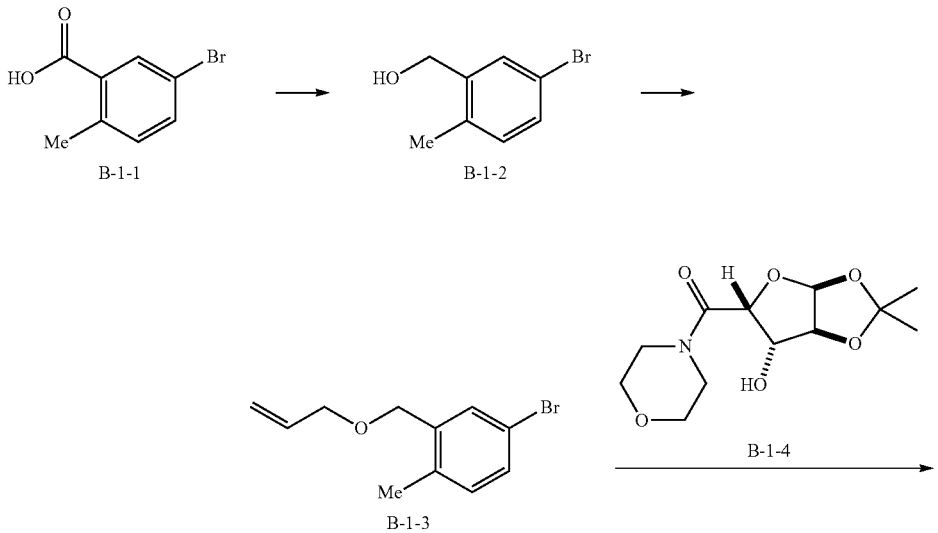

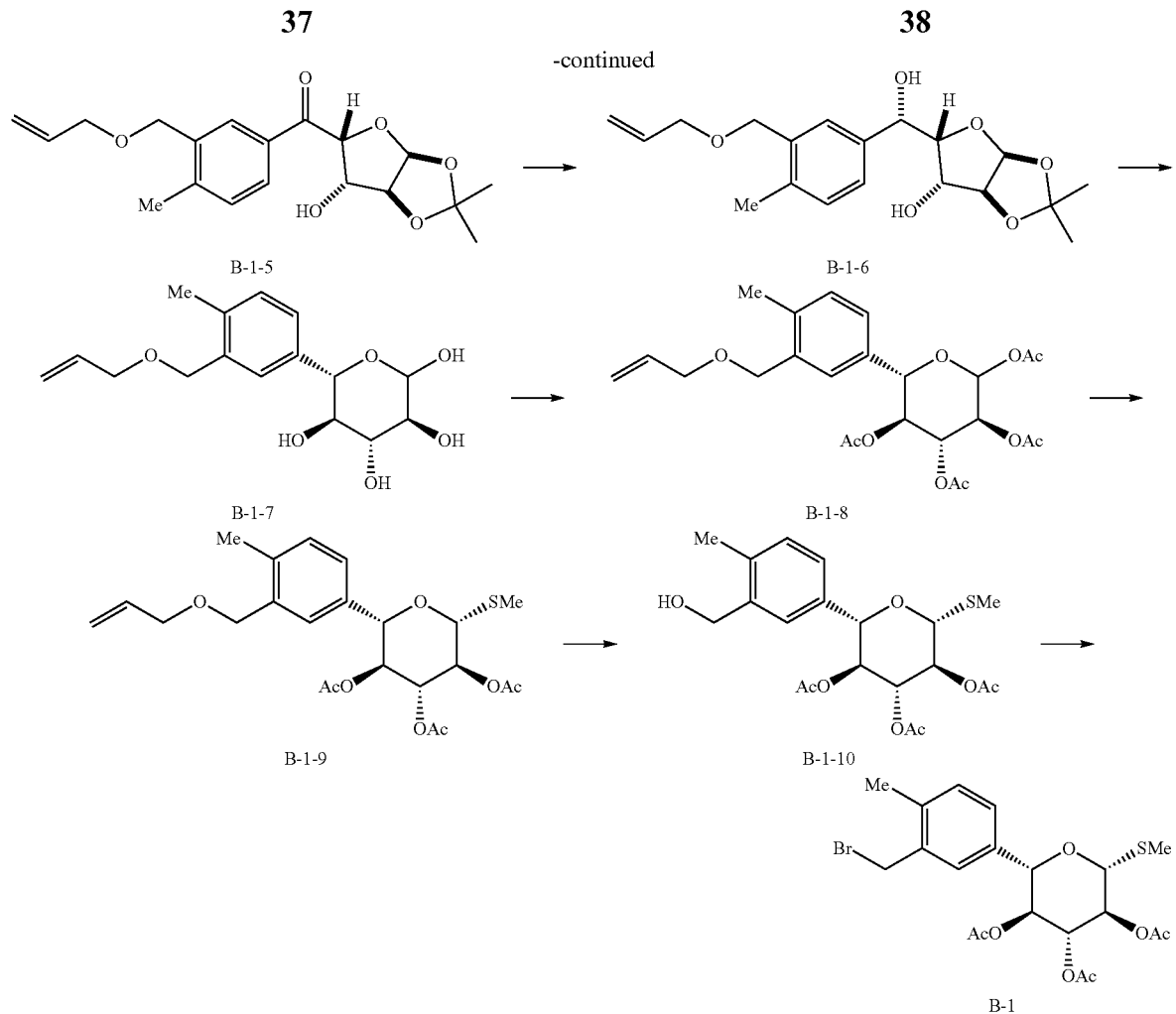

Step 1: Synthesis of the Compound B-1-2

Lithium aluminum hydride (11 g, 289.82 mmol, 1.25 eq) was dissolved in tetrahydrofuran (200 mL) at 0° C. The atmosphere was replaced with nitrogen three times, and finally filled with nitrogen for protection. Compound B-1-1 (50 g, 232.51 mmol, 1 eq) was dissolved in tetrahydrofuran (200 mL), and slowly added to the reaction solution at 0° C. Generated bubbles were observed. The reaction was heated to 25° C. for 2 hours. At 0° C., water (11 mL) was slowly added dropwise, then 15% aqueous sodium hydroxide solution (11 mL) was added dropwise, and finally water (33 mL) was added. The mixture was filtered, and the filter residue was washed twice with ethyl acetate. The filtrate was rotary-evaporated to dryness to give the crude compound B-1-2.

Step 2: Synthesis of the Compound B-1-3

Compound B-1-2 (47.9 g, 238.24 mmol, 1 eq) was dissolved in dimethylformamide (120 mL), and sodium hydride (14.29 g, 357.36 mmol, 60% purity, 1.5 eq) was added at 0° C. The mixture was stirred at 25° C. for 0.5 hours. 3-Bromopropene (57.64 g, 476.47 mmol, 41.17 mL, 2 eq) was slowly added to the reaction solution, and the mixture was reacted at 25° C. for another 2 hours. After the reaction was completed, the reaction was quenched with water (50 mL) at 0° C., and extracted with ethyl acetate (500 mL*2). The organic phase was washed with water (50 mL*2) followed by saturated brine (50 mL*2), and dried over anhydrous sodium sulfate. The crude product was purified by column chromatography to give the title compound B-1-3. The product was confirmed by LCMS, LC-MS (m/z) 263, 265 [M+Na]$^+$.

Step 3: Synthesis of the Compound B-1-5

Compound B-1-3 (18.5 g, 76.72 mmol, 1.2 eq) was dissolved in tetrahydrofuran (100 mL) at −78° C., and n-butyl lithium (2.5 M, 33.25 mL, 1.3 eq) was added under nitrogen. The mixture was reacted at −78° C. for 0.5 hours. At the same time, compound B-1-4 (17.47 g, 63.93 mmol, 1 eq) was dissolved in tetrahydrofuran (100 mL). The mixture was cooled to 0° C. and purged with nitrogen. Tert-butyl magnesium chloride (1.7 M, 41.37 mL, 1.1 eq) was then added, and the mixture was reacted at 0° C. for 0.5 hours. The solution of magnesium alkoxy was slowly added to the solution of alkyl lithium at −78° C. The reaction solution was reacted at −78° C. for 0.5 hours, and then heated to 25° C. and reacted for another 15.5 hours. After the reaction was completed, a solution of ammonium chloride (50 mL) was added to the reaction solution at 0° C. The reaction solution was diluted with ethyl acetate (200 mL), and then washed with water (50 mL*2). The organic phases were combined, washed with saturated brine (50 mL*2) to remove water, dried over anhydrous sodium sulfate, and filtered. The filtrate was rotary-evaporated to dryness. The crude product was purified by column chromatography to give the title compound B-1-5. The product was confirmed by LCMS, LC-MS (m/z) 371 [M+Na]$^+$.

Step 4: Synthesis of the Compound B-1-6

Compound B-1-5 (17.80 g, 51.09 mmol, 1 eq) was dissolved in methanol (100 mL), and the solution was cooled to 0° C. Cerium trichloride heptahydrate (22.84 g, 61.31 mmol, 5.83 mL, 1.2 eq), and then sodium borohydride (3.87 g, 102.18 mmol, 2 eq) were added. The mixture was heated to 25° C. and reacted for 16 hours. After the reaction was completed, the reaction solution was quenched with water (30 mL), and rotary-evaporated to dryness. The residue was diluted with ethyl acetate (100 mL), washed with water (50 mL*2), then washed with saturated brine (50 mL*2) to remove water, finally dried over anhydrous sodium sulfate, and filtered. The filtrate was concentrated to dryness under reduced pressure to give the title compound B-1-6. The product was confirmed by LCMS, LC-MS (m/z) 373 [M+Na]$^+$.

Step 5: Synthesis of the Compound B-1-7

Compound B-1-6 (10.22 g, 29.17 mmol, 1 eq) was dissolved in water (100 mL) and glacial acetic acid (100 mL), and the mixture was reacted at 100° C. for 16 hours. After the reaction was completed, the mixture was rotary evaporated to dryness at 60° C. under vacuum, and then striped three times with toluene to give compound B-1-7. The product was confirmed by LCMS, LC-MS (m/z) 333 [M+Na]$^+$.

Step 6: Synthesis of the Compound B-1-8

Compound B-1-7 (9.52 g, 30.68 mmol, 1 eq) and acetic anhydride (25.05 g, 245.41 mmol, 22.98 mL, 8 eq) were dissolved in pyridine (40 mL), and the solution was stirred at 25° C. for 16 hours. After the reaction was completed, the reaction solution was diluted with ethyl acetate (200 mL), and washed with 1 M diluted hydrochloric acid (100 mL*4). The organic phase was washed with water (50 mL*2) and then saturated brine (50 mL*2), finally dried over anhydrous sodium sulfate, and filtered. The filtrate was concentrated to dryness under reduced pressure. The residue was purified by column chromatography to give the title compound B-1-8. The product was confirmed by LCMS, LC-MS (m/z) 501 [M+Na]$^+$.

Step 7: Synthesis of B-1-9

Compound B-1-8 (8.8 g, 18.39 mmol, 1 eq) was dissolved in 1,4-dioxane (100 mL), and thiourea (4.20 g, 55.17 mmol, 3 eq) was added. The atmosphere was replaced with nitrogen three times, and trimethylsilyl trifluoromethanesulfonate (14.31 g, 64.37 mmol, 3.5 eq) was added at 25° C. The mixture was heated to 60° C. and reacted for 2 hours, and then cooled to 25° C. Iodomethane (13.30 g, 93.70 mmol, 5.09 eq) and diisopropylethylamine (19.02 g, 147.13 mmol, 8 eq) were added successively. The mixture was reacted at 25° C. for 14 hours. After the reaction was completed, the reaction solution was diluted with water (80 mL), and extracted with ethyl acetate (80 mL*3). The organic phases were combined, washed with saturated brine (50 mL), dried over anhydrous sodium sulfate, and filtered. The filtrate was rotary-evaporated to dryness under reduced pressure to give a crude product. The crude product was purified by column chromatography to give the title compound B-1-9. The product was confirmed by LCMS, LC-MS (m/z) 489 [M+Na]$^+$.

Step 8: Synthesis of B-1-10

To a reaction flask were added B-1-9 (2 g, 4.29 mmol, 1 eq), barbituric acid (1.10 g, 8.57 mmol, 2 eq), and ethanol (20 mL). The atmosphere was replaced with nitrogen three times, and then tetrakis(triphenylphosphine)palladium (495.37 mg, 428.68 μmol, 0.1 eq) was added. The mixture was reacted under nitrogen at 70° C. for 16 hours. After the reaction was completed, the reaction solution was diluted with water (20 mL), and extracted with ethyl acetate (20 mL*3). The organic phases were combined, washed with saturated brine (50 mL), dried over anhydrous sodium sulfate, and filtered. The filtrate was rotary-evaporated to dryness under reduced pressure to give a crude product. The crude product was purified by column chromatography to give the title compound B-1-10. The product was confirmed by LCMS, LC-MS (m/z) 449 [M+Na]$^+$.

Step 9: Synthesis of B-1

To a reaction flask were added compound B-1-10 (1.5 g, 3.52 mmol, 1 eq), triphenylphosphine (1.38 g, 5.28 mmol, 1.5 eq), and dichloromethane (20 mL). The atmosphere was replaced with nitrogen three times, and the mixture was reacted at 25° C. for 0.5 hours. N-bromosuccinimide (938.98 mg, 5.28 mmol, 1.5 eq) was then added at 0° C., and the mixture was reacted at 25° C. for 1.5 hours. After the reaction was completed, the reaction solution was diluted with water (20 mL), and extracted with ethyl acetate (20 mL*3). The combined organic phase was dried over anhydrous sodium sulfate, and filtered. The filtrate was rotary-evaporated to dryness under reduced pressure to give a crude product. The crude product was purified by column chromatography to give the title compound B-1. $^1$H NMR (400 MHz, CDCl$_3$) δ 7.25 (d, J=6.4 Hz, 2H), 7.18 (d, J=8.4 Hz, 1H), 5.38 (t, J=9.6 Hz, 1H), 5.25 (t, J=9.6 Hz, 1H), 5.13 (t, J=9.6 Hz, 1H), 4.56 (d, J=9.6 Hz, 1H), 4.53 (q, J=10.4 Hz, 2H), 4.43 (d, J=9.6 Hz, 1H), 2.40 (s, 3H), 2.21 (s, 3H), 2.11 (s, 3H), 2.02 (s, 3H), 1.84 (s, 3H).

Referring to the synthesis method of steps 1 to 9 in Reference example 4, each fragment in Table 1 was synthesized.

TABLE 1
| Reference example | Fragment | Structure | NMR |
|---|---|---|---|
| 5 | B-2 | 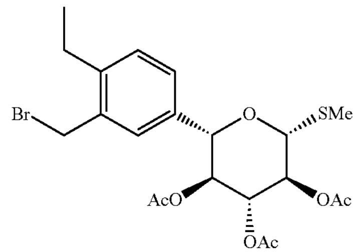 [SMILES: CCc1ccc([C@@H]2O[C@H](SC)[C@@H](OC(C)=O)[C@H](OC(C)=O)[C@H]2OC(C)=O)cc1CBr] | $^1$H NMR (400 MHz, CDCl$_3$) δ ppm 7.28 – 7.32 (m, 1 H) 7.26 (s, 1 H) 7.18 – 7.25 (m, 1 H) 5.31 – 5.41 (m, 1 H) 5.19 – 5.26 (m, 1 H) 5.12 (t, J = 9.69 Hz, 1 H) 4.47 – 4.60 (m, 3 H) 4.43 (d, J = 9.88 Hz, 1 H) 2.76 (q, J = 7.63 Hz, 2 H) 2.17 – 2.25 (m, 3 H) 2.07 – 2.14 (m, 3 H) 1.98 – 2.06 (m, 3 H) 1.80 – 1.90 (m, 3 H) 1.28 (t, J = 7.57 Hz, 3 H). |
| 6 | B-3 | 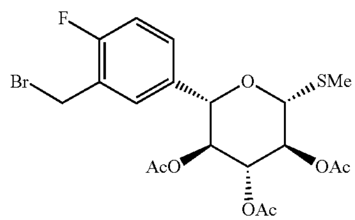 [SMILES: CS[C@H]1O[C@@H](c2ccc(F)c(CBr)c2)[C@H](OC(C)=O)[C@@H](OC(C)=O)[C@@H]1OC(C)=O] | $^1$H NMR (400 MHz, CDCl$_3$) δ ppm 7.29 – 7.40 (m, 2 H), 7.06 (t, J = 8.9 Hz, 1 H), 5.32 – 5.39 (m, 1 H), 5.22 (t, J = 9.7 Hz, 1 H), 5.07 (t, J = 9.7 Hz, 1 H), 4.50 – 4.60 (m, 2 H), 4.40 – 4.48 (m, 2 H), 2.21 (s, 3 H), 2.10 (s, 3 H), 2.02 (s, 3 H), 1.85 (s, 3 H). |
Reference Example 7: Fragment B-4
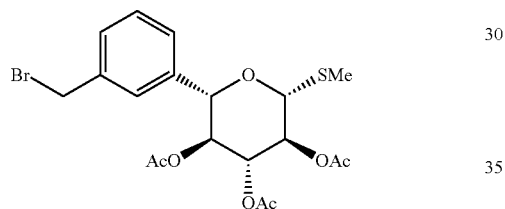
Route of Synthesis
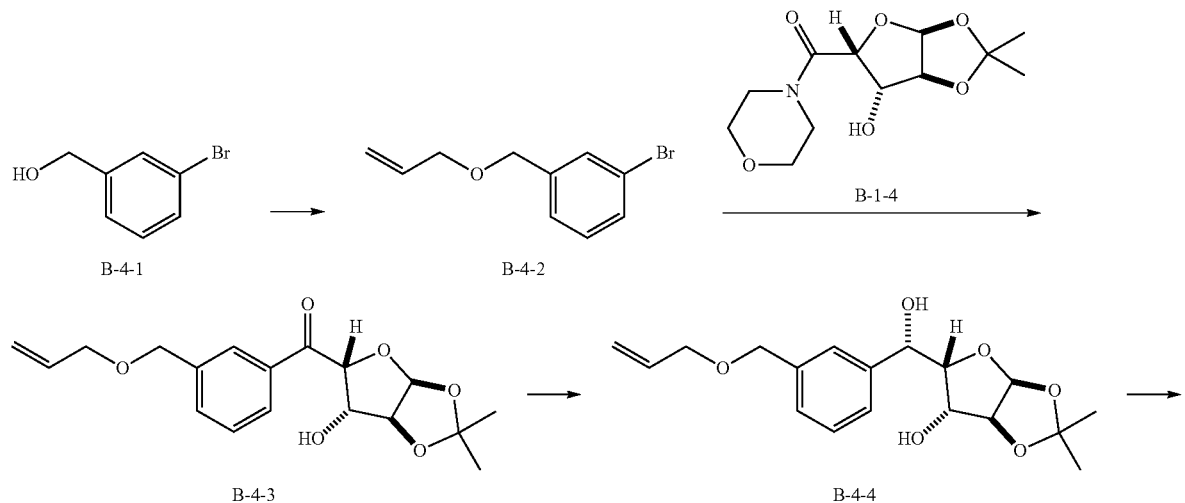

-continued

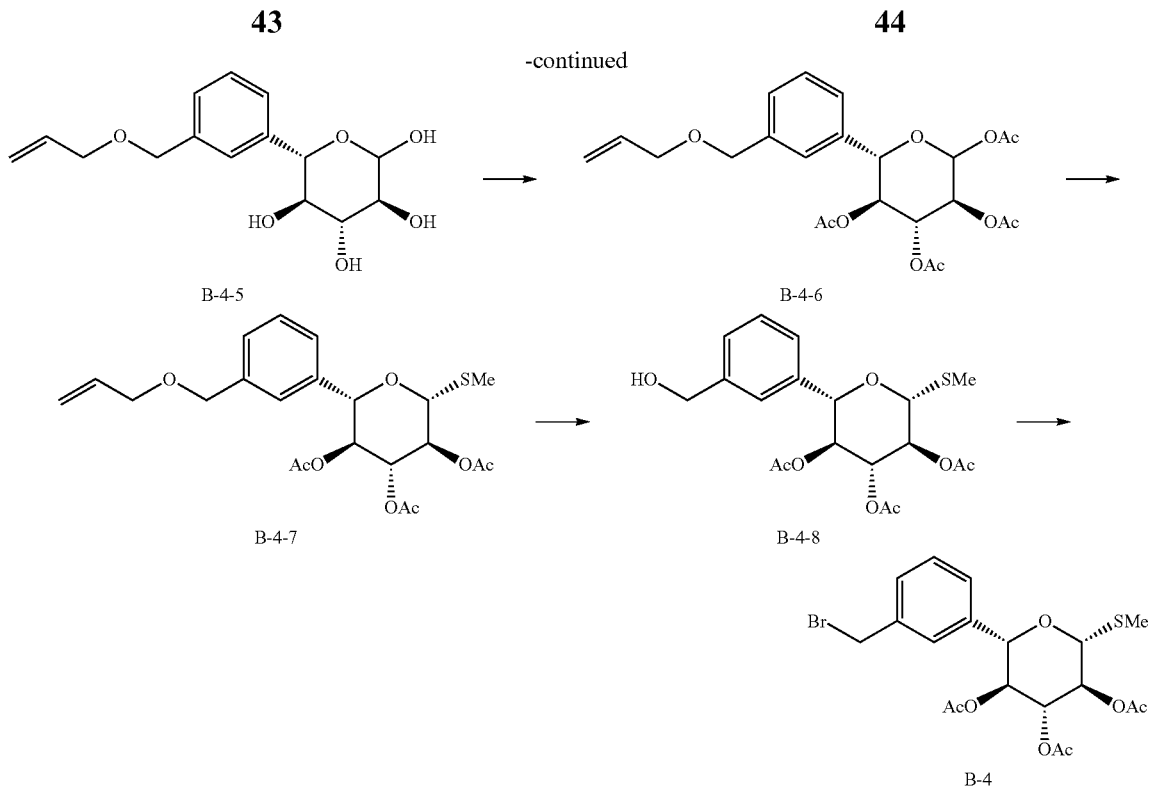

Step 1: Synthesis of the Compound B-4-2

Compound B-4-1 (25 g, 133.67 mmol, 1 eq) was dissolved in tetrahydrofuran (250 mL), and sodium hydride (10.69 g, 267.33 mmol, 60% purity, 2 eq) was added at 0° C. The mixture was stirred at 25° C. for 0.5 hours. Allyl bromide (48.51 g, 401.00 mmol, 34.65 mL, 3 eq) was slowly added to the reaction solution, and the mixture was reacted for another 2 hours at 25° C. After the reaction was completed, the reaction was quenched with saturated aqueous ammonium chloride solution (20 mL) at 0° C., and extracted with ethyl acetate (250 mL*2). The crude product was purified by column chromatography to give the compound B-4-2. $^1$H NMR (400 MHz, $CD_3OD$) δ ppm 4.04 (dt, J=5.5, 1.4 Hz, 2H), 4.45-4.52 (m, 2H), 5.17-5.34 (m, 2H), 5.95 (ddt, J=17.2, 10.7, 5.5, 5.5 Hz, 1H), 7.22-7.32 (m, 2H), 7.43 (d, J=7.5 Hz, 1H), 7.51 (s, 1H).

Step 2: Synthesis of the Compound B-4-3

Compound B-4-2 (14 g, 61.65 mmol, 1 eq) was dissolved in tetrahydrofuran (140 mL) at −78° C., and n-butyl lithium (2.5 M, 27.12 mL, 1.1 eq) was added under nitrogen. The mixture was reacted at −78° C. for 0.5 hours. At the same time, compound B-1-4 (18.53 g, 67.81 mmol, 1.1 eq) was dissolved in tetrahydrofuran (180 mL). The mixture was cooled to 0° C. and purged with nitrogen. Tert-butyl magnesium chloride (1.7 M, 47.14 mL, 1.3 eq) was then added, and the mixture was reacted at 0° C. for 0.5 hours. The solution of magnesium alkoxy was slowly added to the solution of alkyl lithium at −78° C. The reaction solution was reacted at −78° C. for 0.5 hours, and then heated to 25° C. and reacted for another 15.5 hours. After the reaction was completed, a solution of ammonium chloride (100 mL) was added to the reaction solution at 0° C. The reaction solution was diluted with ethyl acetate (200 mL), and then washed with water (50 mL*2). The combined organic phase was washed with saturated brine (50 mL*2), dried over anhydrous sodium sulfate, and filtered. The filtrate was rotary-evaporated to dryness. The crude product was purified by column chromatography to give the compound B-4-3. The product was confirmed by LCMS, LC-MS (m/z) 357 [M+Na]$^+$.

Step 3: Synthesis of the Compound B-4-4

Compound B-4-3 (13 g, 38.88 mmol, 1 eq) was dissolved in methanol (130 mL), and the solution was cooled to 0° C. Cerium trichloride heptahydrate (9.58 g, 38.88 mmol, 1 eq), and then sodium borohydride (2.94 g, 77.76 mmol, 2 eq) were added. The mixture was heated to 25° C. and reacted for 16 hours. After the reaction was completed, the reaction solution was quenched with saturated ammonium chloride aqueous solution (30 mL), and rotary-evaporated to dryness. The residue was diluted with ethyl acetate (100 mL), washed with water (50 mL*2), and then washed with saturated brine (50 mL*2) to remove water. Finally, the organic phase was dried over anhydrous sodium sulfate, and filtered. The filtrate was concentrated to dryness under reduced pressure to give the title compound B-4-4. The product was confirmed by LCMS, LC-MS (m/z) 359 [M+Na]$^+$.

Step 4: Synthesis of the Compound B-4-5

Compound B-4-4 (10.8 g, 32.11 mmol, 1 eq) was dissolved in water (50 mL) and glacial acetic acid (50 mL), and the solution was reacted at 100° C. for 16 hours. After the reaction was completed, the reaction solution was rotary evaporated to dryness under vacuum at 60° C., and then striped three times with toluene to give compound B-4-5. The product was confirmed by LCMS, LC-MS (m/z) 319 [M+Na]$^+$.

Step 5: Synthesis of the Compound B-4-6

Compound B-4-5 (9.2 g, 31.05 mmol, 1 eq) was dissolved in 1,4-dioxane (100 mL), and acetic anhydride (25.36 g, 248.38 mmol, 23.26 mL, 8 eq), pyridine (24.56 g, 310.48 mmol, 25.06 mL, 10 eq), and 4-dimethylaminopyridine (1.90 g, 15.52 mmol, 0.5 eq) were added. The mixture was stirred at 80° C. for 16 hours. After the reaction was completed, the 1,4-dioxane was removed by concentration under reduced pressure. The reaction solution was diluted with ethyl acetate (100 mL), and washed with 1 M diluted hydrochloric acid (100 mL*4). The organic phase was washed with water (50 mL*2), and then saturated brine (50 mL*2). Finally, the organic phase was dried over anhydrous sodium sulfate, and filtered. The filtrate was concentrated to dryness under reduced pressure. The crude product was purified by column chromatography to give the compound B-4-6, The product was confirmed by LCMS, LC-MS (m/z) 487 [M+Na]$^+$.

Step 6: Synthesis of B-4-7

Compound B-4-6 (6.2 g, 13.35 mmol, 1 eq) was dissolved in 1,4-dioxane (62 mL), and thiourea (3.56 g, 46.72 mmol, 3.5 eq) was added. The atmosphere was replaced with nitrogen three times, and trimethylsilyl trifluoromethanesulfonate (11.87 g, 53.40 mmol, 4 eq) was added at 25° C. The mixture was heated to 60° C. and reacted for 1 hour, and then cooled to 25° C. Iodomethane (9.47 g, 66.74 mmol, 5 eq) and diisopropylethylamine (17.25 g, 133.49 mmol, 10 eq) were added successively. The mixture was reacted at 25° C. for 15 hours. After the reaction was completed, the reaction solution was diluted with water (60 mL), and extracted with ethyl acetate (60 mL*3). The organic phases were combined, washed with saturated brine (50 mL), dried over anhydrous sodium sulfate, and filtered. The filtrate was rotary-evaporated to dryness under reduced pressure to give a crude product. The crude product was purified by column chromatography to give the title compound B-4-7. The product was confirmed by LCMS, LC-MS (m/z) 475 [M+Na]$^+$.

Step 7: Synthesis of B-4-8

To a reaction flask were added B-4-7 (4.4 g, 9.72 mmol, 1 eq), barbituric acid (2.49 g, 19.45 mmol, 2 eq), and ethanol (44 mL). The atmosphere was replaced with nitrogen three times, and tetrakis(triphenylphosphine)palladium (516.80 mg, 486.17 µmol, 0.05 eq) was added. The mixture was reacted under nitrogen at 65° C. for 16 hours. After the reaction was completed, the reaction solution was adjusted to a pH of 7-8 by addition of aqueous sodium bicarbonate solution, and then filtered on a Buchner funnel. The filtrate was collected, and extracted with ethyl acetate (40 mL*2). The organic phases were combined, washed with saturated brine (20 mL), dried over anhydrous sodium sulfate, and filtered. The filtrate was rotary-evaporated to dryness under reduced pressure to give a crude product. The crude product was purified by column chromatography to give the title compound B-4-8. The product was confirmed by LCMS, LC-MS (m/z) 435 [M+Na]$^+$.

Step 8: Synthesis of B-4

Compound B-4-8 (300 mg, 727.36 µmol, 1 eq) was dissolved in tetrahydrofuran (3 mL). Phosphorous tribromide (98.44 mg, 363.68 µmol, 34.18 µL, 0.5 eq) was added under nitrogen at 0° C. The mixture was stirred at 0° C. for 3 hours. After the reaction was completed, the reaction solution was washed twice with saturated aqueous potassium carbonate solution. The organic phase was collected, and the aqueous phase was extracted with ethyl acetate (3 mL*2). The organic phases were combined and concentrated to dryness under reduced pressure with a water pump. The crude product was purified by column chromatography to give the title compound B-4. $^1$H NMR (400 MHz, CDCl$_3$) δ ppm 1.83-1.86 (m, 3H), 2.02 (s, 3H), 2.10-2.13 (m, 3H), 2.20-2.22 (m, 3H), 4.46-4.49 (m, 2H), 4.54-4.58 (m, 1H), 5.10 (t, J=9.7 Hz, 1H), 5.20-5.27 (m, 1H), 5.31 (s, 1H), 5.34-5.40 (m, 1H), 7.30-7.38 (m, 4H).

Reference Example 8: Fragment B-5

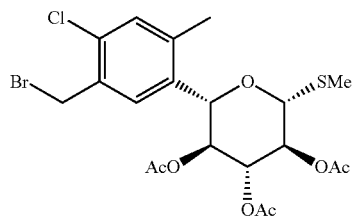 [SMILES: CS[C@H]1O[C@@H](c2cc(CBr)c(Cl)cc2C)[C@H](OC(C)=O)[C@@H](OC(C)=O)[C@@H]1OC(C)=O]

Route of Synthesis

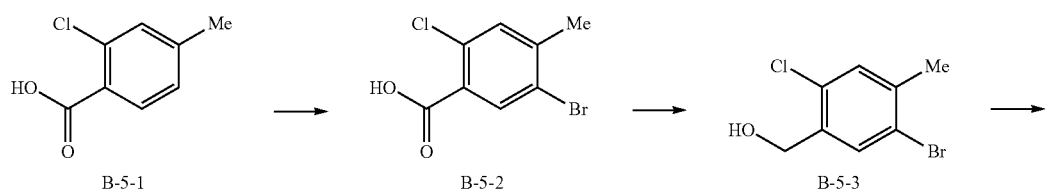

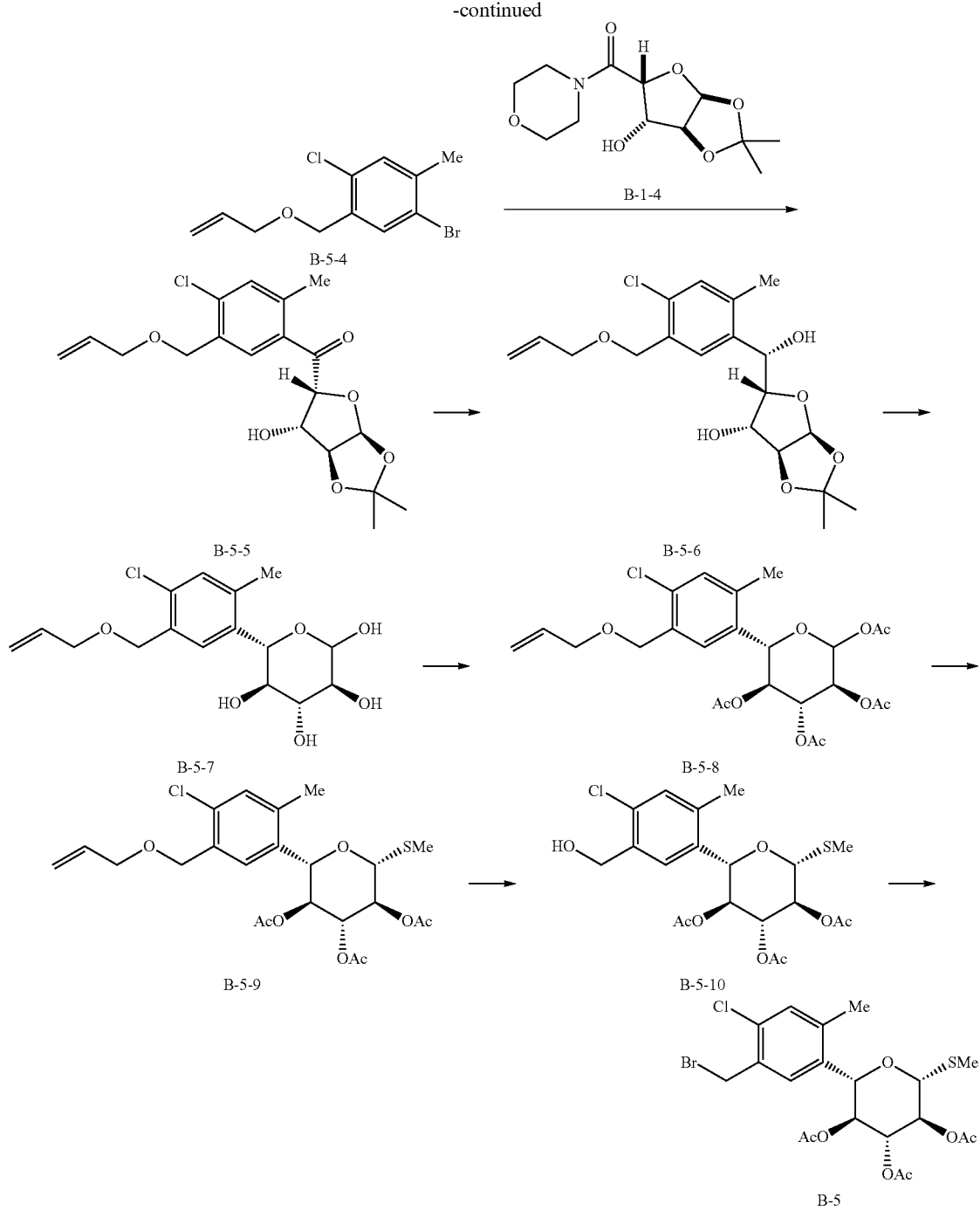

Step 1: Synthesis of the Compound B-5-2

To a reaction flask were added compound B-5-1 (11.00 g, 64.48 mmol, 1 eq) and N-bromosuccinimide (14.30 g, 80.34 mmol, 1.25 eq). Sulfuric acid (202.40 g, 2.06 mol, 110.00 mL, 32.00 eq) was added at 0° C. The mixture was stirred for 1 hour. The reaction solution was added dropwise to ice water (500 mL), and the aqueous phase was extracted three times with ethyl acetate (200 mL*3). The organic phases were combined, and concentrated to give compound B-5-2, which was directly used in the next reaction.

Step 2: Synthesis of the Compound B-5-3

To a reaction flask were added compound B-5-2 (19.00 g, 76.16 mmol, 1 eq) and anhydrous tetrahydrofuran (50.0 mL). A solution of borane in tetrahydrofuran (1 M, 160.00 mL, 2.10 eq) was added dropwise, and the reaction system was stirred at 20° C. for 16 hours. Methanol (100 mL) was added dropwise to the reaction solution at 20° C., while bubbling with nitrogen. After quenching the reaction, the mixture solution was refluxed at 70° C. for 1 hour, and concentrated to dryness with a water pump at 45° C. to give a crude product. Water (200 mL) was added, and the mixture was extracted with ethyl acetate (200 mL*3). The organic phases were combined, washed with saturated brine (200 mL), dried over anhydrous sodium sulfate, and filtered. The filtrate was concentrated to give compound B-5-3. $^1$H NMR (400 MHz, CDCl$_3$) δ ppm 7.66 (s, 1H), 7.24 (s, 1H), 4.73 (d, J=6.02 Hz, 2H), 2.38 (s, 3H), 1.88 (t, J=6.27 Hz, 1H).

Step 3: Synthesis of the Compound B-5-4

To a reaction flask were added compound B-5-3 (15.60 g, 66.24 mmol, 1 eq) and anhydrous N,N-dimethylformamide (100 mL). Sodium hydride (6.24 g, 156.01 mmol, 60% purity, 2.36 eq) was added at 0° C. The reaction system was stirred at 0° C. for 0.5 hours, and 3-bromopropene (24.04 g, 198.72 mmol, 3 eq) was added. The reaction system was stirred at room temperature (20° C.) for 15.5 hours. Water (200 mL) was added dropwise to the reaction solution to quench the reaction, and the mixture was extracted with ethyl acetate (200 mL*3). The organic phases were combined, washed with saturated brine (200 mL), dried over anhydrous sodium sulfate, and filtered. The filtrate was concentrated to give a crude product. The crude product was purified by column chromatography to give the title compound B-5-4, $^1$H NMR (400 MHz, CDCl$_3$) δ ppm 7.66 (s, 1H), 7.23 (s, 1H), 5.91-6.05 (m, 1H), 5.31-5.42 (m, 1H), 5.19-5.29 (m, 1H), 4.55 (s, 2H), 4.10 (dt, J=5.58, 1.35 Hz, 2H), 2.37 (s, 3H).

Step 4: Synthesis of the Compound B-5-5

To a reaction flask were added compound B-5-4 (15.30 g, 55.52 mmol, 1 eq) and anhydrous tetrahydrofuran (200 mL). N-butyl lithium (2.5 M, 27 mL, 1.22 eq) was added under nitrogen at −70° C. The reaction system was stirred at −70° C. for 0.5 hours. Compound B-1-4 (15.30 g, 55.99 mmol, 1.01 eq) and anhydrous tetrahydrofuran (200 mL) were added to a reaction flask. Tert-butyl magnesium chloride (1.7 M, 54 mL, 1.65 eq) was added under nitrogen at 0° C., and the reaction system was stirred at 0° C. for 0.5 hours. The solution of magnesium alkoxy was slowly added to the solution of alkyl lithium, and the reaction system was stirred at −70° C. for 0.5 hours. The reaction system was slowly warmed to room temperature (20° C.) and stirred for 1 hour. Saturated ammonium chloride (200 mL) was added dropwise to the reaction solution to quench the reaction, and the reaction solution was concentrated to remove organic solvent. Citric acid was added to adjust the solution to clear. The solution was extracted with ethyl acetate (200 mL*3). The organic phases were combined, washed with saturated brine (200 mL), dried over anhydrous sodium sulfate, and filtered. The filtrate was concentrated to give a crude product. The crude product was purified by column chromatography to give the title compound B-5-5. The product was confirmed by LCMS, LC-MS (m/z) 405 [M+Na]$^+$.

Step 5: Synthesis of the Compound B-5-6

Compound B-5-5 (10.60 g, 27.69 mmol, 1 eq) was dissolved in anhydrous methanol (200 mL), and the solution was cooled to 0° C. Cerium trichloride heptahydrate (12.38 g, 33.23 mmol, 1.20 eq), and then sodium borohydride (2.1 g, 55.38 mmol, 2 eq) were added. The mixture was heated to 25° C. and reacted for 16 hours. After the reaction was completed, the reaction solution was quenched with saturated aqueous ammonium chloride solution (30 mL), and rotary-evaporated to dryness. The residue was diluted with ethyl acetate (100 mL), washed with water (50 mL*2), and then washed with saturated brine (50 mL*2) to remove water. Finally, the organic phase was dried over anhydrous sodium sulfate, and filtered. The filtrate was concentrated to dryness under reduced pressure to give the title compound B-5-6, which was used directly in the next reaction.

Step 6: Synthesis of the Compound B-5-7

To a reaction flask were added compound B-5-6 (9.85 g, 19.00 mmol, 1 eq), acetic acid (60 mL), and water (60 mL), and the mixture was stirred at 100° C. for 8 hours. The reaction solution was concentrated to give a crude product, and the crude product was then striped with toluene (100 mL) to dryness. This process was repeated twice to give the title compound B-5-7, which was directly used in the next reaction.

Step 7: Synthesis of the Compound B-5-8

To a reaction flask were added compound B-5-7 (10.00 g, 29.00 mmol, 1 eq), triethylamine (16.72 g, 165.24 mmol, 23.0 mL, 5.70 eq), acetic anhydride (21.80 g, 213.54 mmol, 20 mL, 7.36 eq), 4-dimethylaminopyridine (40 mg, 327.42 µmol, 1.13 e−2 eq), and acetonitrile (100 mL). The mixture was stirred at 25° C. for 2 hours. The reaction solution was concentrated to give a crude product. Ethyl acetate (200 mL) was added, and the mixture was extracted with 50% saturated aqueous sodium hydrogen sulfate solution (200 mL*2). The aqueous phases were combined, and extracted with ethyl acetate (200 mL*2). The organic phases were combined, washed with saturated brine (200 mL), dried over anhydrous sodium sulfate, and filtered. The filtrate was concentrated to give a crude product. The crude product was purified by column chromatography to give the title compound B-5-8. The product was confirmed by LCMS, LC-MS (m/z) 535 [M+Na]$^+$.

Step 8: Synthesis of the Compound B-5-9

To a reaction flask were added compound B-5-8 (3.60 g, 7.02 mmol, 1 eq), thiourea (1.08 g, 14.19 mmol, 2.02 eq) and anhydrous dioxane (40 mL). The reaction system was stirred at 80° C. for 2 hours. Subsequently, trimethylsilyl trifluoromethanesulfonate (3.90 g, 17.55 mmol, 3.17 mL, 2.50 eq) was added, and the mixture was stirred at 80° C. for another 1 hour. The reaction solution was cooled to room temperature. Iodomethane (3.06 g, 21.56 mmol, 1.34 mL, 3.07 eq) and diisopropylethylamine (4.54 g, 35.09 mmol, 6.11 mL, 5 eq) were added. The reaction system was stirred at 25° C. for 15 hours. Water (50 mL) was added to the reaction solution, and the mixture was extracted with ethyl acetate (50 mL*2). The organic phases were combined, washed with saturated brine (50 mL), dried over anhydrous sodium sulfate, and filtered. The filtrate was concentrated to give a crude product. The crude product was purified by column chromatography to give the title compound B-5-9. $^1$H NMR (400 MHz, CDCl$_3$) δ ppm 7.48 (s, 1H), 7.15 (s, 1H), 5.98 (ddt, J=17.32, 10.60, 5.36, 5.36 Hz, 1H), 5.22-5.37 (m, 5H), 4.70 (d, J=10.04 Hz, 1H), 4.56 (d, J=2.76 Hz, 2H), 4.54 (d, J=9.79 Hz, 1H), 4.07 (ddt, J=5.49, 2.48, 1.41, 1.41 Hz, 2H), 2.38 (s, 3H), 2.19 (s, 3H), 2.11 (s, 3H), 2.03 (s, 3H), 1.81 (s, 3H).

Step 9: Synthesis of the Compound B-5-10

To a reaction flask were added compound B-5-9 (2.70 g, 5.39 mmol, 1 eq), barbituric acid (1.38 g, 10.78 mmol, 2.0 eq), anhydrous ethanol (20 mL), and anhydrous dichloromethane (10 mL). Tetrakis(triphenylphosphine)palladium (622 mg, 0.539 mmol, 0.1 eq) was added under a nitrogen atmosphere, and the reaction system was stirred at 40° C. for 12 hours. The reaction solution was filtered, and the filtrate was concentrated to give a crude product. Water (500 mL) was added, and the mixture was extracted with ethyl acetate (500 mL*3). The organic phases were combined, washed with saturated brine (500 mL), dried over anhydrous sodium sulfate, and filtered. The filtrate was concentrated to give a crude product. The crude product was purified by column chromatography to give the title compound B-5-10. $^1$H NMR (400 MHz, CDCl$_3$) δ ppm 7.51 (s, 1H), 7.16 (s, 1H), 5.35-5.41 (m, 1H), 5.26 (dt, J=15.00, 9.57 Hz, 2H), 4.68-4.77 (m, 3H), 4.55 (d, J=10.04 Hz, 1H), 2.38 (s, 3H), 2.17-2.23 (m, 3H), 2.11 (s, 3H), 2.02 (s, 3H), 1.81 (s, 3H).

Step 10: Synthesis of the Compound B-5

To a reaction flask were added compound B-5-10 (0.60 g, 468.88 μmol, 1 eq) and anhydrous tetrahydrofuran (10 mL). Phosphorous tribromide (288.00 mg, 1.06 mmol, 0.10 mL, 2.27 eq) was added dropwise under nitrogen at 0° C. The mixture was slowly warmed to 25° C. and stirred for 12 hours. Water (20 mL) was added dropwise to the reaction solution to quench the reaction, and the mixture was concentrated to remove the organic solvent. The remaining aqueous phase was extracted with ethyl acetate (20 mL*3). The organic phases were combined, washed with saturated brine (20 mL), dried over anhydrous sodium sulfate, and filtered. The filtrate was concentrated to give a crude product. The crude product was purified by column chromatography to give the title compound B-5, $^1$H NMR (400 MHz, CDCl$_3$) δ ppm 1.83 (s, 3H), 2.03 (s, 3H), 2.11 (s, 3H), 2.20 (s, 3H), 2.40 (s, 3H), 4.50-4.59 (m, 3H), 4.66 (d, J=10.04 Hz, 1H), 5.20-5.40 (m, 3H), 7.20 (s, 1H), 7.41 (s, 1H).

Reference Example 9: Fragment B-6

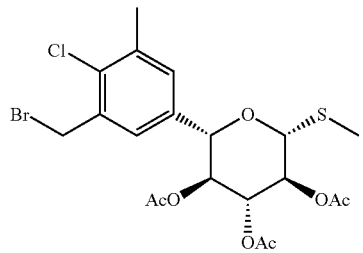 [SMILES: CS[C@H]1O[C@@H](c2cc(C)c(Cl)c(CBr)c2)[C@H](OC(C)=O)[C@@H](OC(C)=O)[C@@H]1OC(C)=O]

Route of Synthesis

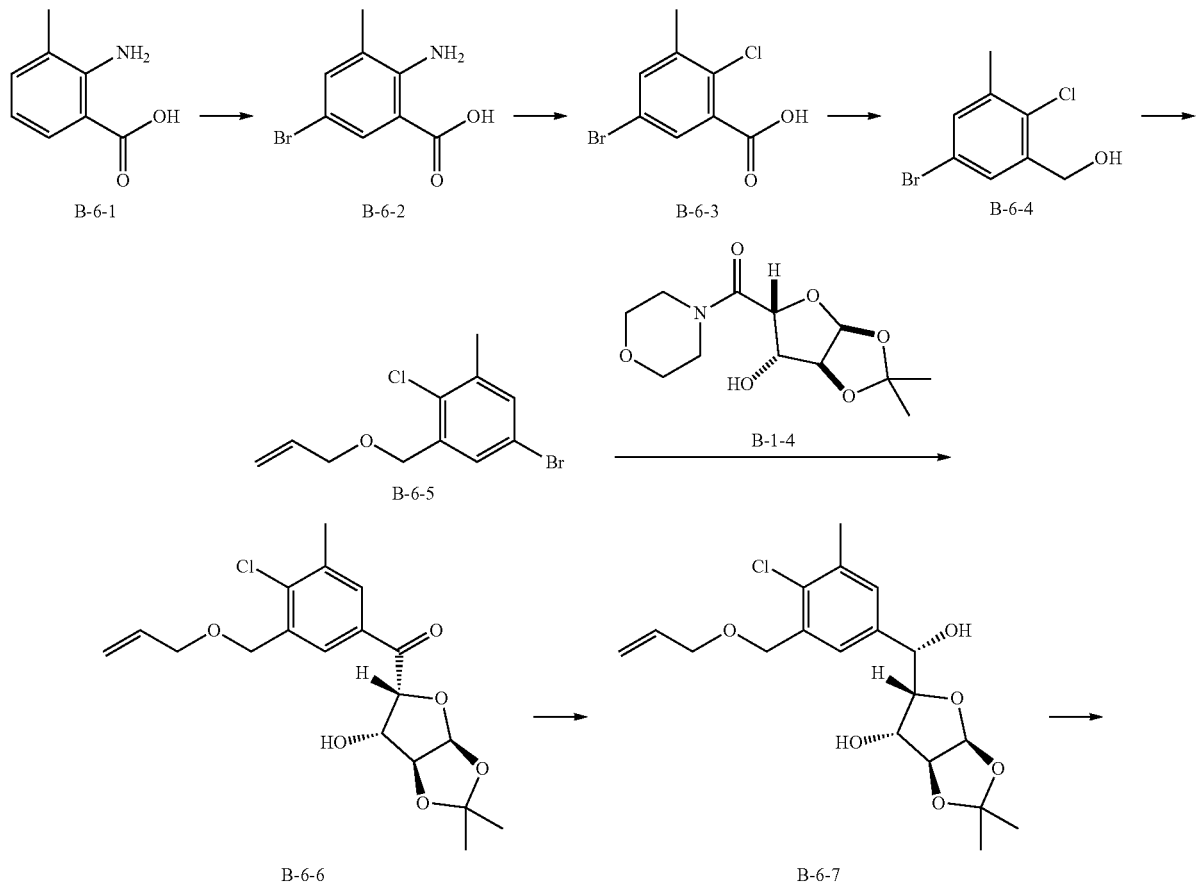

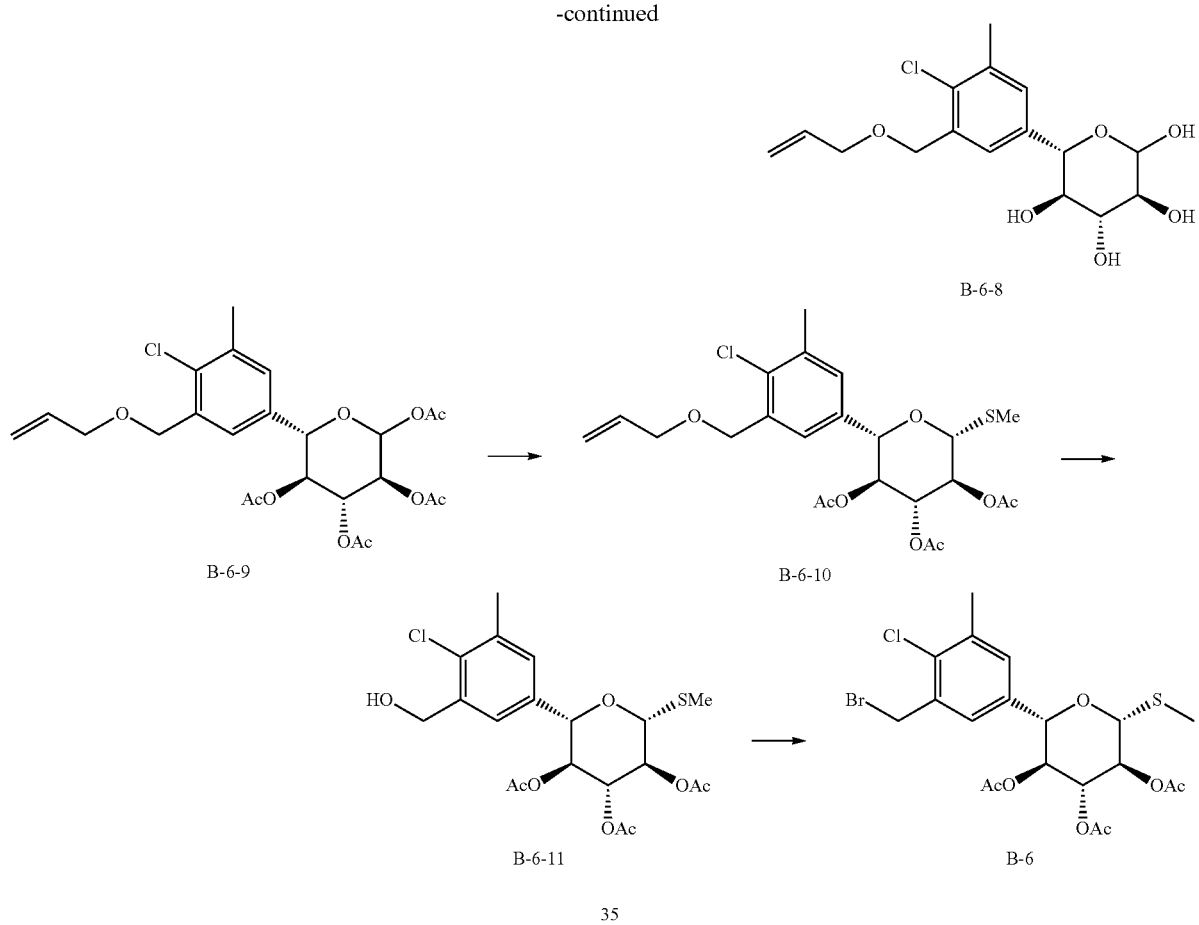

Step 1: Synthesis of the Compound B-6-2

To a reaction flask were added successively concentrated sulfuric acid (70 mL) and compound B-6-1 (20 g, 132.31 mmol, 1.89 mL, 1 eq), and the mixture was stirred until dissolved. N-bromosuccinimide (28.26 g, 158.77 mmol, 1.2 eq) was added at 0° C. in portions. After the addition was completed, the mixture was stirred at 30° C. until the N-bromosuccinimide was completely dissolved. The solution was further reacted at 30° C. for 0.5 hours. The reaction solution was slowly added to stirred ice water (1 L) to quench the reaction, and then the mixture was stirred at 0° C. for 0.5 hours. After filtration, the filter cake was washed three times with water (100 mL), collected, and then dried to give compound B-6-2, which was directly used in the next reaction.

Step 2: Synthesis of the Compound B-6-3

To a reaction flask were added successively water (250 mL), acetonitrile (125 mL), compound B-6-2 (25 g, 97.80 mmol, 1 eq), and concentrated hydrochloric acid (38.55 g, 391.21 mmol, 37.79 mL, 37% purity, 4 eq). A suspension was obtained after stirring. Sodium nitrite (7.09 g, 102.69 mmol, 1.05 eq) was added to the reaction mixture at 0° C., and the mixture was stirred for 0.5 hours. The reaction mixture was added dropwise to a solution of cuprous chloride (10.17 g, 102.69 mmol, 2.46 mL, 1.05 eq), concentrated hydrochloric acid (38.55 g, 391.21 mmol, 37.79 mL, 37% purity, 4 eq) and water (250 mL) at 0° C. After the addition was completed, the reaction solution was reacted at 70° C. for 3 hours. The reaction solution was concentrated to remove acetonitrile. The residue was cooled to room temperature, and then filtered. The filter cake was washed three times with water (100 mL). The filter cake was collected and dissolved in ethyl acetate (200 mL). The layers were separated. The organic phase was dried over anhydrous sodium sulfate, and filtered. The filtrate was concentrated under reduced pressure to give compound B-6-3. The product was confirmed by LCMS, LC-MS (m/z) 248.9, 250.8 [M+H]$^+$.

Step 3: Synthesis of the Compound B-6-4

To a reaction flask were added compound B-6-3 (18 g, 64.93 mmol, 1 eq) and tetrahydrofuran (300 mL). Borane dimethyl sulfide (10 M, 19.48 mL, 3 eq) was added dropwise under a nitrogen atmosphere. After the addition was completed, the mixture was reacted with stirring at 30° C. for 16 hours. After the reaction was completed, methanol (100 mL) was added dropwise to the reaction solution to quench the reaction. The reaction solution was refluxed at 70° C. for 1 hour, and then concentrated under reduced pressure to give compound B-6-4, which was directly used in the next reaction.

Step 4: Synthesis of the Compound B-6-5

To a reaction flask were added compound B-6-4 (16.5 g, 70.06 mmol, 1 eq) and DMF (180 mL). The mixture was cooled to 0° C., and sodium hydride (5.60 g, 140.12 mmol, 60% purity, 2 eq) was added. After stirring at 0° C. for 0.5 hours, allyl bromide (25.43 g, 210.19 mmol, 3 eq) was added to the reaction solution. The mixture was reacted with stirring at 30° C. for 10 hours. The reaction solution was quenched by adding water (300 mL), and extracted with ethyl acetate (100 mL*3). The organic phases were combined, washed with saturated brine (100 mL), and then concentrated to give a crude product. The crude product was purified by column chromatography to give compound B-6-5. The product was confirmed by LCMS, LC-MS (m/z) 275, 277 [M+H]$^+$.

Step 5: Synthesis of the Compound B-6-6

To a reaction flask were added compound B-6-5 (16 g, 52.26 mmol, 1 eq) and tetrahydrofuran (160 mL). The mixture was cooled to −78° C., and n-butyl lithium (2.5 M, 27.17 mL, 1.3 eq) was added dropwise. The mixture was stirred at −78° C. for 0.5 hours. Compound B-1-4 (14.28 g, 52.26 mmol, 1 eq) and tetrahydrofuran (160 mL) were added to a reaction flask, and the mixture was cooled to 0° C. Tert-butyl magnesium chloride (1.7 M, 49.18 mL, 1.6 eq) was added dropwise, and the mixture was stirred at 0-5° C. for 0.5 hours. The solution of magnesium alkoxy was slowly added dropwise to the solution of alkyl lithium at −78° C. The reaction solution was stirred at −78° C. for 0.5 hours, and then reacted with stirring at 25° C. for another 2 hours. A mixed solution of saturated ammonium chloride and saturated brine (volume ratio of 1:1, 150 mL in total) was added dropwise to the reaction solution at 0° C. to quench the reaction. The mixture was extracted with ethyl acetate (100 mL*3), dried over anhydrous sodium sulfate, and filtered. The filtrate was concentrated under reduced pressure. The crude product was purified by column chromatography to give compound B-6-6. The product was confirmed by LCMS, LC-MS (m/z) 383 [M+H]$^+$.

Step 6: Synthesis of the Compound B-6-7

Compound B-6-6 (7.40 g, 17.40 mmol, 1 eq) was dissolved in anhydrous methanol (100 mL), and the solution was cooled to 0° C. Cerium trichloride heptahydrate (7.77 g, 20.88 mmol, 1.20 eq), and then sodium borohydride (1.32 g, 34.8 mmol, 2 eq) were added. The mixture was heated to 25° C. and reacted for 16 hours. After the reaction was completed, the reaction solution was quenched with saturated aqueous ammonium chloride solution (30 mL), and rotary-evaporated to dryness. The residue was diluted with ethyl acetate (100 mL), washed with water (50 mL*2), and then washed with saturated brine (50 mL*2) to remove water. Finally, the organic phase was dried over anhydrous sodium sulfate, and filtered. The filtrate was concentrated to dryness under reduced pressure to give the title compound B-6-7, which was directly used in the next reaction.

Step 7: Synthesis of the Compound B-6-8

To a 250 mL single-necked flask were added compound B-6-7 (6.5 g, 16.89 mmol, 1 eq), acetic acid (40 mL) and water (40 mL), and the mixture was reacted at 100° C. for 16 hours. The reaction solution was concentrated to dryness under reduced pressure, and the residue was azeotropically striped with toluene (50 mL*2) to give the compound B-6-8, which was directly used in the next reaction.

Step 8: Synthesis of the Compound B-6-9

To a reaction flask were added compound B-6-8 (6 g, 17.40 mmol, 1 eq), triethylamine (11.62 g, 114.85 mmol, 15.99 mL, 6.6 eq), 4-dimethylaminopyridine (212.60 mg, 1.74 mmol, 0.1 eq) and acetonitrile (40 mL). Acetic anhydride (11.73 g, 114.85 mmol, 10.76 mL, 6.6 eq) was then added. The mixture was reacted at 25° C. for 16 hours. The reaction solution was concentrated to remove acetonitrile, and 0.5N hydrochloric acid (40 mL) was then added. The mixture was extracted with ethyl acetate (50 mL*3). The organic phase was washed with saturated brine (50 mL), and concentrated under reduced pressure to give a crude product. The crude product was purified by column chromatography to give compound B-6-9.

Step 9: Synthesis of the Compound B-6-10

To a reaction flask were added compound B-6-9 (2.5 g, 4.39 mmol, 1 eq), thiourea (1.17 g, 15.35 mmol, 3.5 eq) and dioxane (30 mL). The atmosphere was replaced with nitrogen, and trimethylsilyl trifluoromethanesulfonate (3.90 g, 17.55 mmol, 3.17 mL, 4 eq) was then added. The mixture solution was reacted at 80° C. for 0.5 hours, and then cooled to 0-5° C. Iodomethane (1.87 g, 13.16 mmol, 819.23 µL, 3 eq) and diisopropylethylamine (2.83 g, 21.93 mmol, 3.82 mL, 5 eq) were added successively, and the mixture was reacted at 25° C. for another 10 hours. Water (30 mL) was added to the reaction solution, and the mixture was extracted with ethyl acetate (30 mL*3). The organic phases were combined, washed with saturated brine (30 mL), and concentrated to give a crude product. The crude product was purified by column chromatography to give the compound B-6-10. The product was confirmed by LCMS, LC-MS (m/z) 523 [M+Na]$^+$.

Step 10: Synthesis of the Compound B-6-11

To a reaction flask were added compound B-6-10 (1.257 g, 2.515 mmol, 1 eq), barbituric acid (644.30 mg, 5.03 mmol, 2 eq), tetrakis(triphenylphosphine)palladium (290.63 mg, 251.50 µmol, 0.1 eq) and EtOH (40 mL). The atmosphere was replaced with nitrogen, and then the mixture was reacted with stirring at 40° C. for 16 hours. Saturated aqueous sodium carbonate solution (50 mL) and ethyl acetate (50 mL) were added to the reaction solution, and a large amount of solid was precipitated out. The mixture was filtered. The layers were separated, and the aqueous phase was extracted with ethyl acetate (50 mL*3). The organic phases were combined, washed with saturated brine (50 mL), dried over anhydrous sodium sulfate, and filtered. The filtrate was concentrated under reduced pressure. The crude product was purified by column chromatography to give compound B-6-11. The product was confirmed by LCMS, LC-MS (m/z) 483 [M+Na]$^+$.

Step 11: Synthesis of B-6

To a reaction flask were added compound B-6-11 (200 mg, 418.07 µmol, 1 eq) and tetrahydrofuran (5 mL). Phosphorous tribromide (113.17 mg, 418.07 µmol, 39.29 µL, 1 eq) was added at 0° C. The reaction solution was reacted at −10° C. for 0.5 hours, and then poured into an aqueous potassium carbonate solution (20 mL, 1 M) at 0° C. The mixture was extracted with ethyl acetate (20 mL*3). The organic phase was dried over anhydrous sodium sulfate and filtered. The filtrate was concentrated to give a crude product. The crude product was purified by column chromatography to give the title compound B-6. $^1$H NMR (400 MHz, CDCl$_3$) δ ppm 1.86 (s, 3H), 2.01 (s, 3H), 2.10 (s, 3H), 2.21 (s, 3H), 2.40 (s, 3H), 4.40 (d, J=10.04 Hz, 1H), 4.51-4.57 (m, 2H), 4.60-4.65 (m, 1H), 5.06 (t, J=9.66 Hz, 1H), 5.17-5.25 (m, 1H), 5.31-5.38 (m, 1H), 7.22 (s, 1H), 7.24 (s, 1H).

Example 1: WXD001 or WXD002
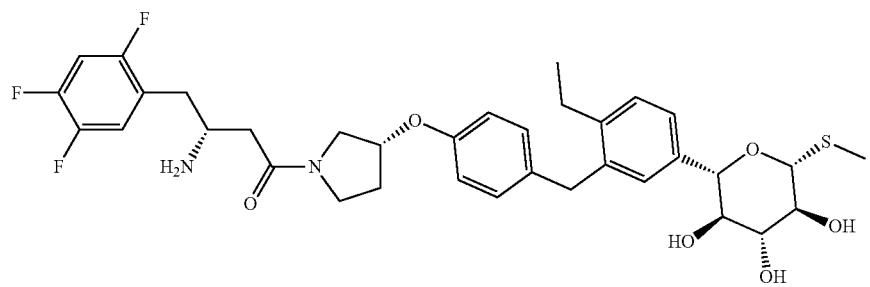
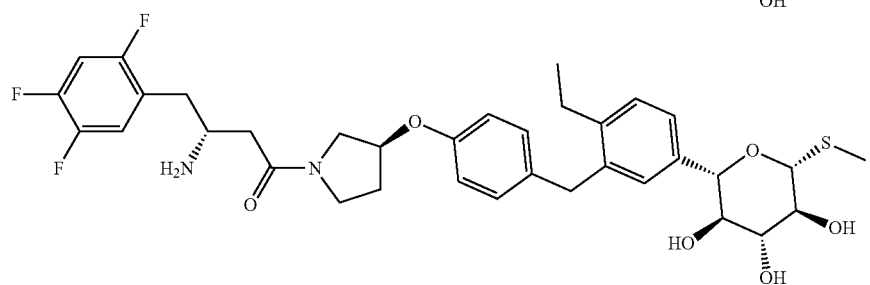
Route of Synthesis
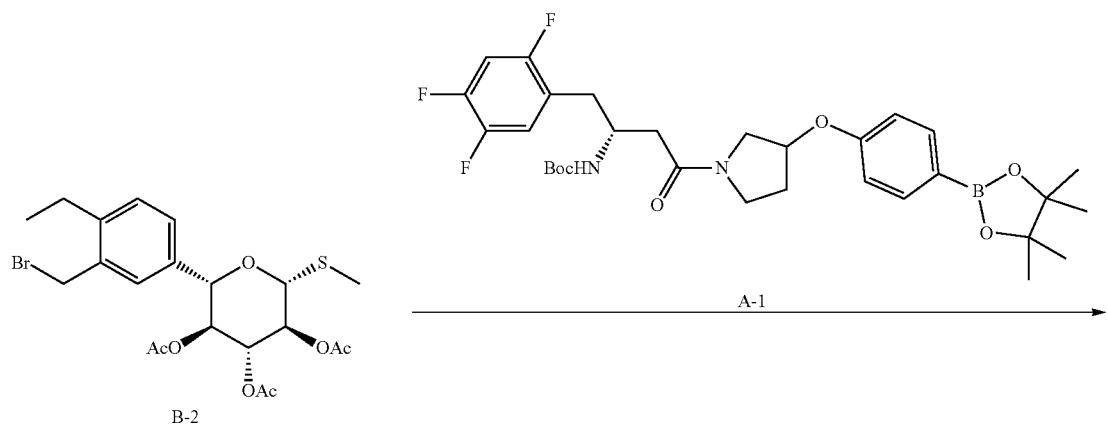
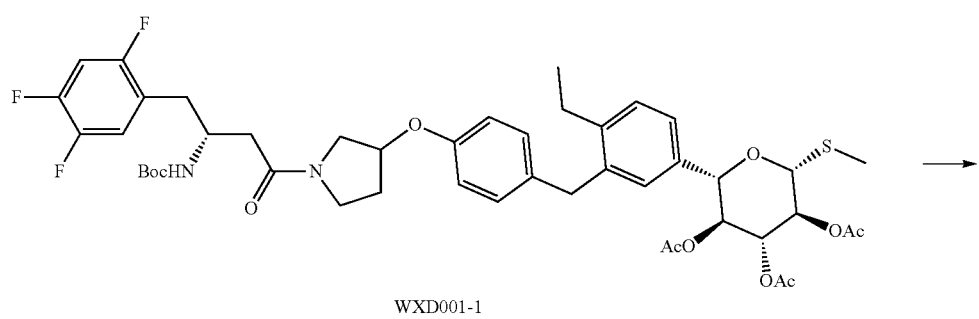

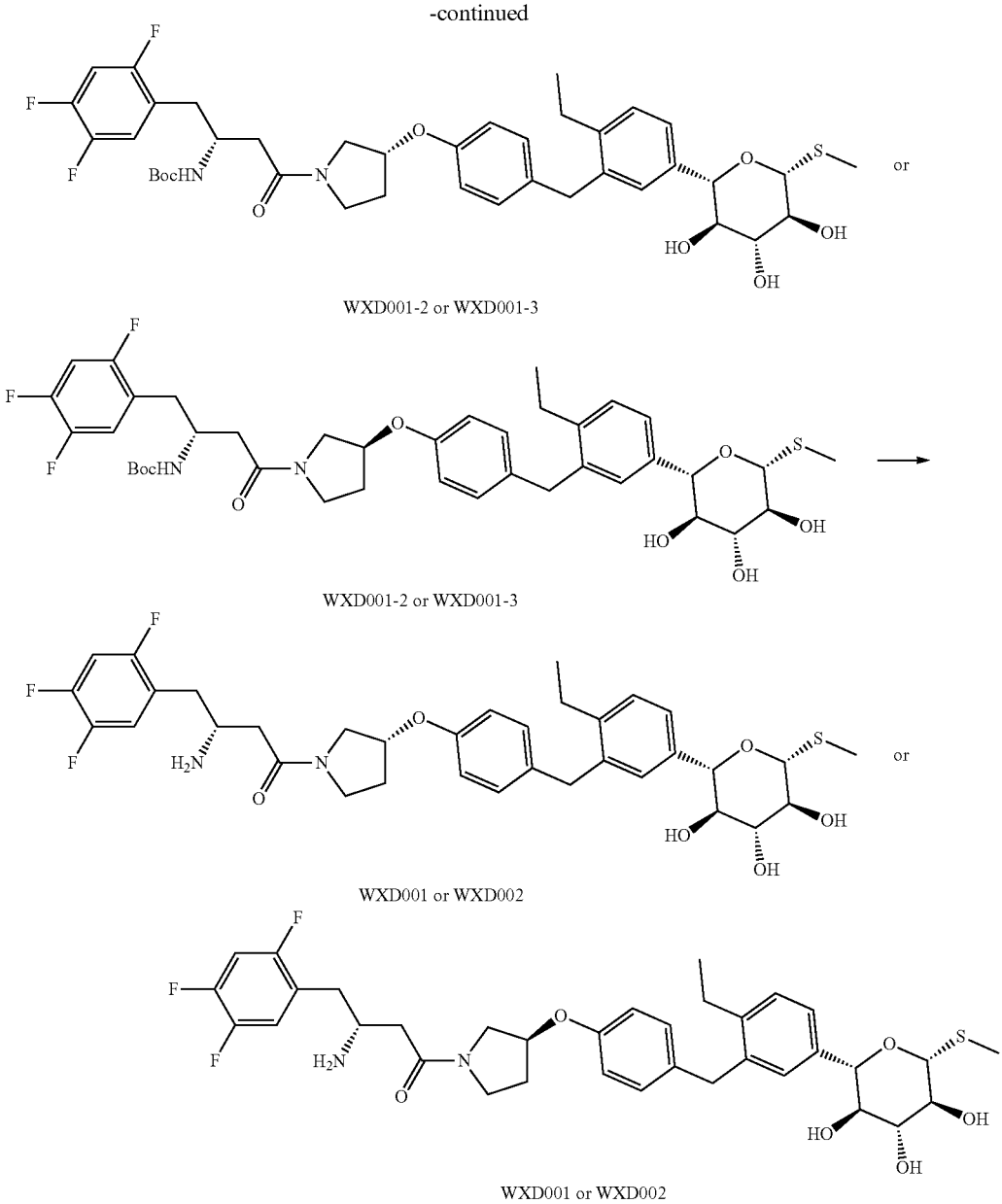

Step 1: Synthesis of WXD001-1

To a reaction flask were added B-2 (0.35 g, 695.27 μmol, 1 eq), A-1 (626.19 mg, 1.04 mmol, 1.49 eq), $Na_2CO_3$ (147.38 mg, 1.39 mmol, 2 eq), toluene (5 mL), EtOH (1 mL) and $H_2O$ (1 mL). The atmosphere was replaced with nitrogen, and then $Pd(PPh_3)_4$ (160.68 mg, 139.05 μmol, 0.2 eq) was added. The mixture was stirred at 50° C. for 3 hours. After the reaction was completed, the reaction solution was diluted with 20 mL of water, and extracted with ethyl acetate (20 mL*3). The organic phases were combined, washed with saturated brine (20 mL), dried over anhydrous sodium sulfate, and filtered. The filtrate was rotary-evaporated to dryness to give a crude product. The crude product was purified by column chromatography to give WXD001-1.

Step 2: Synthesis of WXD001-2 or WXD001-3

To a reaction flask were added WXD001-1 (229 mg, 254.16 μmol, 1 eq), LiOH·$H_2O$ (213 mg, 5.08 mmol, 20 eq), THF (0.5 mL), MeOH (1 mL), and $H_2O$ (1 mL), and the mixture was reacted at 25° C. for 1 hour. After the reaction was completed, 10 mL of water was added to the reaction solution. The mixture was extracted with ethyl acetate (10 mL*3). The organic phase was dried over anhydrous sodium sulfate, and filtered. The filtrate was rotary-evaporated to dryness to give a crude product. The crude product was chirally resolved by SFC (chromatographic column: REGIS (s,s) WHELK-O1 (250 mm×30 mm, 5 μm); mobile phase: [0.1% $NH_3·H_2O$-isopropanol]; B (isopropanol) %: 40%-40%, min) to give WXD001-2 (t=4.167 min) or WXD001-3 (t=2.909 min).

Step 3: Synthesis of WXD001 or WXD002

To a reaction flask were added WXD001-2 (60 mg, 77.43 µmol, 1 eq), EtOAc (3 mL), and HCl/EtOAc (4 M, 1 mL, 51.66 eq), and the mixture was reacted at 25° C. for 1 hour. After the reaction was completed, the reaction solution was rotary-evaporated to dryness under reduced pressure to give a crude product. The crude product was subjected to preparative high performance liquid chromatography (chromatographic column: Boston Prime C18 150×30 mm, 5 µm; mobile phase: [water (0.05% ammonium hydroxide v/v)-acetonitrile]; B (acetonitrile) %: 47%-77%, 8 min) to give WXD001. Corresponding SFC (method: chromatographic column: Chiralpak AD-3 100×4.6 mm I.D., 3 µm; mobile phase: $CO_2$-40% methanol (0.05% DEA); flow rate: 2.8 mL/min; column temperature: 40° C.), retention time t=4.404 min.

To a reaction flask were added WXD001-3 (60 mg, 77.43 µmol, 1 eq), EtOAc (3 mL), and HCl/EtOAc (4 M, 1 mL, 51.66 eq), and the mixture was reacted at 25° C. for 1 hour. After the reaction was completed, the reaction solution was rotary-evaporated to dryness under reduced pressure to give a crude product. The crude product was subjected to preparative high performance liquid chromatography (chromatographic column: Boston Prime C18 150×30 mm 5 µm; mobile phase: [water (0.05% ammonium hydroxide v/v)-acetonitrile]; B (acetonitrile) %: 47%-77%, 8 min) to give WXD002. Corresponding SFC (method: chromatographic column: Chiralpak AD-3 100×4.6 mm I.D., 3 µm, mobile phase: $CO_2$-40% methanol (0.05% DEA); flow rate: 2.8 mL/min; column temperature: 40° C.), retention time t=5.921 min.

Example 2: WXD003

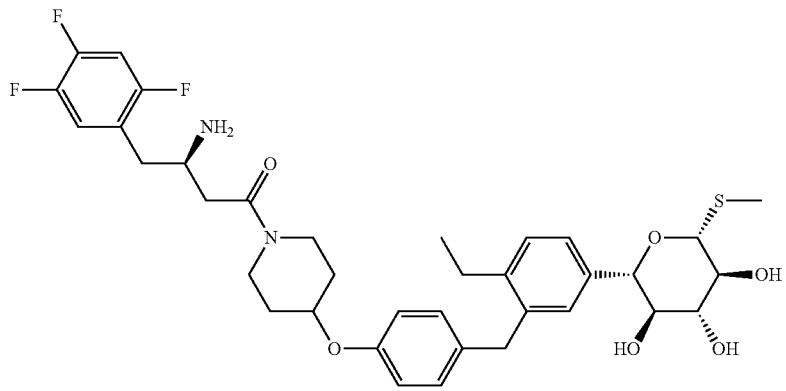 [SMILES: CCc1ccc([C@@H]2O[C@H](SC)[C@@H](O)[C@H](O)[C@H]2O)cc1Cc1ccc(OC2CCN(C(=O)C[C@H](N)Cc3cc(F)c(F)cc3F)CC2)cc1]

Route of Synthesis

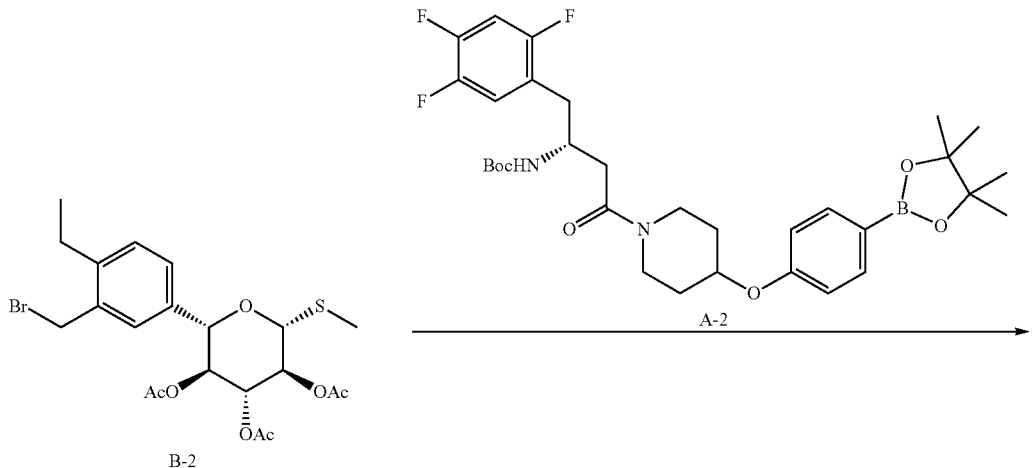

-continued

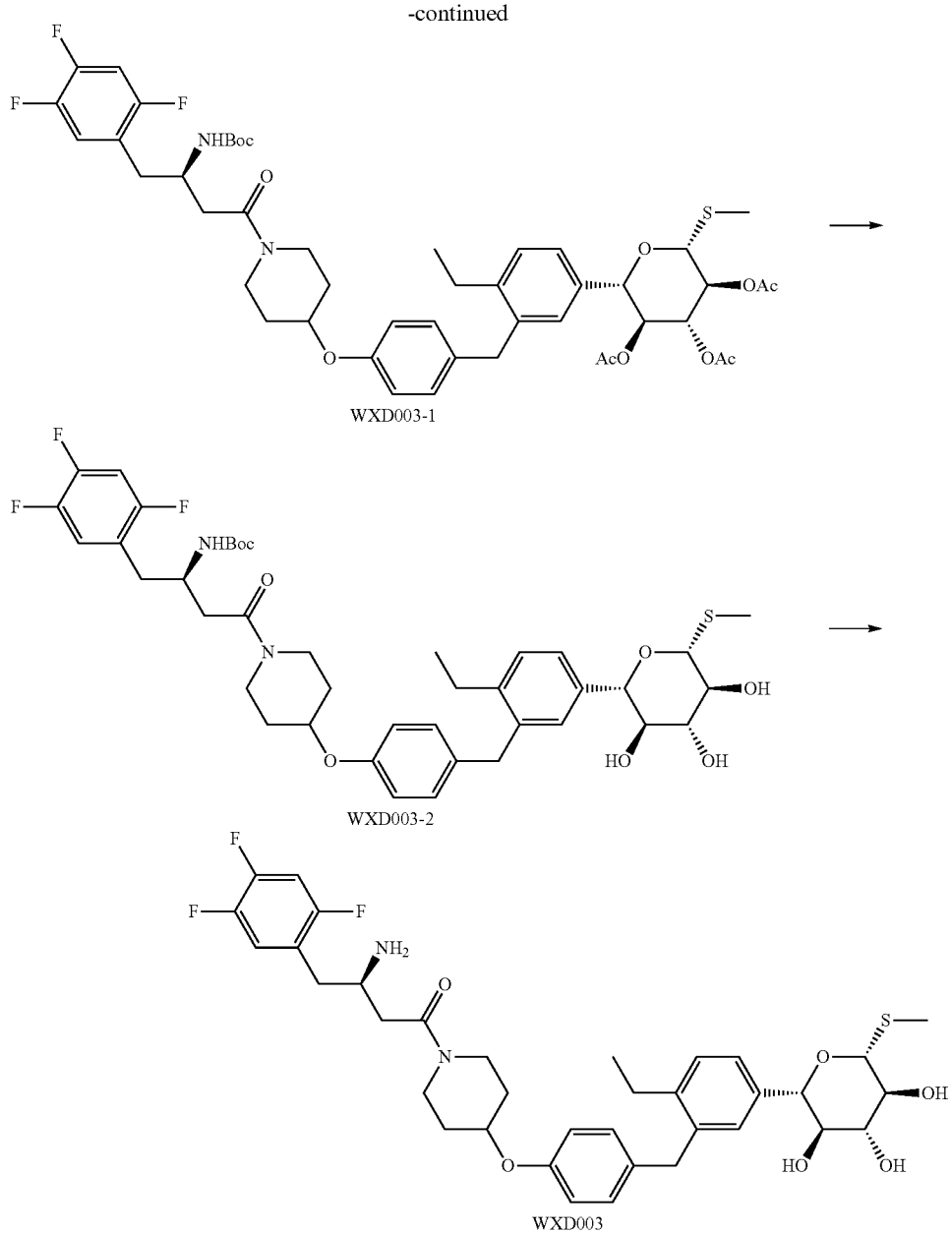

Step 1: Synthesis of WXD003-1

To a reaction flask were firstly added A-2 (319.44 mg, 516.49 μmol, 1.3 eq), B-2 (200 mg, 397.30 μmol, 1 eq), Na₂CO₃ (65.95 mg, 794.59 μmol, 2 eq), and Pd(PPh₃)₄ (91.82 mg, 79.46 μmol, 0.2 eq). The atmosphere was replaced with nitrogen three times, and then toluene (4 mL), EtOH (1 mL), and H₂O (1 mL) were added successively. The mixture was heated to 50° C. and reacted for 16 hours. After the reaction was completed, the reaction solution was rotary-evaporated to dryness. The residue was then diluted with water (30 mL), and extracted with ethyl acetate (100 mL*3). The organic phase was washed with saturated brine (50 mL), dried over anhydrous sodium sulfate, and filtered. The filtrate was rotary-evaporated to dryness. The residue was purified by preparative chromatography plate to give WXD003-1.

Step 2: Synthesis of WXD003-2

WXD003-1 (320 mg, 349.72 μmol, 1 eq) was dissolved in a mixed solvent of MeOH (2 mL), THF (1 mL), and H₂O (2 mL), and LiOH·H₂O (293.48 mg, 6.99 mmol, 20 eq) was added. The mixture was stirred at 25° C. for 1 hour. After the reaction was completed, ethyl acetate (30 mL) was added to the reaction solution. The layers were separated. The organic phase was collected, dried over anhydrous sodium sulfate, and filtered. The filtrate was rotary-evaporated to dryness to give a crude product of WXD003-2, which was directly used in the next reaction.

Step 3: Synthesis of WXD003

WXD003-2 (270 mg, 342.24 μmol, 1 eq) was dissolved in ethyl acetate (5 mL), and HCl/EtOAc (4 M, 5 mL, 58.44 eq)

was added. The mixture was stirred at 25° C. for 1 hour. After the reaction was completed, the reaction solution was directly rotary-evaporated to dryness. The residue was purified by preparative high performance liquid chromatography (chromatographic column: Xtimate C18 150×25 mm×5 μm; mobile phase: [water (0.225% formic acid)-acetonitrile]; B (acetonitrile) %: 25%-55%, 7 min) to give the product WXD003.

Referring to the synthesis method of steps 1 to 3 in Example 2, compound WXD004 in Table 2 below was synthesized using fragment B-1 in place of B-2, compound WXD005 in Table 2 below was synthesized using A-3 in place of A-2, compound WXD006 in Table 2 below was synthesized using fragment B-3 in place of B-2, compound WXD007 in Table 2 below was synthesized using fragment B-4 in place of B-2, compound WXD008 in Table 2 below was synthesized using fragment B-5 in place of B-2, and compound WXD009 in Table 2 below was synthesized using fragment B-6 in place of B-2.

TABLE 2

| Example | Fragment A | Fragment B | Compound | Structure |
|---|---|---|---|---|
| 3 |  A-2 | 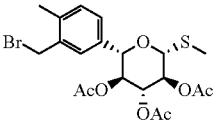 [SMILES: CS[C@H]1O[C@@H](c2ccc(C)c(CBr)c2)[C@H](OC(C)=O)[C@@H](OC(C)=O)[C@@H]1OC(C)=O] B-1 | WXD004 | 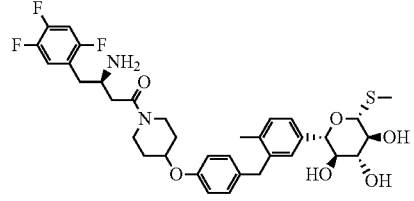 [SMILES: CS[C@H]1O[C@@H](c2ccc(C)c(Cc3ccc(OC4CCN(C(=O)C[C@H](N)Cc5cc(F)c(F)cc5F)CC4)cc3)c2)[C@H](O)[C@@H](O)[C@@H]1O] |
| 4 | 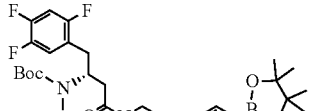 A-2 | 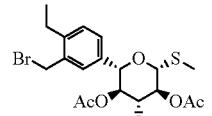 B-2 | WXD005 | 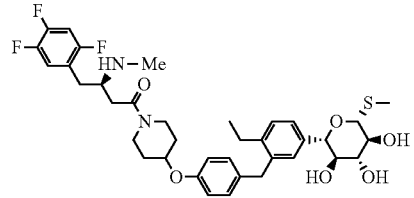 [SMILES: CCc1ccc([C@@H]2O[C@H](SC)[C@@H](O)[C@H](O)[C@H]2O)cc1Cc1ccc(OC2CCN(C(=O)C[C@@H](Cc3cc(F)c(F)cc3F)NC)CC2)cc1] |
| 5 |  A-2 | 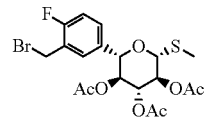 B-3 | WXD006 | 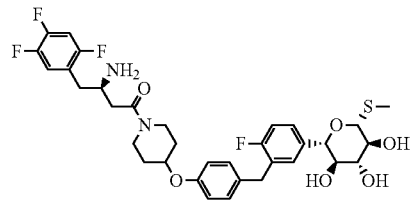 [SMILES: CS[C@H]1O[C@@H](c2ccc(F)c(Cc3ccc(OC4CCN(C(=O)C[C@H](N)Cc5cc(F)c(F)cc5F)CC4)cc3)c2)[C@H](O)[C@@H](O)[C@@H]1O] |
| 6 |  A-2 | 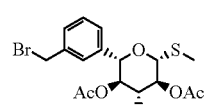 B-4 | WXD007 | 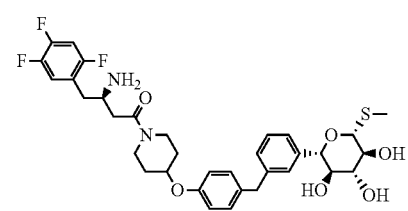 [SMILES: CS[C@H]1O[C@@H](c2cccc(Cc3ccc(OC4CCN(C(=O)C[C@H](N)Cc5cc(F)c(F)cc5F)CC4)cc3)c2)[C@H](O)[C@@H](O)[C@@H]1O] |
| 7 |  A-2 | 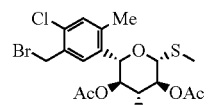 B-5 | WXD008 | 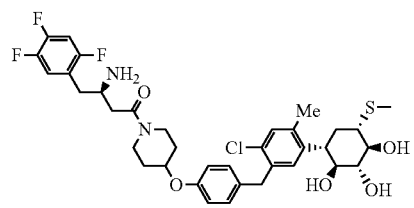 [SMILES: CS[C@H]1C[C@@H](c2cc(Cc3ccc(OC4CCN(C(=O)C[C@H](N)Cc5cc(F)c(F)cc5F)CC4)cc3)c(Cl)cc2C)[C@H](O)[C@@H](O)[C@@H]1O] |
| 8 |  A-2 | 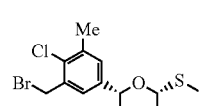 B-6 | WXD009 | 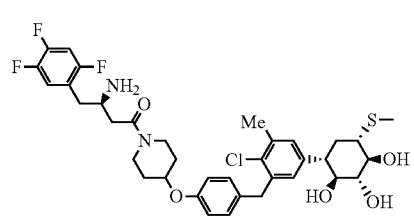 [SMILES: CS[C@H]1C[C@@H](c2cc(C)c(Cl)c(Cc3ccc(OC4CCN(C(=O)C[C@H](N)Cc5cc(F)c(F)cc5F)CC4)cc3)c2)[C@H](O)[C@@H](O)[C@@H]1O] |

The data of ¹H NMR spectrum and mass spectrum of each example were shown in Table 3.

TABLE 3

| Example | Compound | NMR | MS m/z |
|---|---|---|---|
| 1 | WXD001 | ¹H NMR (400 MHz, CD$_3$OD) δ ppm 7.04-7.29 (m, 7 H), 6.77-6.85 (m, 2 H), 4.94-5.05 (m, 1 H), 4.39 (d, J = 9.6 Hz, 1 H), 4.08-4.17 (m, 1 H), 3.97 (d, J = 4.0 Hz, 2 H), 3.35-3.77 (m, 8 H), 2.65-2.83 (m, 2 H), 2.60 (qd, J = 7.2, 2.4 Hz, 2 H), 2.20-2.55 (m, 3 H), 2.06-2.14 (m, 4 H), 1.08 (td, J = 7.6, 2.0 Hz, 3 H). | 675 [M + H]⁺ |
|  | WXD002 | ¹H NMR (400 MHz, CD$_3$OD) δ ppm 7.03-7.30 (m, 7 H), 6.81 (dd, J = 8.8, 4.0 Hz, 2 H), 4.95-5.05 (m, 1 H), 4.39 (dd, J = 9.6, 2.0 Hz, 1 H), 4.13 (dd, J = 9.2, 2.0 Hz, 1 H), 3.92-4.02 (m, 2 H), 3.34-3.74 (m, 8 H), 2.68-2.83 (m, 2 H), 2.60 (qd, J = 7.2, 3.2 Hz, 2 H), 2.29-2.52 (m, 2 H), 2.02-2.27 (m, 5 H), 1.09 (td, J = 7.2, 3.6 Hz, 3 H). | 675 [M + H]⁺ |
| 2 | WXD003 | ¹H NMR (400 MHz, CD$_3$OD) δ ppm 1.09 (t, J = 7.53 Hz, 3 H), 1.62-1.83 (m, 2 H), 1.85-2.04 (m, 2 H), 2.14 (s, 3 H), 2.54-2.68 (m, 3 H), 2.71-2.83 (m, 1 H), 2.99 (d, J = 7.28 Hz, 2 H), 3.34-3.49 (m, 4 H), 3.55-3.89 (m, 4 H), 3.92-4.02 (m, 2 H), 4.13 (d, J = 9.03 Hz, 1 H), 4.39 (d, J = 9.54 Hz, 1 H), 4.54-4.65 (m, 1 H), 6.86 (d, J = 8.53 Hz, 2 H), 7.06 (d, J = 8.53 Hz, 2 H), 7.13-7.38 (m, 5 H), 8.52 (s, 1 H). | 689 [M + H]⁺ |
| 3 | WXD004 | ¹H NMR (400 MHz, CD$_3$OD) δ ppm 1.60-1.82 (m, 2 H), 1.84-2.06 (m, 2 H), 2.14 (s, 3 H), 2.21 (s, 3 H), 2.50-2.65 (m, 1 H), 2.69-2.80 (m, 1 H), 2.95 (br d, J = 7.28 Hz, 2 H), 3.34-3.49 (m, 4 H), 3.50-3.86 (m, 4 H), 3.87-3.97 (m, 2 H), 4.13 (d, J = 9.03 Hz, 1 H), 4.39 (d, J = 9.54 Hz, 1 H), 4.57 (br d, J = 3.51 Hz, 1 H), 6.86 (d, J = 8.53 Hz, 2 H), 7.06 (d, J = 8.53 Hz, 2 H), 7.11-7.26 (m, 4 H), 7.27-7.37 (m, 1 H), 8.54 (s, 1 H). | 675 [M + H]⁺ |
| 4 | WXD005 | ¹H NMR (400 MHz, CD$_3$OD) δ ppm 8.49 (br s, 2 H), 7.31-7.43 (m, 1 H), 7.12-7.30 (m, 4 H), 7.05 (d, J = 8.28 Hz, 2 H), 6.85 (br d, J = 7.03 Hz, 2 H), 4.49-4.63 (m, 1 H), 4.39 (d, J = 9.54 Hz, 1 H), 4.13 (d, J = 9.29 Hz, 1 H), 3.96 (s, 2 H), 3.56-3.89 (m, 4 H), 3.34-3.54 (m, 5 H), 3.20 (br dd, J = 13.80, 5.27 Hz, 1 H), 2.98-3.12 (m, 1 H), 2.76 (s, 5 H), 2.60 (q, J = 7.61 Hz, 2 H), 2.14 (s, 3 H), 1.82-2.00 (m, 2 H), 1.59-1.80 (m, 2 H), 1.08 (t, J = 7.53 Hz, 3 H). | 703 [M + H]⁺ |
| 5 | WXD006 | ¹H NMR (400 MHz, CD$_3$OD) δ ppm 1.75 (br d, J = 14.05 Hz, 2 H), 1.93 (br d, J = 15.56 Hz, 2 H), 2.15 (s, 3 H), 2.40-2.64 (m, 2 H), 2.70-2.91 (m, 2 H), 3.34-3.52 (m, 6 H), 3.66-3.84 (m, 2 H), 3.93-3.96 (m, 2 H), 4.15 (d, J = 9.54 Hz, 1 H), 4.41 (d, J = 9.54 Hz, 1 H), 4.61 (br d, J = 11.80 Hz, 1 H), 6.89 (d, J = 8.78 Hz, 2 H), 7.05 (t, J = 9.03 Hz, 1 H), 7.12-7.20 (m, 3 H), 7.23-7.33 (m, 3 H). | 679 [M + H]⁺ |
| 6 | WXD007 | ¹H NMR (400 MHz, CD$_3$OD) δ ppm 1.72 (br s, 2 H), 1.93 (br d, J = 9.0 Hz, 2 H), 2.14 (s, 3 H), 2.59-2.84 (m, 2 H), 3.01 (br d, J = 6.5 Hz, 2 H), 3.35-3.50 (m, 4 H), 3.52-3.70 (m, 2 H), 3.72-3.84 (m, 2 H), 3.91 (s, 2 H), 4.14 (d, J = 9.3 Hz, 1 H), 4.40 (d, J = 9.8 Hz, 1 H), 4.58 (br s, 1 H), 6.87 (br d, J = 8.3 Hz, 2 H), 7.13 (br d, J = 8.3 Hz, 3 H), 7.19-7.28 (m, 4 H), 7.29-7.38 (m, 1 H), 8.52 (br s, 1 H). | 661 [M + H]⁺ |
| 7 | WXD008 | ¹H NMR (400 MHz, CD$_3$OD) δ ppm 1.64-1.81 (m, 2 H), 1.93 (br d, J = 8.78 Hz, 2 H), 2.11 (s, 3 H), 2.36 (s, 3 H), 2.54-2.66 (m, 1 H), 2.71-2.82 (m, 1 H), 2.99 (d, J = 7.28 Hz, 2 H), 3.35 (br d, J = 9.54 Hz, 2 H), 3.38-3.45 (m, 1 H), 3.45-3.51 (m, 2 H), 3.51-3.63 (m, 1 H), 3.63-3.86 (m, 3 H), 4.00 (s, 2 H), 4.41 (d, J = 9.54 Hz, 1 H), 4.45 (d, J = 9.03 Hz, 1 H), 4.58 (br d, J = 2.76 Hz, 1 H), 6.87 (d, J = 8.53 Hz, 2 H), 7.12 (d, J = 8.53 Hz, 2 H), 7.17-7.25 (m, 2 H), 7.26 (s, 1 H), 7.28-7.37 (m, 1 H), 8.51 (br s, 1 H). | 709 [M + H]⁺ |
| 8 | WXD009 | ¹H NMR (400 MHz, CD$_3$OD) δ ppm 1.64-1.81 (m, 2H), 1.86-2.02 (m, 2H), 2.15 (s, 3H), 2.40 (s, 3H), 2.42-2.60 (m, 2H), 2.70-2.88 (m, 2H), 3.34-3.41 (m, 2H), 3.42-3.62 (m, 4H), 3.66-3.88 (m, 2H), 4.06 (d, J = 3.01 Hz, 2H), 4.08-4.15 (m, 1H), 4.40 (d, J = 9.54 Hz, 1H), 4.58 (br dd, J = 6.90, 3.39 Hz, 1H), 6.88 (d, J = 8.53 Hz, 2H), 7.10-7.20 (m, 4H), 7.22 (s, 1H), 7.29 (ddd, J = 10.85, 8.97, 7.03 Hz, 1H). | 709 [M + H]⁺ |

Assay Example 1. In Vitro Cell Activity Assay

Biological Activity Assay 1: SGLT1 Glucose Transport Assay

1. Purpose of the Assay

The effect of the compounds on the glucose transport activity of the SGLT1 transporter was detected by measuring the amount of [$^{14}$C]-labeled glucose entering cells highly expressing Human-SGLT1.

2. Method of the Assay 2.1. Cell Preparation

The cells stably expressing Human-SGLT1 used in the assay were constructed by Shanghai WuXi AppTec. The SGLT1 cells were plated on a Cytostar-T (PerkinElmer) 96-well cell culture plate and cultured at 5% $CO_2$, 37° C. overnight.

2.2. SGLT1 Glucose Transport Assay

1) Assay buffer: 10 mM HEPES buffer (Sigma), 1.2 mM $MgCl_2$, 4.7 mM KCl, 2.2 mM $CaCl_2$) and 120 mM NaCl.
2) The compound with a starting concentration of 1 mM was serially diluted 5-fold with 100% DMSO to 8 concentrations.
3) 3 μM [$^{14}$C]Methyl α-D-glucopyranoside (labeled methyl α-D-glucopyranoside) was prepared with the assay buffer.
4) The cells were treated with 49 μL of the assay buffer, 1 μL of the serially diluted compound, and 50 μL of the 3 μM [$^{14}$C] isotope-labeled sugar solution at 37° C. for 2 hours.
5) An isotope detector (Micro beta Reader) was used to read.
6) The data were processed by GraphPad Prism 5.0 software with the calculation formula: log(inhibitor) vs. response—Variable slope to give the $IC_{50}$ value of the test compound.

Biological Activity Assay 2: SGLT2 Glucose Transport Assay

1. Purpose of the Assay

The effect of the compound on the glucose transport activity of the SGLT2 transporter was detected by measuring the amount of [$^{14}$C]-labeled glucose entering cells highly expressing Human-SGLT2.

2. Method of the Assay 2.1. Cell Preparation

The cells stably expressing Human-SGLT2 used in the assay were constructed by Shanghai WuXi AppTec. The SGLT2 cells were plated on a 96-well cell culture plate (Greiner) and cultured at 5% $CO_2$, 37° C. overnight.

2.2. SGLT2 Glucose Transport Assay

1) Assay buffer: 10 mM HEPES, 1.2 mM $MgCl_2$, 4.7 mM KCl, 2.2 mM $CaCl_2$ and 120 mM NaCl.
2) Stop buffer: 10 mM HEPES, 1.2 mM $MgCl_2$, 4.7 mM KCl, 2.2 mM $CaCl_2$, 120 mM NaCl and 1 μM LX4211.
3) The compound with a starting concentration of 10 μM was serially diluted 5-fold with 100% DMSO to 8 concentrations.
4) 6 μM [$^{14}$C]Methyl a-D-glucopyranoside was prepared with the assay buffer.
5) The cells were treated with 49 μL of the assay buffer, 1 μL of the serially diluted compound, and 50 μL of the 6 μM [$^{14}$C] isotope-labeled sugar solution at 37° C. for 2 hours.
6) The liquid in the well was aspirated and the cells were rinsed three times with the stop buffer.
7) The cells were lysed with 50 μL of 10% sodium hydroxide solution, the cell lysate was pipetted into a scintillation tube, and 2 mL of scintillation fluid was added.
8) An isotope detector (Tricarb) was used to read.
9) The data were processed by GraphPad Prism 5.0 software with the calculation formula: log(inhibitor) vs. response—Variable slope to give the $IC_{50}$ value of the test compound.

The assay results were shown in Table 4:

TABLE 4

Results of the in vitro cell activity assay

| Compound | Human-SGLT1 $IC_{50}$ (nM) | Human-SGLT2 $IC_{50}$ (nM) |
| --- | --- | --- |
| LX2761 | 1.1 | 1.1 |
| WXD001 | 0.7 | 6.5 |
| WXD002 | 0.5 | 2.9 |
| WXD003 | 0.7 | 0.6 |
| WXD004 | 0.8 | 0.8 |
| WXD005 | 3.5 | 1.4 |
| WXD006 | 35 | 1.4 |
| WXD007 | 69 | 5.8 |
| WXD008 | 21 | 1.5 |
| WXD009 | 50 | 3.3 |

Conclusion: The compounds of the present disclosure exhibit excellent in vitro inhibitory activity on Human-SGLT1 and Human-SGLT2.

Assay Example 2. In Vivo DMPK Study

In Vivo DMPK Study in Rats

Purpose of the assay: Male SD rats were used as test animals to determine the blood concentration of the compound after a single administration and evaluate the pharmacokinetic behavior.

Procedure of the assay: 4 healthy adult male SD rats were selected, 2 rats in the intravenous injection group, and 2 rats in the oral group. The test compound was mixed with an appropriate amount of vehicle (10% NMP/10% solutol/80% water) for the intravenous injection group, vortexed, and sonicated to prepare a clear solution of 0.5 mg/mL. The clear solution was filtered by a microporous membrane for use. The vehicle for the oral group was 10% NMP/10% solutol/80% water. The test compound was mixed with the vehicle, and then the mixture was vortexed and sonicated to prepare a clear solution of 1 mg/mL. Rats were administered 1 mg/kg intravenously or 10 mg/kg orally, and then whole blood was collected for a certain period. Plasma was prepared. The drug concentration was analyzed by LC-MS/MS method, and the pharmacokinetic parameters were calculated by Phoenix WinNonlin software (Pharsight, USA).

Note: NMP: N-methylpyrrolidone; solutol: polyethylene glycol-15 hydroxystearate.

The assay results were shown in Table 5:

TABLE 5

Results of PK assay of the compounds

| Compound | $C_{max}$ (nM) | F % | Oral DNAUC (nM·h/mpk) | $Vd_{SS}$ (L/kg) | Cl (mL/min/kg) | $T_{1/2}$ (h) |
|---|---|---|---|---|---|---|
| LX2761 | ND | ND | ND | 1.4 | 37.6 | 1.9 |
| WXD003 | 16.5 | 0.2 | 2 | 1.5 | 32.5 | 2.3 |

Note:
$C_{max}$ is maximum concentration; F % is oral bioavailability; DNAUC = $AUC_{PO}$/Dose, $AUC_{PO}$ is oral exposure, Dose is drug dose; $Vd_{SS}$ is distribution volume; Cl is clearance rate; $T_{1/2}$ is half-life; and ND means not detected.

Conclusion: The compound of the present disclosure exhibits low oral exposure and bioavailability, and exhibits desirable pharmacokinetic properties as a SGLT1 selective inhibitor.

Assay Example 3. In Vivo Efficacy Study

I. In Vivo Efficacy Study of Oral Glucose Tolerance in Rats (OGTT)

1. Assay Animals

| Animals | Species | SD rats | Gender | male |
|---|---|---|---|---|
| | Weeks of age / weight | About 8 weeks old/250 g | Supplier | Shanghai SLAC |
| Animal feed | Ordinary rat and mouse feed | | | |

2. Assay Grouping

TABLE 6

Assay grouping information

| Group | Compound grouping | dosage | Frequency of administration | Mode of administration | Number of animals in each group |
|---|---|---|---|---|---|
| 1 | Vehicle control group | — | Single administration | Gavage | 5 |
| 2 | WXD003 | 5 mg/kg | Single administration | Gavage | 5 |

3. Assay Process

1) Animal Adaptation and Preparation

After the assay animals arrived at the facility, they needed to adapt to the environment in the animal room for 1 week.

2) Fasting and Administration

After the animals were fasted for 6 hours, they were administered WXD003 or vehicle according to Table 6, and then immediately administered 50% glucose solution (2 g/kg, 4 ml/kg).

3) Blood Glucose Test

The time for sugar administration was recorded as 0 point. The blood glucose of the animals was detected at 0 minute before sugar administration, and at 15, 30, 60, 90, 120 minutes after sugar administration, respectively. A curve of glucose tolerance was drawn based on the data of time versus blood glucose, and the area under curve (AUC) was calculated.

4) Data Analysis

All values were expressed as average values. Statistical analysis was evaluated using Graphpad Prism 6 one-way analysis of variance and Tukey's multiple comparison test. A p value of less than 0.05 was considered statistically significant.

4. Assay Results

TABLE 7

Results of in vivo efficacy assay of glucose tolerance in rats

| Compound | Vehicle control group | WXD003 |
|---|---|---|
| OGTT blood glucose level $AUC_{0-2\ hours}$ (mmol/L × min) | 1063.4 | 624.2**** |

Note:
****means p < 0.0001 relative to the vehicle control group.

Conclusion: Compared with the vehicle control group, the administration group can significantly reduce the blood glucose AUC level of the animals within 2 hours.

II. In Vivo Efficacy Study in Diabetic Mouse Model Induced by STZ Combined with High-Sugar and High-Fat Diet 1. Assay Animals 7 week-old C57BL/6J male mice, purchased from Jiangsu GemPharmatech Co., Ltd.

2. Assay Process

1) After the animals adapted to the environment, all mice were divided into two groups according to body weight, fed according to the scheme in Table 8, and injected with vehicle and streptozotocin (STZ) for modeling;

TABLE 8

Grouping information of STZ modeling assay

| Group | Mouse strain | Quantity | Feed | STZ modeling treatment |
|---|---|---|---|---|
| Normal group (Ordinary rat and mouse feed) | C57BL/6J | 5 | Chow Diet | Intraperitoneally injected with citrate buffer (pH = 4.5) for 5 days |
| Model group (STZ + high-sugar and high-fat feed) | C57BL/6J | 50 | High-sugar and high-fat feed (Research Diet, HFHS, D12451) | Intraperitoneally injected with citrate buffer (pH = 4.5) and STZ (dose: 40 mg/kg) for 5 days |

2) According to the random blood glucose test results of the model group, mice with random blood glucose greater than 11 mmol/L were enrolled in the group to continue the administration assay;

3) The mice in the model group that meet the criteria for enrollment were divided into 3 groups, 5 in the normal group, and 10 in each model administration group. The mice were administered according to the administration schedule in Table 9;

TABLE 9

Grouping information of the assay

| Group | Dosage (Week 1 to Week 4) | Dosage (Week 4 to Week 7) | Mode and frequency of administration |
|---|---|---|---|
| The normal group | Vehicle + Chow diet | Vehicle + Chow diet | Orally, once a day |
| The model administration group 1 | Vehicle + HFHS | Vehicle + HFHS | Orally, once a day |
| The model administration group 2 | WXD003 (3 mg/kg) + HFHS | WXD003 (6 mg/kg) + HFHS | Orally, once a day |

4) After starting the administration, the level of change in animal weight was monitored every day, and the blood glucose and glycosylated hemoglobin of the mice in each group after 6 hours of fasting were detected after 4 weeks and 7 weeks of administration, respectively;

5) Data analysis: All values were expressed as average values. Statistical analysis was evaluated using Graphpad Prism 6 one-way analysis of variance and Tukey's multiple comparison test, and a p value of less than 0.05 was considered statistically significant.

3. Assay Results

1) Assay Results after 4 Weeks of Administration:
  a) As shown in Table 10 and FIG. 1, after 4 weeks of administration, WXD003 can significantly reduce the blood glucose level of animals after 6 hours of fasting;

TABLE 10

The blood glucose of animals after 4 weeks of administration

Figure 2:
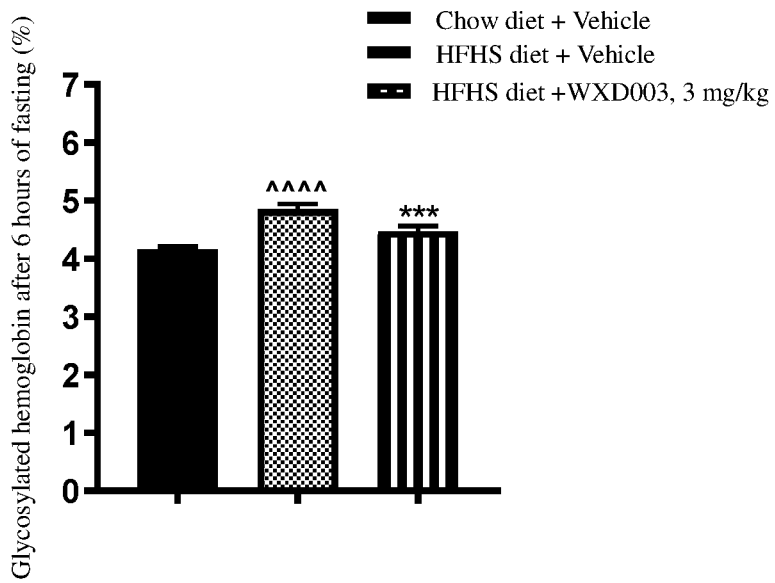
FIG. 2 shows the level of glycosylated hemoglobin of animals after 4 weeks of administration.

| Compound | Chow diet + Vehicle | HFHS + Vehicle | HFHS + WXD003 (3 mg/kg) |
|---|---|---|---|
| Blood glucose after 6 hours of fasting (mmol/L) | 7.2 | 13.7^^^^ | 10.3*** | b) As shown in Table 11 and FIG. 2, after 4 weeks of administration, WXD003 can significantly reduce the level of glycosylated hemoglobin of animals after 6 hours of fasting;

TABLE 11

The glycosylated hemoglobin of animals after 4 weeks of administration

Figure 3:
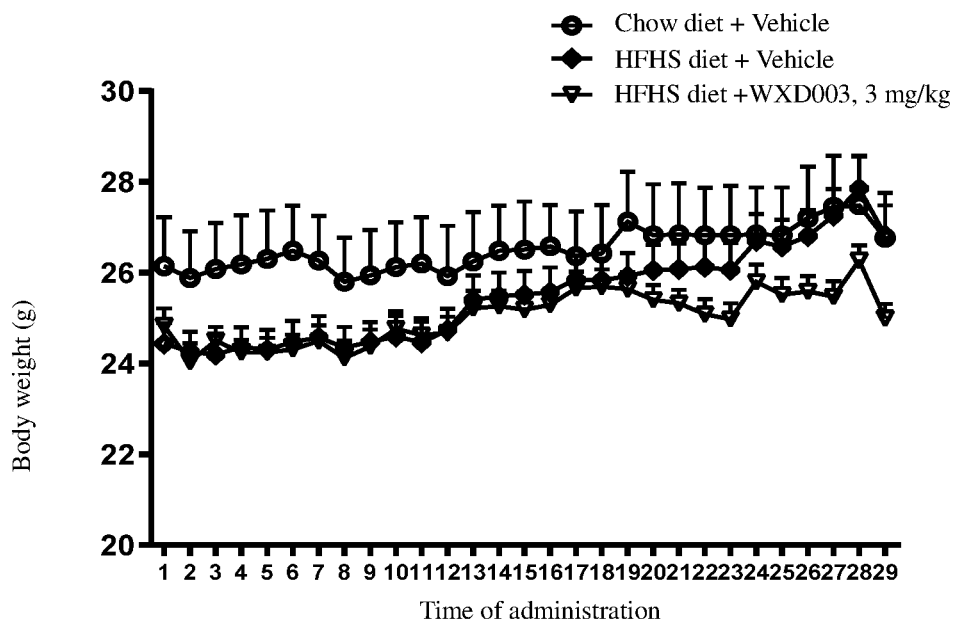
FIG. 3 shows the level of change in animal weight after 4 weeks of administration.

| Compound | Chow diet + Vehicle | HFHS + Vehicle | HFHS + WXD003 (3 mg/kg) |
|---|---|---|---|
| Glycosylated hemoglobin after 6 hours of fasting (%) | 4.2 | 4.9^^^^ | 4.5*** | c) As shown in FIG. 3, after 4 weeks of administration, WXD003 can effectively control the weight gain of animals.

Figure 4:
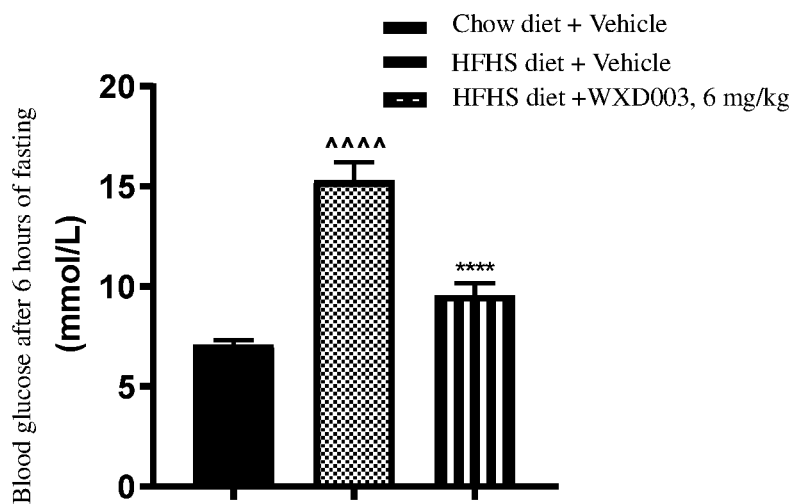
FIG. 4 shows the blood glucose level of animals after 7 weeks of administration.

2) Assay Results after 7 Weeks of Administration
  d) As shown in Table 12 and FIG. 4, after 7 weeks of administration, WXD003 can significantly reduce the blood glucose level of animals after 6 hours of fasting. WXD003 can further reduce the blood glucose level of animals after 6 hours of fasting after 7 weeks of administration compared with that after 4 weeks of administration;

TABLE 12

The blood glucose of animals after 7 weeks of administration

Figure 5:
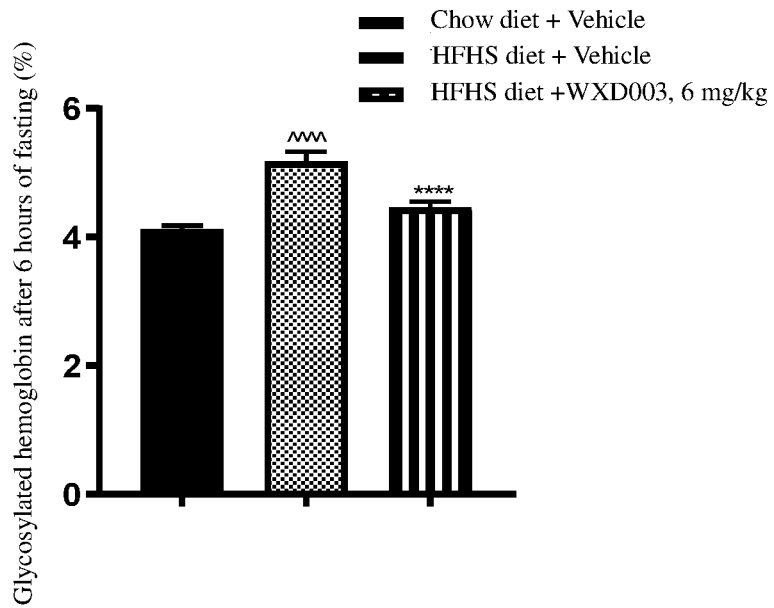
FIG. 5 shows the level of glycosylated hemoglobin of animals after 7 weeks of administration.

| Compound | Chow diet + Vehicle | HFHS + Vehicle | HFHS + WXD003 (6 mg/kg) |
|---|---|---|---|
| Blood glucose after 6 hours of fasting (mmol/L) | 7.1 | 15.3^^^^ | 9.6**** | e) As shown in Table 13 and FIG. 5, after 7 weeks of administration, WXD003 can significantly reduce the level of glycosylated hemoglobin of animals after 6 hours of fasting;

TABLE 13

The glycosylated hemoglobin of animals after 7 weeks of administration

Figure 6:
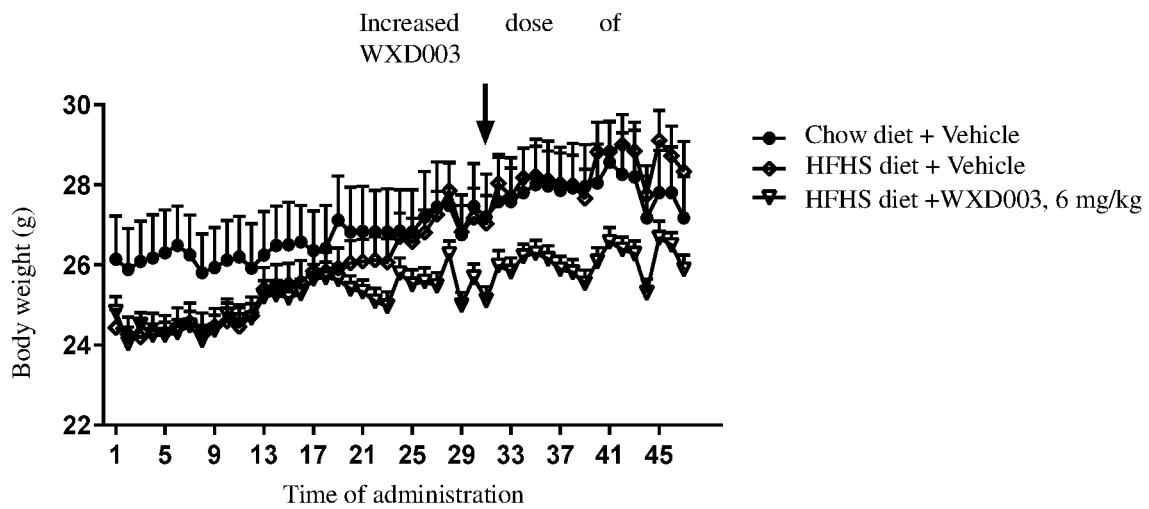
FIG. 6 shows the level of change in animal weight after 7 weeks of administration.

| Compound | Chow diet + Vehicle | HFHS + Vehicle | HFHS + WXD003 (6 mg/kg) |
|---|---|---|---|
| Glycosylated hemoglobin after 6 hours of fasting (%) | 4.1 | 5.2^^^^ | 4.4**** | f) As shown in FIG. 6, after 7 weeks of administration, WXD003 can effectively control the weight gain of animals.

Note: ^^^^ means p<0.0001 relative to the vehicle group with chow diet, * means p<0.05 relative to the vehicle group with HFHS diet,  means p<0.01 relative to the vehicle group with HFHS diet, * means p<0.001 relative to the vehicle group with HFHS diet, and **** means p<0.0001 relative to the vehicle group with HFHS diet.

Conclusion: Compared with the vehicle control group with HFHS diet, the administration group can significantly reduce the blood glucose and glycosylated hemoglobin of animals after 6 hours of fasting, and can effectively control the weight gain of animals.

III. In Vivo Efficacy Study in Obese Mouse Model Induced by HFHS Diet

1. Assay Animals 5 week-old C57BL/6J male mice, purchased from Jiangsu GemPharmatech Co., Ltd.

2. Assay Process

1) After the animals adapted to the environment, they were fed a HFHS diet (Research Diet, HFHS, D12451) for 20 weeks, and then mice weighing more than 40 grams were selected for weight loss assay.

2) Animals whose body weight met the standard were adapted for vehicle administration, and then all mice were divided into 5 groups according to body weight for weight loss assay. The effect of the compound in reducing the body weight of animals was detected. The assay grouping was shown in Table 14:

TABLE 14

| Grouping information of the assay | | |
|---|---|---|
| Group | Dosage | Mode and frequency of administration |
| Vehicle group 1 | Chow Diet + Vehicle | Orally, once a day |
| Vehicle group 2 | HFHS + Vehicle | Orally, once a day |
| Administration group 3 | HFHS + WXD003 (0.3 mg/kg) | Orally, once a day |
| Administration group 4 | HFHS + WXD003 (1 mg/kg) | Orally, once a day |
| Administration group 5 | HFHS + WXD003 (3 mg/kg) | Orally, once a day |

3) After starting the administration, the level of change in animal weight was monitored every day, and after 3 weeks of administration, the blood glucose levels of mice in each group after 6 hours of fasting and 1 hour after meal were detected, respectively;

4) Data analysis: All values were expressed as average values. Statistical analysis was evaluated using Graphpad Prism 6 one-way analysis of variance and Tukey's multiple comparison test, and a p value of less than 0.05 was considered statistically significant.

3. Assay Results

Figure 7:
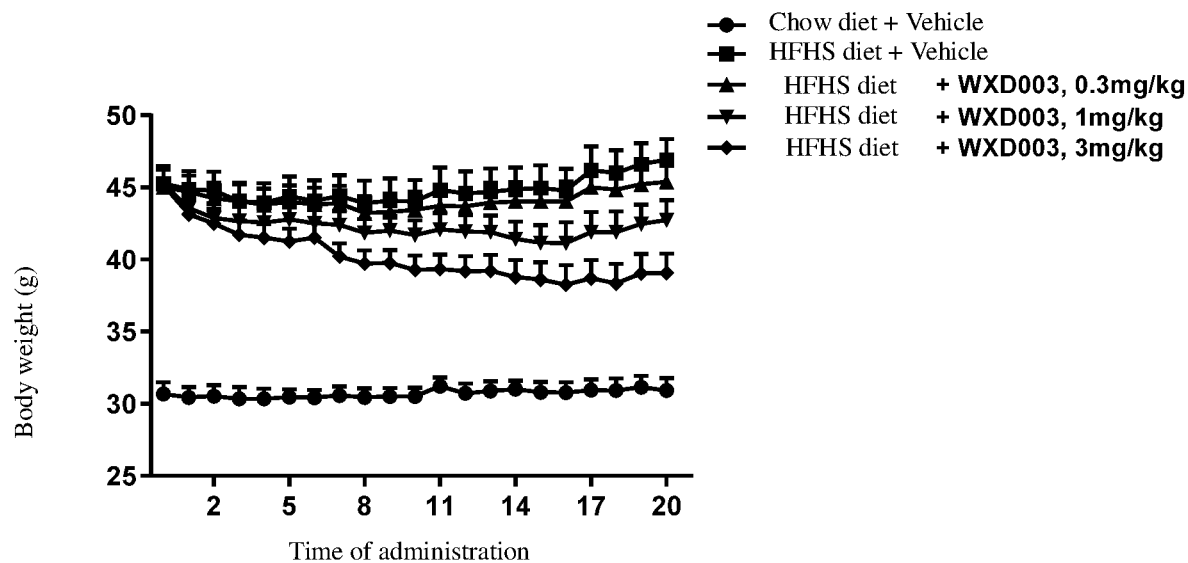
FIG. 7 shows the level of change in animal weight after 3 weeks of administration.
Figure 8:
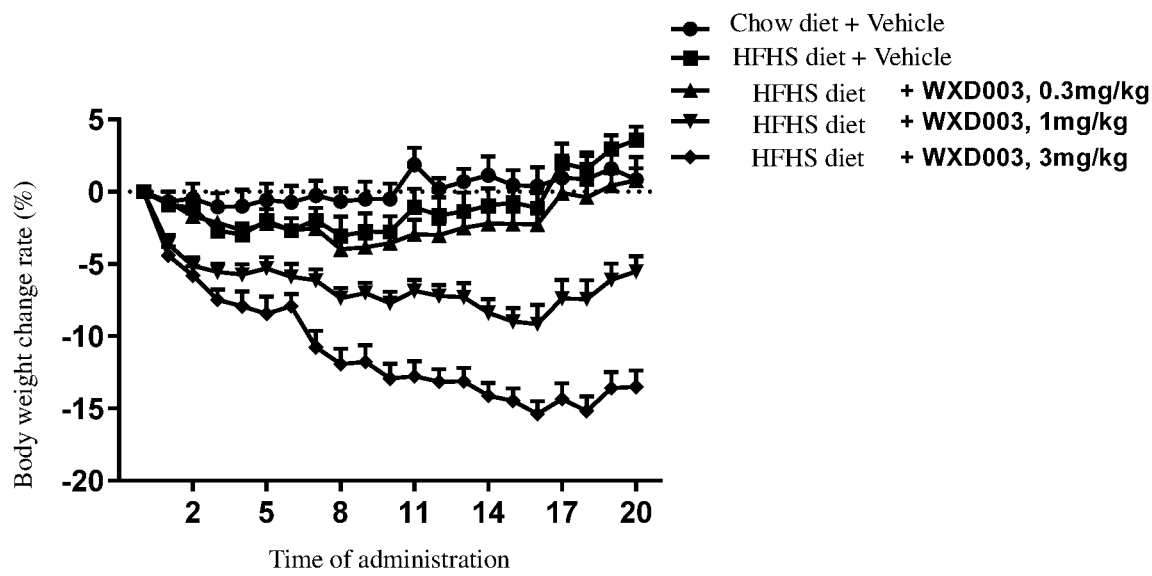
FIG. 8 shows the rate of change in animal weight after 3 weeks of administration.
Figure 9:
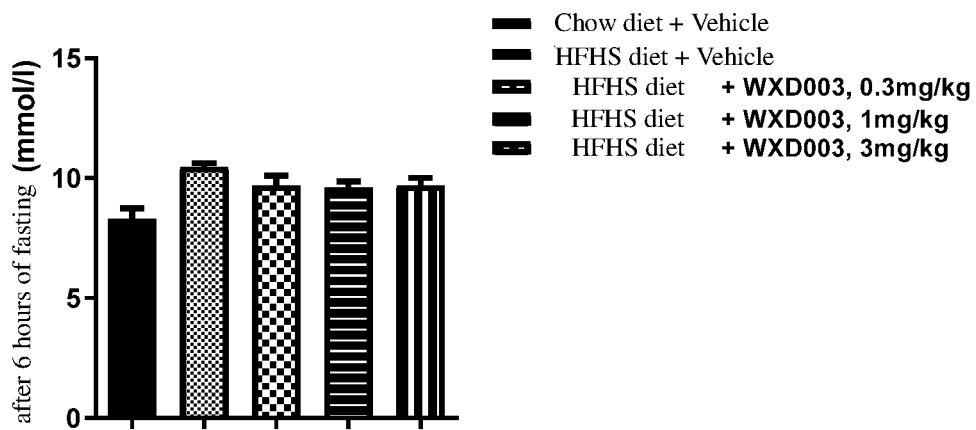
FIG. 9 shows the blood glucose of animals after 6 hours of fasting after 3 weeks of administration.

1) As shown in FIG. 7 and FIG. 8, after 3 weeks of administration, WXD003 can significantly reduce animal weight in a dose-dependent manner;

2) As shown in Table 15 and FIG. 9, after 3 weeks of administration, WXD003 can reduce the blood glucose of animals after 6 hours of fasting.

TABLE 15

The blood glucose of animals after 6 hours of fasting after 3 weeks of administration

| Compound | Chow diet + Vehicle | HFHS + Vehicle | HFHS + WXD003 (0.3 mg/kg) | HFHS + WXD003 (1 mg/kg) | HFHS + WXD003 (3 mg/kg) |
|---|---|---|---|---|---|
| Blood glucose after 6 hours of fasting (mmol/L) | 8.3 | 10.5 | 9.7 | 9.6 | 9.7 |

Figure 10:
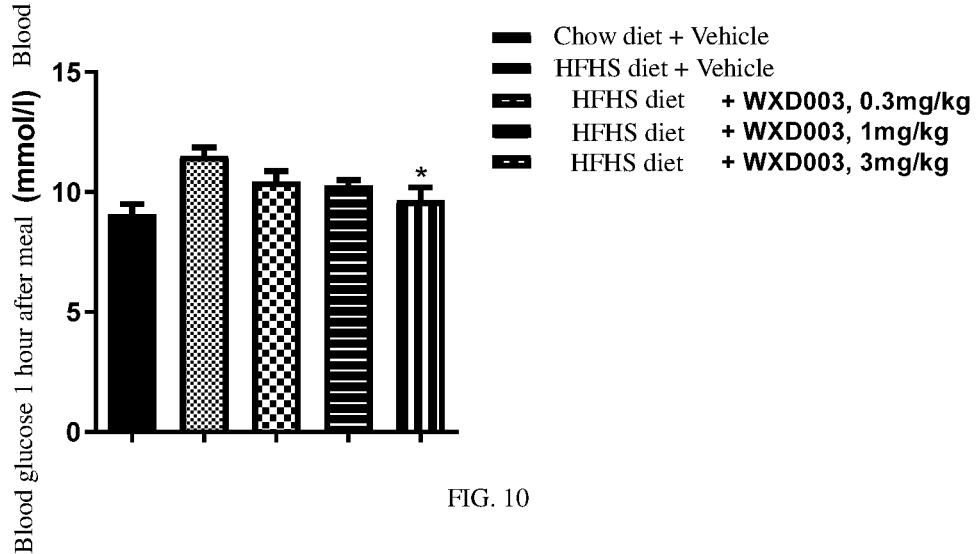
FIG. 10 shows the blood glucose of animals 1 hour after meal after 3 weeks of administration.

3) As shown in Table 16 and FIG. 10, after 3 weeks of administration, WXD003 can reduce the blood glucose of animals 1 hour after meal.

TABLE 16

The blood glucose of animals 1 hour after meal after 3 weeks of administration

| Compound | Chow diet + Vehicle | HFHS + Vehicle | HFHS + WXD003 (0.3 mg/kg) | HFHS + WXD003 (1 mg/kg) | HFHS + WXD003 (3 mg/kg) |
|---|---|---|---|---|---|
| Blood glucose 1 hour after meal (mmol/L) | 9.1 | 11.5 | 10.5 | 10.2 | 9.6* |

Note:
*means p < 0.05 relative to the vehicle group with HFHS diet,
** means p < 0.01 relative to the vehicle group with HFHS diet,
*** means p < 0.001 relative to the vehicle group with HFHS diet,
and **** means p < 0.0001 relative to the vehicle group with HFHS diet.

Conclusion: Compared with the vehicle control group with HFHS diet, the administration group can significantly reduce the body weight of animals in a dose-dependent manner, and can also reduce the blood glucose of animals after 6 hours of fasting and 1 hour after meal.

What is claimed is:

1. A compound represented by formula (II), or a stereoisomer, a tautomer, or a pharmaceutically acceptable salt thereof,

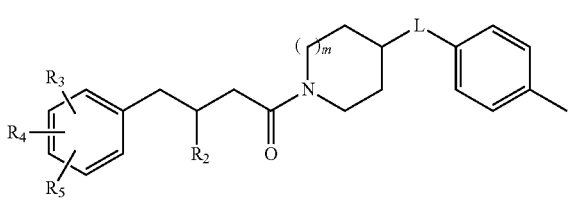

-continued

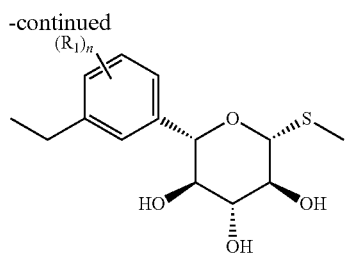

wherein
- $R_1$ is selected from H, F, Cl, Br, I, OH, $NH_2$, CN, $C_{1-6}$ alkyl and $C_{1-6}$ alkoxy, wherein the $C_{1-6}$ alkyl and $C_{1-6}$ alkoxy are optionally substituted with 1, 2, or 3 $R_a$;
- $R_2$ is selected from F, Cl, Br, I, OH, $NH_2$ and $C_{1-3}$ alkylamino;
- $R_3$, $R_4$ and $R_5$ are each independently selected from H, F, Cl, Br, I, OH, $NH_2$, CN, and $C_{1-3}$ alkyl optionally substituted with 1, 2, or 3 $R_b$;
- L is selected from single bond, —O—, —S—, —C($R_c$)$_2$—, and —N($R_d$)—;
- m is selected from 0, 1, and 2;
- n is selected from 1, 2, and 3;
- $R_a$, $R_b$ and $R_c$ are each independently selected from F, Cl, Br, I, OH, $NH_2$ and $CH_3$;
- $R_d$ is selected from H and $CH_3$.

2. The compound, or stereoisomer, tautomer, or pharmaceutically acceptable salt thereof according to claim 1, wherein $R_1$ is selected from H, F, Cl, Br, I, OH, $NH_2$, CN, $CH_3$, $CH_2CH_3$, and —$OCH_3$, wherein the $CH_3$, $CH_2CH_3$, and —$OCH_3$ are optionally substituted with 1, 2, or 3 $R_a$.

3. The compound, or stereoisomer, tautomer, or pharmaceutically acceptable salt thereof according to claim 2, wherein $R_1$ is selected from H, F, Cl, Br, I, OH, $NH_2$, CN, $CH_3$, $CH_2F$, $CHF_2$, $CF_3$, $CH_2CH_3$, and —$OCH_3$.

4. The compound, or stereoisomer, tautomer, or pharmaceutically acceptable salt thereof according to claim 1, wherein $R_2$ is selected from F, Cl, Br, I, OH, $NH_2$, $NH(CH_3)$, and $N(CH_3)_2$.

5. The compound, or stereoisomer, tautomer, or pharmaceutically acceptable salt thereof according to claim 1, wherein $R_3$, $R_4$ and $R_5$ are each independently selected from H, F, Cl, Br, I, OH, $NH_2$, CN, and $CH_3$ optionally substituted with 1, 2, or 3 $R_b$.

6. The compound, or stereoisomer, tautomer, or pharmaceutically acceptable salt thereof according to claim 5, wherein $R_3$, $R_4$ and $R_5$ are each independently selected from H, F, Cl, Br, I, OH, $NH_2$, CN, $CH_3$, $CH_2F$, $CHF_2$, and $CF_3$.

7. The compound, or stereoisomer, tautomer, or pharmaceutically acceptable salt thereof according to claim 1, wherein L is selected from single bond, —O—, and —S—.

8. The compound, or stereoisomer, tautomer, or pharmaceutically acceptable salt thereof according to claim 1, wherein moiety

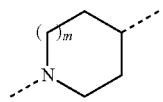

is selected from

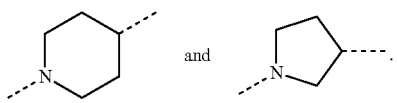

9. The compound, or stereoisomer, tautomer, or pharmaceutically acceptable salt thereof according to claim 1, wherein moiety

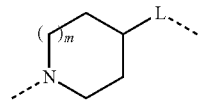

is selected from

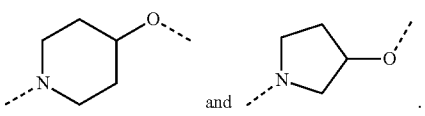

10. The compound, or stereoisomer, tautomer, or pharmaceutically acceptable salt thereof according to claim 1, wherein the compound is selected from the group consisting of:

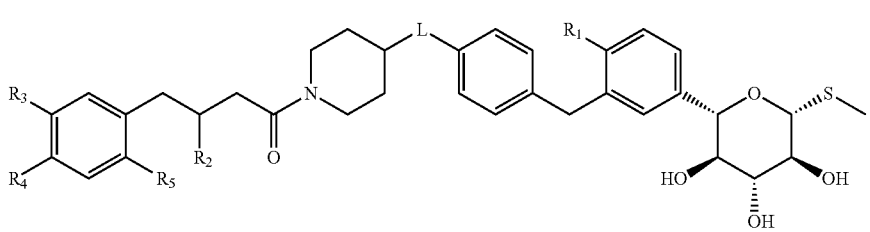

(I-1)

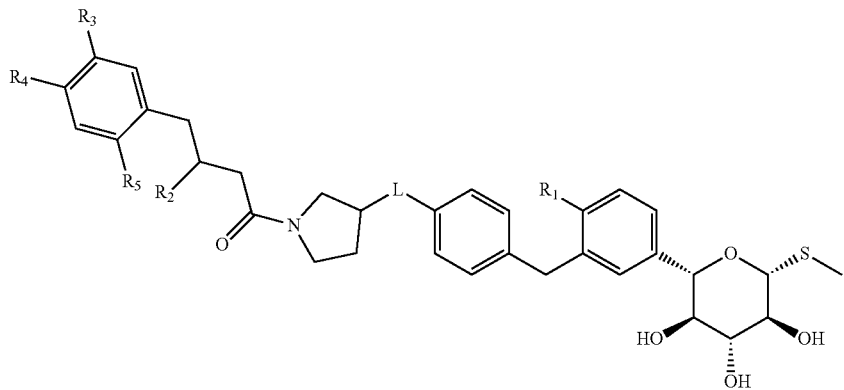
(I-3)
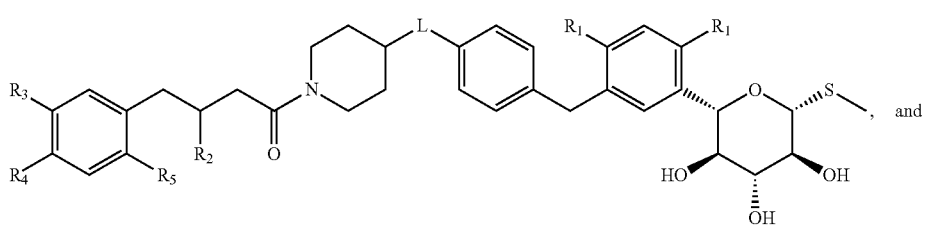
(II-1)
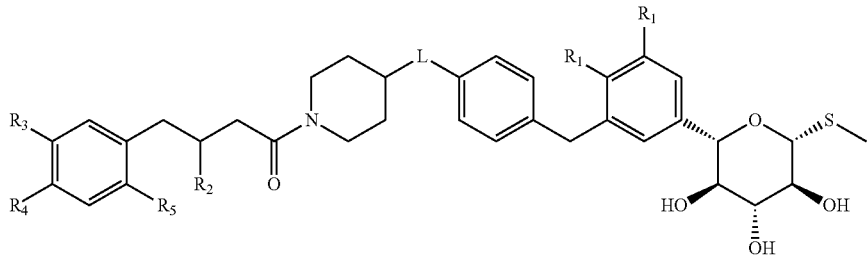
(II-2)
wherein
$R_1$, $R_2$, $R_3$, $R_4$, $R_5$, and L are as defined in claim 1.
11. The compound, or stereoisomer, tautomer, or pharmaceutically acceptable salt thereof according to claim 10, wherein the compound is selected from the group consisting of:
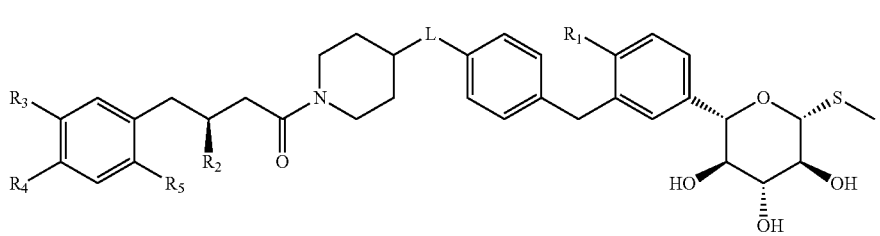
(I-1a)
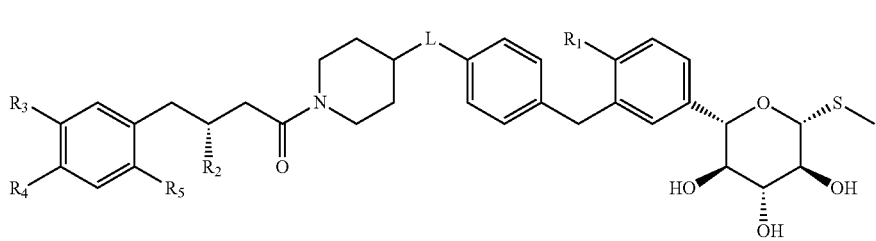
(I-1b)

-continued
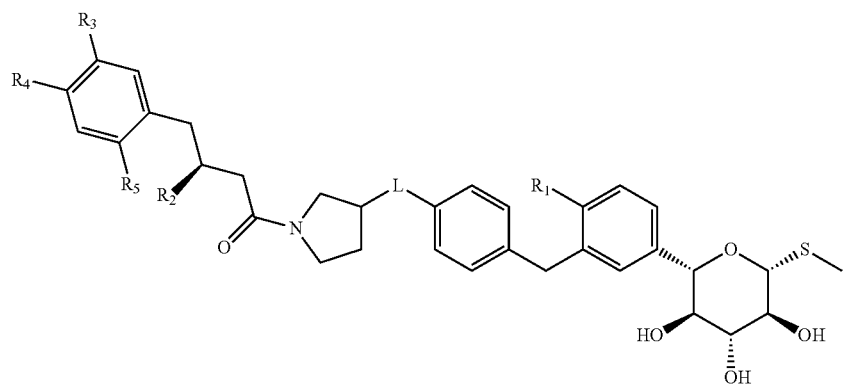
(I-3a)
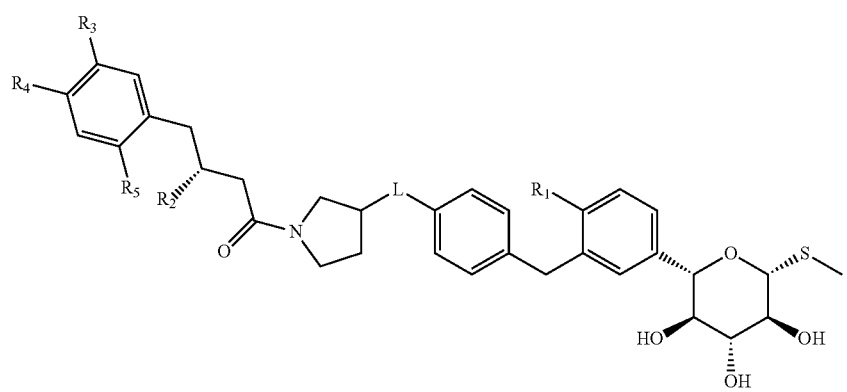
(I-3b)
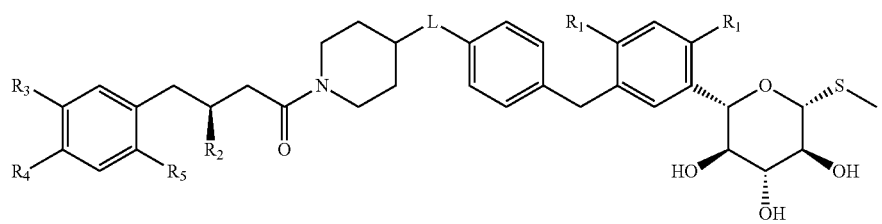
(II-1a)
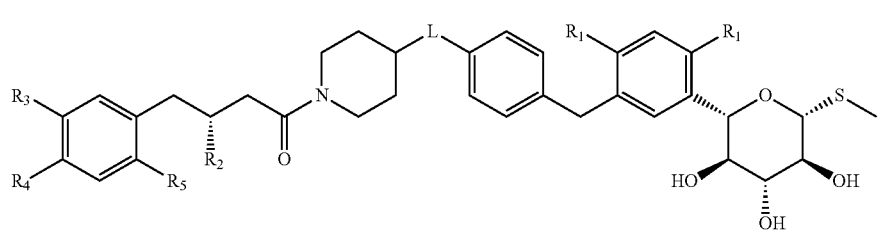
(II-1b)
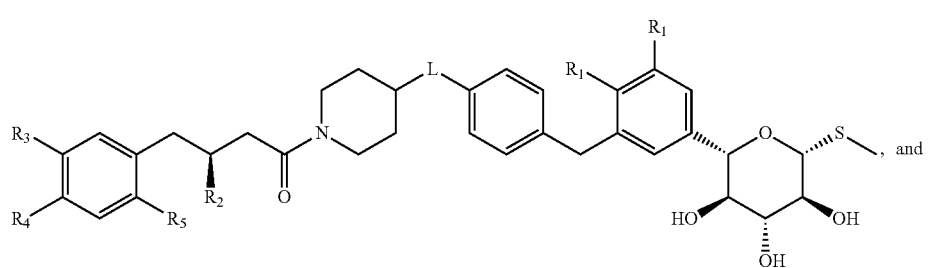
(II-2a)
, and

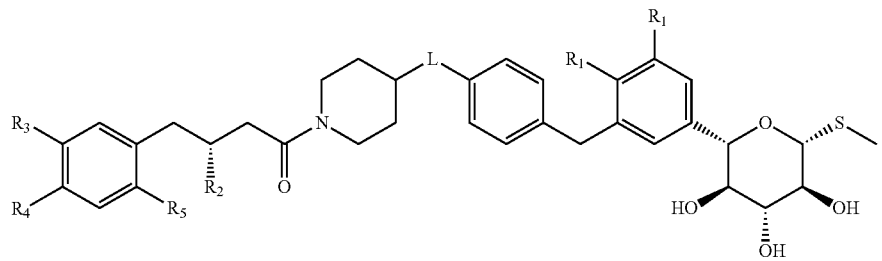
(II-2b)
wherein
R₂ is selected from the group consisting of F, Cl, Br, I, OH, NH₂, NH(CH₃), and N(CH₃)₂;
R₁, R₃, R₄, R₅, and L are as defined in claim 10.
12. The compound, or stereoisomer, tautomer, or pharmaceutically acceptable salt thereof according to claim 11, wherein the compound is selected from the group consisting of:
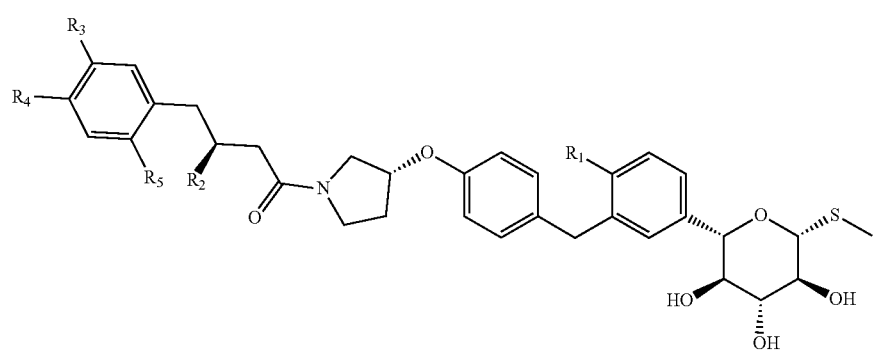
(I-3a-1)
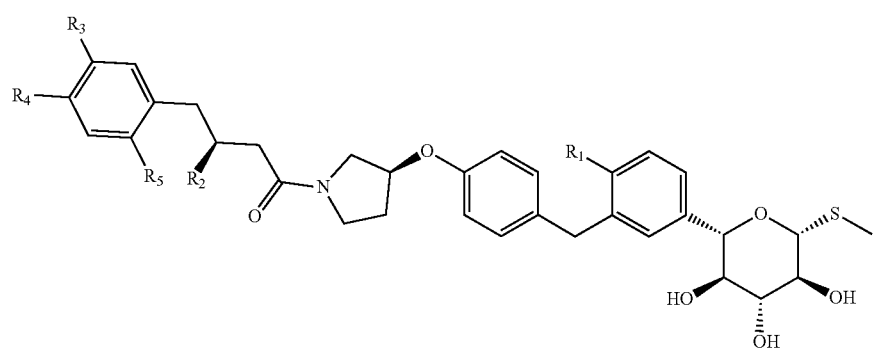
(I-3a-2)
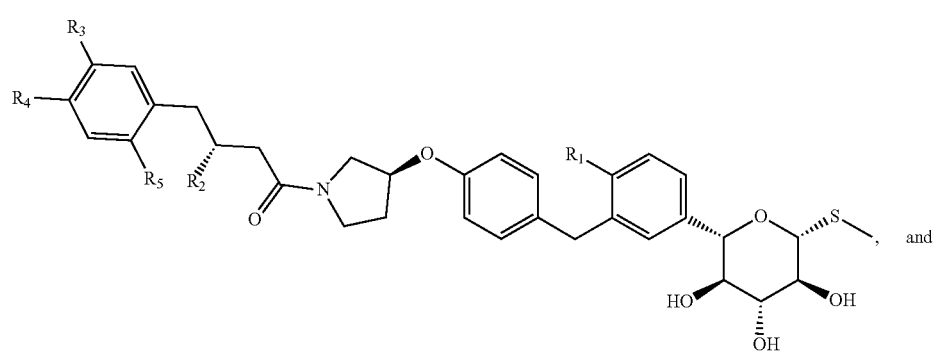
(I-3b-1)
, and

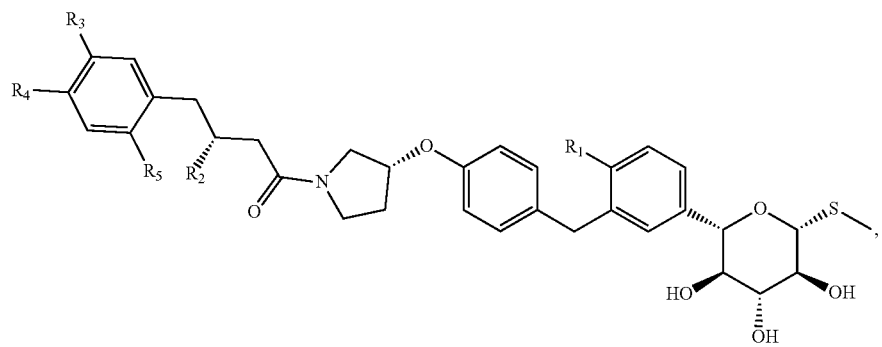
wherein
R₁, R₂, R₃, R₄, and R₅ are as defined in claim 11.
13. The compound represented by the following formula, or stereoisomer, tautomer, or pharmaceutically acceptable salt thereof, wherein the compound is selected from the group consisting of:
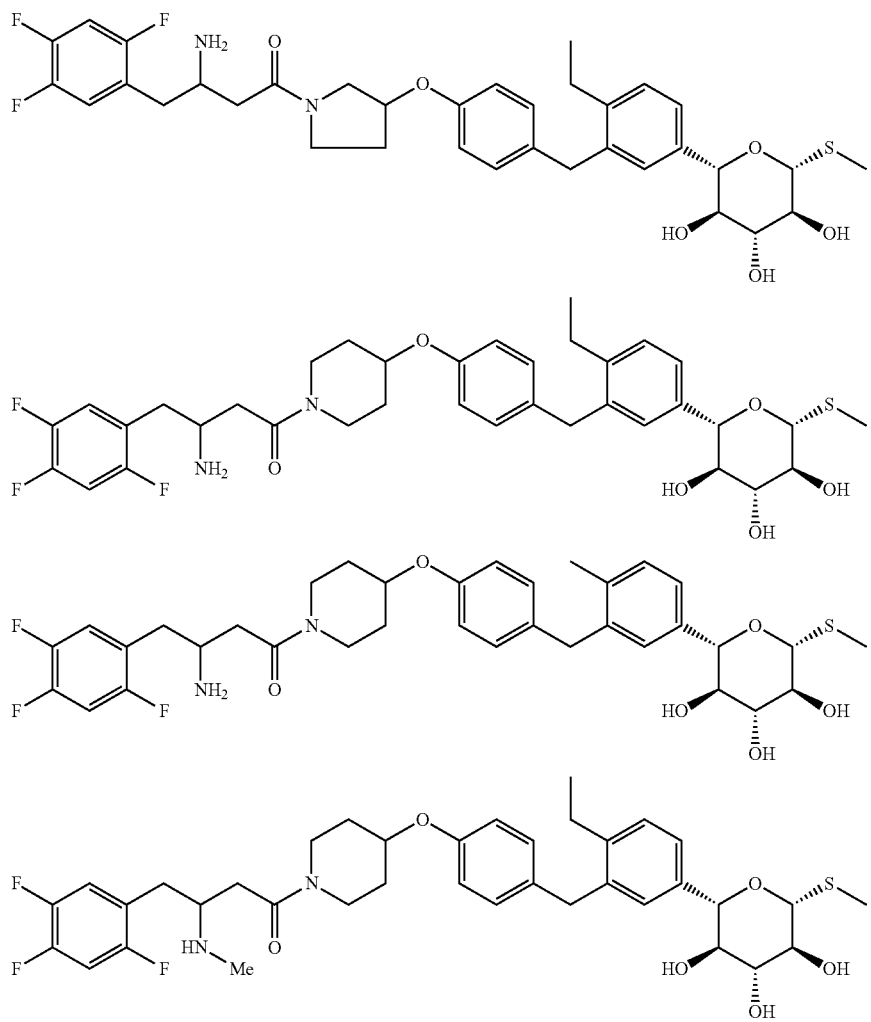

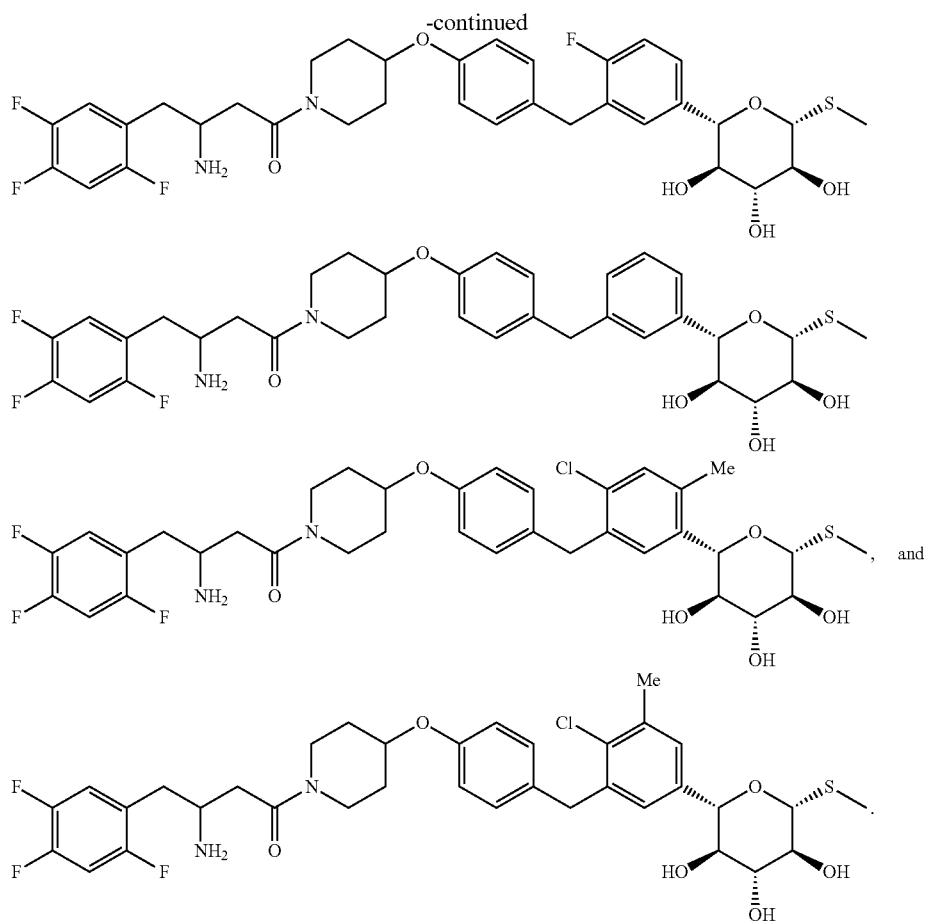
14. The compound, or stereoisomer, tautomer, or pharmaceutically acceptable salt thereof according to claim 13, wherein the compound is selected from the group consisting of:
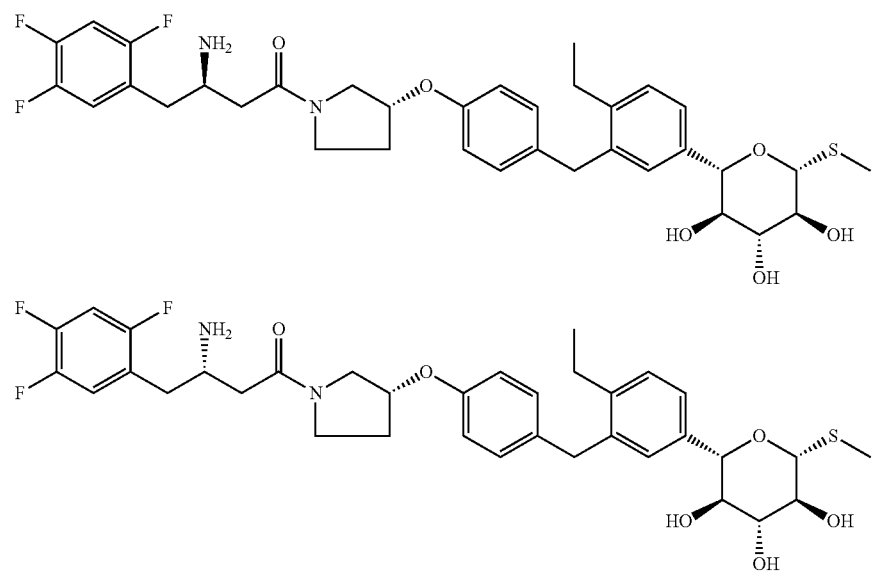

-continued
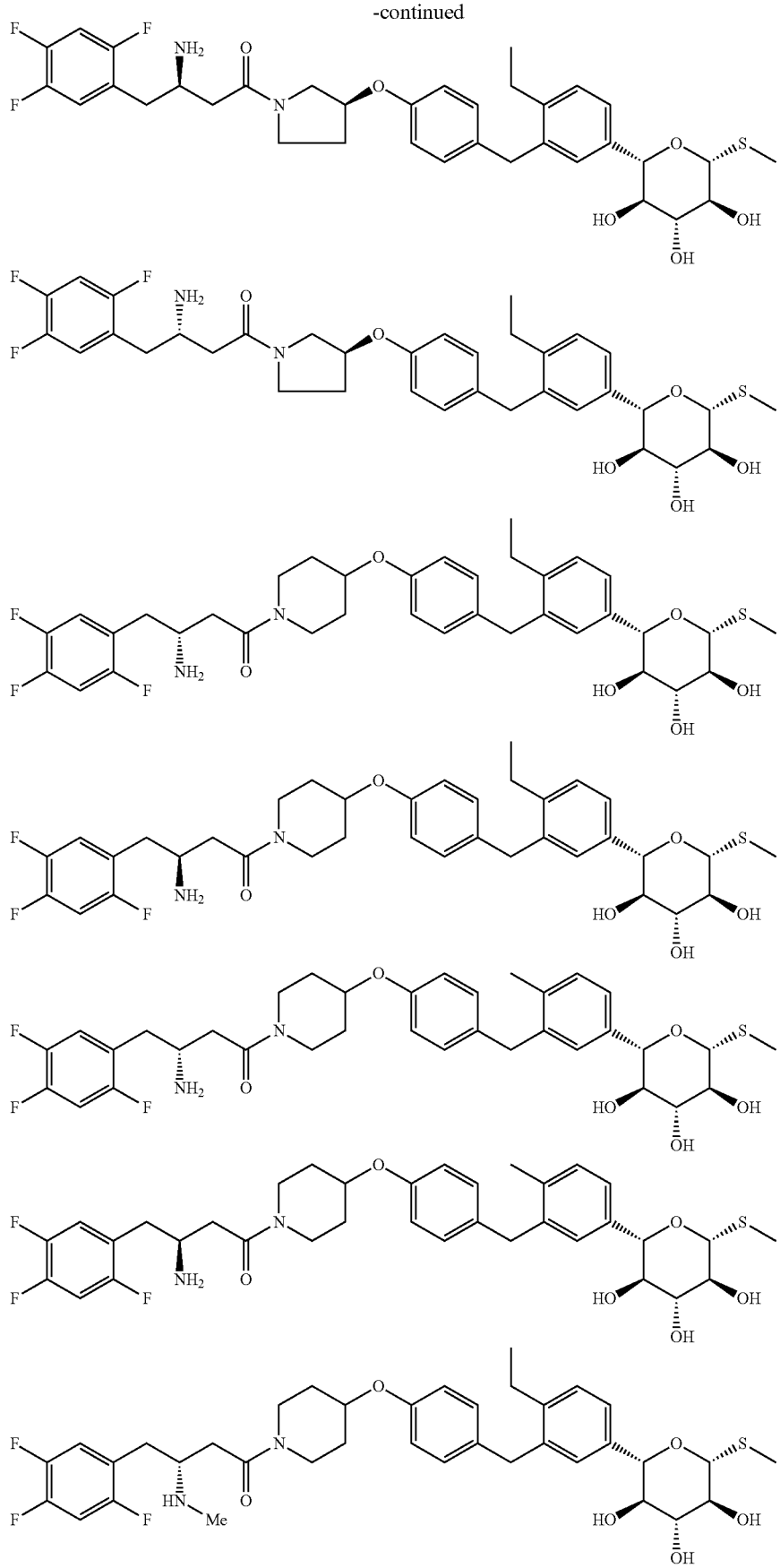

-continued
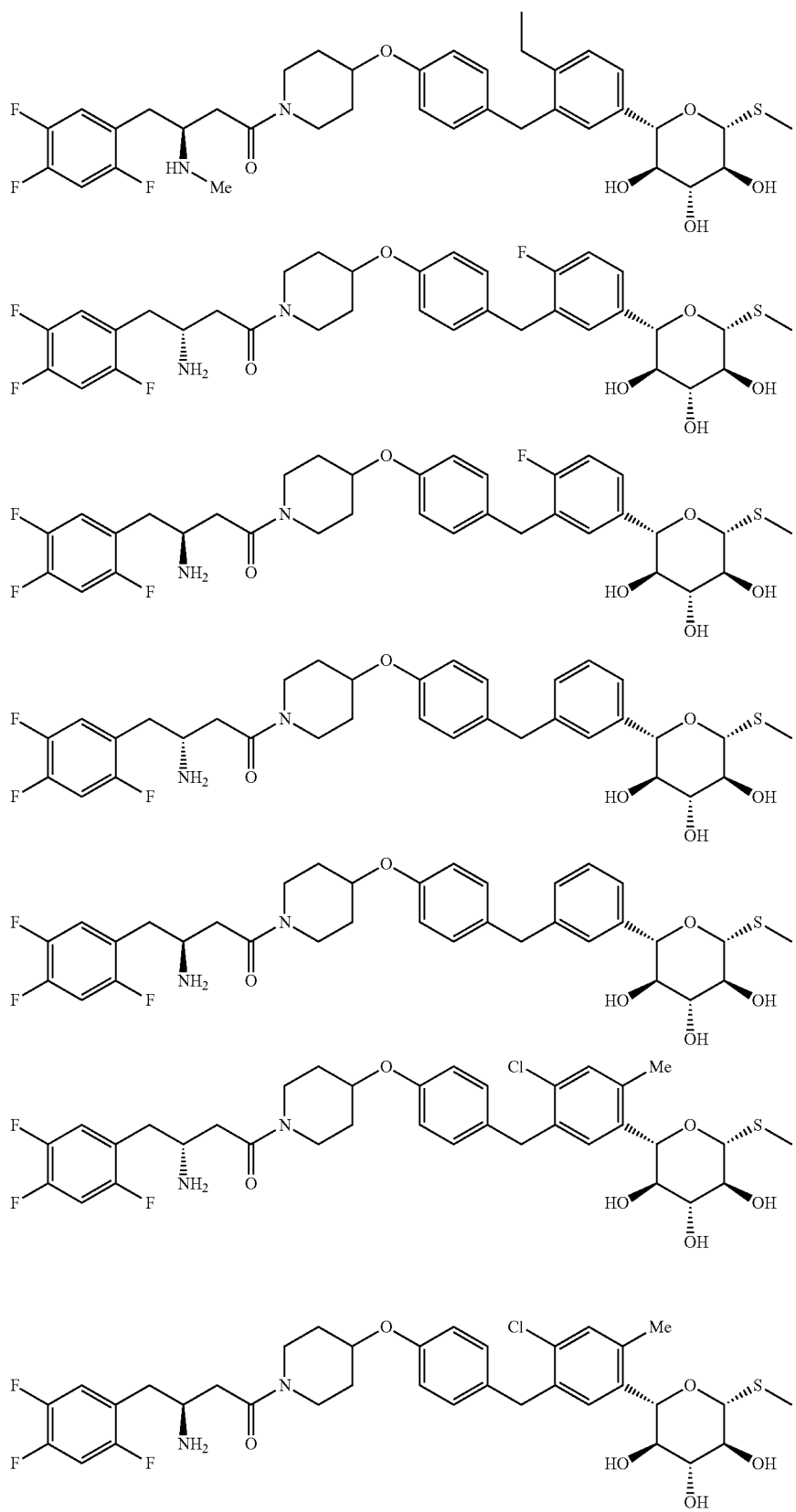

-continued

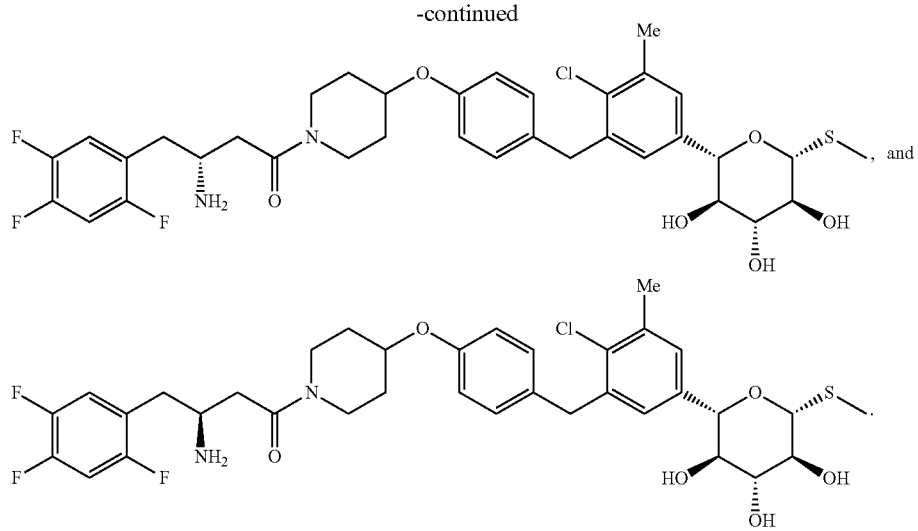

15. A pharmaceutical composition comprising a therapeutically effective amount of the compound, or stereoisomer, tautomer, or pharmaceutically acceptable salt thereof according to claim 1 as an active ingredient, and pharmaceutically acceptable carrier(s).

16. A method of treating disease associated with SGLT1 in a subject in need thereof, comprising administering to the subject the compound, or stereoisomer, tautomer, or pharmaceutically acceptable salt thereof according to claim 1, wherein the disease associated with SGLT1 is diabetes or obesity.

17. A method of treating a disease associated with SGLT1 in a subject in need thereof, comprising administering to the subject the composition according to claim 15, wherein the disease associated with SGLT1 is diabetes or obesity.

* * * * *